United States Patent
Gottesman et al.

(10) Patent No.: US 11,452,738 B2
(45) Date of Patent: Sep. 27, 2022

(54) TREATMENT OF THYMIC STROMAL LYMPHOPOIETIN (TSLP) RELATED DISEASES BY INHIBITION OF LONG-FORM TSLP TRANSCRIPTS

(71) Applicant: EMPIRICO INC., San Diego, CA (US)

(72) Inventors: Omri Gottesman, San Diego, CA (US); Shannon Bruse, San Diego, CA (US); Brian Cajes, San Diego, CA (US); David Lewis, Madison, WI (US); David Rozema, Cross Plains, WI (US)

(73) Assignee: EMPIRICO INC., San Diego, CA (US)

( * ) Notice: Subject to any disclaimer, the term of this patent is extended or adjusted under 35 U.S.C. 154(b) by 0 days.

(21) Appl. No.: 17/419,590

(22) PCT Filed: Jan. 3, 2020

(86) PCT No.: PCT/US2020/012188
§ 371 (c)(1),
(2) Date: Jun. 29, 2021

(87) PCT Pub. No.: WO2020/142693
PCT Pub. Date: Jul. 9, 2020

(65) Prior Publication Data
US 2022/0040220 A1 Feb. 10, 2022

Related U.S. Application Data

(60) Provisional application No. 62/788,551, filed on Jan. 4, 2019.

(51) Int. Cl.
*C12N 15/11* (2006.01)
*A61K 31/7125* (2006.01)
*C12N 15/113* (2010.01)

(52) U.S. Cl.
CPC ...... *A61K 31/7125* (2013.01); *C12N 15/1136* (2013.01); *C12N 2310/11* (2013.01); *C12N 2310/14* (2013.01); *C12N 2310/315* (2013.01); *C12N 2310/341* (2013.01); *C12N 2310/343* (2013.01); *C12N 2310/346* (2013.01); *C12N 2320/11* (2013.01)

(58) Field of Classification Search
None
See application file for complete search history.

(56) References Cited

U.S. PATENT DOCUMENTS

| | | | |
|---|---|---|---|
| 5,138,045 | A | 8/1992 | Cook et al. |
| 5,218,105 | A | 6/1993 | Cook et al. |
| 5,432,272 | A | 7/1995 | Benner |
| 5,459,255 | A | 10/1995 | Cook et al. |
| 9,441,227 | B2 | 9/2016 | Rossi et al. |
| 2005/0246794 | A1 * | 11/2005 | Khvorova .......... C12N 15/1137 536/23.1 |
| 2012/0022143 | A1 | 1/2012 | Jadhav et al. |
| 2020/0071393 | A1 | 3/2020 | Comeau et al. |

FOREIGN PATENT DOCUMENTS

| | | | | |
|---|---|---|---|---|
| KR | 20160016475 | A * | 2/2016 | ............ A61K 48/00 |
| WO | WO-2010111490 | A2 | 9/2010 | |
| WO | WO-2015009996 | A1 | 1/2015 | |
| WO | WO-2017042701 | A1 | 3/2017 | |

OTHER PUBLICATIONS

Machine translation of KR20160016475A, 23 pages (Year: 2016).*
Bjerkan et al., The short form of TSLP is constitutively translated in human keratinocytes and has characteristics of an antimicrobial peptide. Mucosal Immunology 8(1):49-56 (2015).
Camelo et al., IL-33, IL-25, and TSLP induce a distinct phenotypic and activation profile in human type 2 innate lymphoid cells. Blood Advances 1(10):577-589 (2017).
Chen et al., Targeting TSLP with shRNA alleviates airway inflammation and decreases epithelial CCL17 in a murine model of asthma. Molecular Therapy Nucleic Acids 5:e316 [1-11] doi: 10.1038/mtna.2016.29 (2016).
Dong et al., Distinct roles of short and long thymic stromal lymphopoietin isoforms in house dust mite-induced asthmatic airway epithelial barrier disruption. Scientific Reports 6:39559 [1-14]. doi: 10.1038/srep39559 (2016).
Feng et al., The united allergic airway: connections between allergic rhinitis, asthma, and chronic sinusitis. American Journal of Rhinology and Allergy. 26(3):187-190 (2012).
Fomasa et al., Dichotomy of short and long thymic stromal lymphopoietin isoforms in inflammatory disorders of the bowel and skin. Journal of Allergy and Clinical Immunology 136(2):413-422 (2015).
Harada et al., Functional analysis of the thymic stromal lymphopoietin variants in human bronchial epithelial cells. American Journal of Respiratory Cell and Molecular Biology 40(3):368-374 (2009).
Hui et al., Thymic stromal lymphopoietin (TSLP) secretion from human nasal epithelium is a function of TSLP genotype. Mucosal Immunology 8(5):993-939 (2015).
Hung et al.: shRNA for Thymic Stromal Lymphopoietin: A Novel Therapeutic Approach for Pulmonary Fibrosis. Journal of Cell Science & Therapy 4(3): 1-9 (2013).

(Continued)

*Primary Examiner* — Ekaterina Poliakova-Georgantas
(74) *Attorney, Agent, or Firm* — Wilson Sonsini Goodrich & Rosati

(57) ABSTRACT

Provided are compositions comprising an oligonucleotide that targets Thymic stromal lymphopoietin (TSLP). The oligonucleotide may include a small interfering RNA (siRNA) or an antisense oligonucleotide (ASO). Also provided herein are methods of treating an airway disorder by providing an oligonucleotide that targets TSLP to a subject in need thereof. In some embodiments, the oligonucleotide targeting is specific for a long isoform of TSLP (1fTSLP).

15 Claims, 3 Drawing Sheets
Specification includes a Sequence Listing.

(56) References Cited

OTHER PUBLICATIONS

Kariyawasam et al., Allergic rhinitis, chronic rhinosinusitis and asthma: unravelling a complex relationship. Current Opinion in Otolaryngology and Head Neck Surgery 21(1):79-86 (2013).

Li et al., Characterization of signaling pathways regulating the expression of pro-inflammatory long form thymic stromal lymphopoietin upon human metapneumovirus infection. Scientific Reports 8(1):883 [1-11] doi: 10.1038/s41598-018-19225-0 (2018).

Omori et al., Induction of IL-4 expression in CD4(+) T cells by thymic stromal lymphopoietin. Journal of Immunology 178(3):1396-1404 (2007).

PCT/US2020/012188 International Invitation to Pay Additional Fees dated Mar. 17, 2020.

PCT/US2020/012188 International Search Report and Written Opinion dated Jun. 12, 2020.

Rochman et al., TSLP signaling in CD4+ T cells programs a pathogenic T helper 2 cell state. doi: 10.1126/scisignal.aam885 Science Signaling 11(521):1-12 (2018).

Watanabe et al., Human thymic stromal lymphopoietin promotes dendritic cell-mediated CD4+ T cell homeostatic expansion. Nature Immunology 5(4):426-434 (2004).

Ziegler et al., The biology of thymic stromal lymphopoietin (TSLP). Advances in Pharmacology 66:129-155 (2013).

\* cited by examiner

TREATMENT OF THYMIC STROMAL LYMPHOPOIETIN (TSLP) RELATED DISEASES BY INHIBITION OF LONG-FORM TSLP TRANSCRIPTS

CROSS-REFERENCE TO RELATED APPLICATIONS

This application is a § 371 U.S. national stage entry of International Application No. PCT/US2020/012188, filed Jan. 3, 2021, which claims the benefit of U.S. Provisional Application No. 62/788,551, filed Jan. 4, 2019, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 2, 2020, is named 54462-707_601_SL.txt and is 8,727,589 bytes in size.

BACKGROUND

Chronic inflammation commonly affects both the upper and lower airways via similar mechanisms. Clinically, chronic airway inflammation often presents as allergic rhinitis (AR), non-allergic rhinitis (NAR) and chronic rhinosinusitis (CRS) in the upper airway, and as asthma, COPD and the asthma-COPD overlap syndrome (ACOS) in the lower airway. These observations have fostered increasingly strong support for the so-called unified airway hypothesis. The airway is a continuous structure lined with ciliated, pseudostratified columnar epithelium that extends from the nasal vestibule to the distal bronchioles. Its mucosal surface is constantly exposed to environmental insults and is thus highly adapted in its role as the first line of defense, instigated by the innate and adaptive arms of the immune system. Though these diseases are heterogeneous in terms of their presentation and disease course, comprising many endotypes, they all share a common endotype with patients displaying a Th2-dominant response characterized by airway inflammation with local and/or systemic eosinophilia, among other features. The epidemiological and pathophysiological observations have resulted in the established dogma that the eosinophilic endotypes of airway diseases benefit from similar therapeutic approaches, revolving around modulation of the dysregulated innate, adaptive and inflammatory responses that are characteristic of these diseases.

Thymic stromal lymphopoietin (TSLP) is a cytokine that is primarily expressed by epithelial cells and keratinocytes at barrier surfaces such as the lung, gut and skin. TSLP is an "alarmin" and is secreted in response to barrier tissue insults, including respiratory viruses, bacterial peptidoglycan, various cytokines, air pollutants and allergens. Once secreted, it signals through a heterodimeric receptor (IL7R/CRLF2) that is largely expressed on hematopoietic cells including dendritic cells (DCs), T cells, mast cells, type 2 innate lymphoid cells (ILC2s) and eosinophils. TSLP signaling promotes Th2 differentiation of CD4+ T cells both directly and indirectly through DCs and is also involved in the maintenance and function of ILC2 cells and the induction of pathogenic memory Th2 cells.

There are three known RNA transcripts of TSLP, but only two are protein coding: the canonical TSLP transcript variant 1 (NM 033035.5; SEQ ID NO: 14923) and a transcript variant 2 (NM_138551.4; SEQ ID NO: 14924). These two coding transcripts code for the long isoform of TSLP that is comprised of 159 amino acids (1fTSLP; variant 1), and for the short isoform (sfTSLP; variant 2) comprised of the last 63 residues of the C-terminal portion of 1fTSLP. These two isoforms arise not from alternative splicing but from alternate promoters (FIG. 1). sfTSLP does not signal through the TSLP receptor and is therefore functionally divergent from 1fTSLP. sfTSLP is constitutively expressed in barrier tissues and is a potent anti-microbial, while 1fTSLP expression and secretion is typically only observed in disease states. Consistent with 1fTSLP being a pro-inflammatory mediator of disease, 1fTSLP is induced by polyIC, ovalbumin, house dust mite (HDM), TNF-alpha, and IL4/13, whereas sfTSLP is not induced by these allergic and inflammatory stimuli. Notably, in house dust mite (HDM) mouse models of allergic airways disease, both mAb inhibition and genetic KO of 1fTSLP have been shown to protect against the development of allergic airways disease. Conversely, delivery of human sfTSLP to the lung has been shown to ameliorate allergic inflammation in the HDM mouse model. Given the divergent functions and contrasting effects of long and short form TSLP, it is desirable to develop a therapeutic that will specifically target the pro-inflammatory 1fTSLP while leaving the anti-microbial and anti-inflammatory sfTSLP intact.

Accordingly, therapies designed to inhibit 1fTSLP delivered locally to the lung via inhalation, or systemically, may be efficacious in treating asthma and related disorders of the upper and lower airway, including chronic rhinosinusitis, nasal polyps and allergic rhinitis.

SUMMARY

Described herein, in some embodiments, are compositions comprising an oligonucleotide that targets a long isoform of Thymic stromal lymphopoietin (1fTSLP) and when administered to a subject in an effective amount decreases an eosinophil count. In some embodiments, the eosinophil count is decreased by about 10% or more, as compared to prior to administration. Also described herein, in some embodiments, are compositions comprising an oligonucleotide that targets 1fTSLP and when administered to a subject in an effective amount decreases an inflammatory marker. In some embodiments, the inflammatory marker is decreased by about 10% or more, as compared to prior to administration. Also described herein, in some embodiments, are compositions comprising an oligonucleotide that targets 1fTSLP and when administered to a subject in an effective amount decreases mucus production. In some embodiments, the mucus production is decreased by about 10% or more, as compared to prior to administration. In some embodiments, the 1fTSLP is encoded by a nucleic acid comprising SEQ ID NO: 14923, or a variant thereof at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical, to SEQ ID NO: 14923. In some embodiments, the 1fTSLP is encoded by a nucleic acid comprising SEQ ID NO: 14923. In some embodiments, the oligonucleotide is specific for 1fTSLP, and/or does not target a short isoform of TSLP (sfTSLP). In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. In some embodiments, the oligonucleotide comprises 1, 2, 3, 4, 5, 6, 7, 8, 9, 10, 11, 12, 13, 14, 15, 16, 17, 18, 19, or 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages. In some embodiments, the oligonucleotide comprises a modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises one or more 2'fluoro modified nucleosides. In some embodiments, the modified nucleoside comprises a 2' O-alkyl modified nucleoside. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof. In some embodiments, the oligonucleotide comprises 1, 2, 3, 4, 5, 6, 7, 8, 9, 10, 11, 12, 13, 14, 15, 16, 17, 18, 19, 20, or 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides. In some embodiments, the oligonucleotide comprises a small interfering RNA (siRNA) comprising a sense strand and an antisense strand. In some embodiments, the sense strand is 12-30 nucleosides in length. In some embodiments, the antisense strand is 12-30 nucleosides in length. Also described herein, in some embodiments, are compositions an oligonucleotide that targets 1fTSLP, wherein the oligonucleotide comprises a siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14923. Also described herein, in some embodiments, are compositions an oligonucleotide that targets 1fTSLP, wherein the oligonucleotide comprises an siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14925. In some embodiments, the sense strand and the antisense strand form a double-stranded RNA duplex. In some embodiments, the first base pair of the double-stranded RNA duplex is an AU base pair. In some embodiments, the sense strand comprises a 3' overhang comprising 1, 2, or more nucleosides. In some embodiments, the 3' overhang of the sense strand comprises 2 nucleosides. In some embodiments, the antisense strand comprises a 3' overhang comprising 1, 2, or more nucleosides. In some embodiments, the 3' overhang of the antisense strand comprises 2 nucleosides. In some embodiments, the sense strand comprises a nucleoside sequence comprising or consisting of the sequence of any one of SEQ ID NOs: 14935-17526, or a nucleic acid sequence thereof having 1 or 2 nucleoside substitutions, additions, or deletions. In some embodiments, the sense strand comprises a nucleoside sequence comprising or consisting of the sequence of any one of SEQ ID NOs: 14935-17526. In some embodiments, the antisense strand comprises a nucleoside sequence comprising or consisting of the sequence of any one of SEQ ID NOs: 26134-28725, or a nucleic acid sequence thereof having 1 or 2 nucleoside substitutions, additions, or deletions. In some embodiments, the antisense strand comprises a nucleoside sequence comprising or consisting of the sequence of any one of SEQ ID NOs: 26134-28725. In some embodiments, the siRNA binds with a 17 mer in a non-human primate 1fTSLP mRNA. In some embodiments, the siRNA binds with a 19 mer in a human 1fTSLP mRNA. In some embodiments, the siRNA binds with a human 1fTSLP mRNA and less than or equal to 20 human off-targets, with no more than 2 mismatches in the antisense strand. In some embodiments, the siRNA binds with a human 1fTSLP mRNA target site that does not harbor an SNP, with a minor allele frequency (MAF) greater or equal to 1% (pos. 2-18). In some embodiments, the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326, or a nucleic acid sequence thereof having 1 or 2 nucleoside substitutions, additions, or deletions; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525, or a nucleic acid sequence thereof having 1 or 2 nucleoside substitutions, additions, or deletions. In some embodiments, the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525. In some embodiments, the sense strand comprises the nucleoside sequence of any one of SEQ ID NOs: 14942, 14947, 14948, 14950, 14957, 14959, 15004, 15035, 15039, 15040, 15041, 15043, 15047, 15048, 15049, 15050, 15051, 15057, 15059, 15082, 15094, 15096, 15097, 15098, 15102, 15107, 15108, 15111, 15114, 15123, 15127, 15128, 15164, 15184, 15186, 15187, 15188, 15190, 15191, 15194, 15195, 15230, 15235, 15236, 15238, 15241, 15246, 15252, 15260, 15263, 15272, 15276, 15278, 15279, 15283, 15294, 15302, 15307, 15314, 15322, 15324, or 15326; and/or wherein the antisense strand comprises the nucleoside sequence of any one of SEQ ID NOs: 26141, 26146, 26147, 26149, 26156, 26158, 26203, 26234, 26238, 26239, 26240, 26242, 26246, 26247, 26248, 26249, 26250, 26256, 26258, 26281, 26293, 26295, 26296, 26297, 26301, 26306, 26307, 26310, 26313, 26322, 26326, 26327, 26363, 26383, 26385, 26386, 26387, 26389, 26390, 26393, 26394, 26429, 26434, 26435, 26437, 26440, 26445, 26451, 26459, 26462, 26471, 26475, 26477, 26478, 26482, 26493, 26501, 26506, 26513, 26521, 26523, or 26525. In some embodiments, the sense strand comprises the nucleoside sequence of any one of SEQ ID NOs: 15041, 15048, 15051, 15082, 15096, 15111, 15114, 15123, 15128, 15187, 15194, 15230, 15235, 15238, 15241, 15252, 15272, 15278, 15307, or 15326; and/or wherein the antisense strand comprises the nucleoside sequence of any one of SEQ ID NOs: 26240, 26247, 26250, 26281, 26295, 26310, 26313, 26322, 26327, 26386, 26393, 26429, 26434, 26437, 26440, 26451, 26471, 26477, 26506, or 26525. In some embodiments, the sense strand comprises the nucleoside sequence of any one of SEQ ID NOs: 15048, 15051, 15082, 15096, 15111, 15114, 15123, 15128, 15194, 15230, 15235, 15238, 15241, 15252, 15272, 15278, 15307, or 15326; and/or wherein the antisense strand comprises the nucleoside sequence of any one of SEQ ID NOs: 26247, 26250, 26281, 26295, 26310, 26313, 26322, 26327, 26393, 26429, 26434, 26437, 26440, 26451, 26471, 26477, 26506, or 26525. In some embodiments, the sense strand comprises the nucleoside sequence of any one of SEQ ID NOs: 17527-20118, or a nucleic acid sequence thereof having 1 or 2 nucleoside substitutions, additions, or deletions. In some embodiments, the sense strand comprises the nucleoside sequence of any one of SEQ ID NOs: 17527-20118. In some embodiments, the sense strand comprises the nucleoside sequence of any one of SEQ ID NOs: 20119-22710, or a nucleic acid sequence thereof having 1 or 2 nucleoside substitutions, additions, or deletions. In some embodiments, the sense strand comprises the nucleoside sequence of any one of SEQ ID NOs: 20119-22710. In some embodiments, the antisense strand comprises the nucleoside sequence of any one of SEQ ID NOs: 28922-31513, or a nucleic acid sequence thereof having 1 or 2 nucleoside substitutions, additions, or deletions. In some embodiments, the antisense strand comprises the nucleoside sequence of any one of SEQ ID NOs: 28922-31513. In some embodiments, the antisense strand comprises the nucleoside sequence of any one of SEQ ID NOs: 31514-34105, or a nucleic acid sequence thereof having 1 or 2 nucleoside substitutions, additions, or deletions. In some embodiments, the antisense strand comprises the nucleoside sequence of any one of SEQ ID NOs: 31514-34105. In some embodiments, the sense strand comprises modification pattern 1S: 5'-NfsnsNfnNfnNfnNfnNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5'-nsnsnnNfnNfNfNfnnnnnnnnnnnsnsn-3' (SEQ ID NO: 34504), wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5'-nsnsnnNfnNfnNfnnnnnnnnnnnsnsn-3' (SEQ ID NO: 34507), wherein "Nf" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfnNfnNfnNfnNfnNfnNfnNfnNfnNfsnsnN-Lipid-3' (SEQ ID NO: 34508), wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 5S: 5'-nsnsnnNfnNfNfNfnnnnnnnnnnnsnsnN-Lipid-3' (SEQ ID NO: 34509), wherein "Nf" is a 2' fluoro-modified nucleoside, "n" is a 2' O-methyl modified nucleoside, "s" is a phosphorothioate linkage, and N comprises one or more nucleosides. In some embodiments, the antisense strand comprises modification pattern 1AS: 5'-nsNfsnNfnNfnNfnNfnnnNfnNfnNfsnsn-3' (SEQ ID NO: 34503), wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnnnNfnNfNfNfnnnnNfnNfnnnsnsn-3' (SEQ ID NO: 34510), wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsNfsnnnNfnnnnnnnNfnNfnnnsnsn-3' (SEQ ID NO: 34505), wherein "Nf" is a 2' fluoro-modified nucleoside, "n"

is a 2' O-methyl modified nucleoside, and "s" is a phosphorothioate linkage. In some embodiments, the antisense strand comprises modification pattern 4AS: 5'-nsNfsnNfnNfnnnnnnnNfnNfnnnsnsn-3' (SEQ ID NO: 34511), wherein "Nf" is a 2' fluoro-modified nucleoside, "n" is a 2' O-methyl modified nucleoside, and "s" is a phosphorothioate linkage. In some embodiments, the sense strand comprises pattern 1S and the antisense strand comprises pattern 1AS, 2AS, 3AS, or 4AS. In some embodiments, the sense strand comprises pattern 2S and the antisense strand comprises pattern 1AS, 2AS, 3AS, or 4AS. In some embodiments, the sense strand comprises pattern 3S and the antisense strand comprises pattern 1AS, 2AS, 3AS, or 4AS. In some embodiments, the sense strand comprises pattern 4S and the antisense strand comprises pattern 1AS, 2AS, 3AS, or 4AS. In some embodiments, the sense strand comprises the nucleoside sequence of any one of SEQ ID NOs: 17533, 17534, 17539, 17540, 17542, 17549, 17551, 17552, 17553, 17554, 17565, 17596, 17597, 17605, 17627, 17631, 17632, 17633, 17635, 17639, 17640, 17641, 17642, 17643, 17644, 17648, 17649, 17651, 17654, 17674, 17686, 17688, 17689, 17690, 17693, 17694, 17699, 17700, 17703, 17706, 17709, 17715, 17719, 17720, 17756, 17766, 17770, 17776, 17778, 17779, 17780, 17782, 17783, 17786, 17787, 17789, 17822, 17827, 17828, 17830, 17832, 17833, 17838, 17844, 17845, 17852, 17855, 17856, 17864, 17866, 17868, 17870, 17871, 17874, 17875, 17878, 17886, 17894, 17895, 17899, 17902, 17906, 17911, 17912, 17913, 17914, 17916, or 17918; and/or wherein the antisense strand comprises the nucleoside sequence of any one of SEQ ID NOs: 28928, 28929, 28934, 28935, 28937, 28944, 28946, 28947, 28948, 28949, 28960, 28991, 28992, 29000, 29022, 29026, 29027, 29028, 29030, 29034, 29035, 29036, 29037, 29038, 29039, 29043, 29044, 29046, 29049, 29069, 29081, 29083, 29084, 29085, 29088, 29089, 29094, 29095, 29098, 29101, 29104, 29110, 29114, 29115, 29151, 29161, 29165, 29171, 29173, 29174, 29175, 29177, 29178, 29181, 29182, 29184, 29217, 29222, 29223, 29225, 29227, 29228, 29233, 29239, 29240, 29247, 29250, 29251, 29259, 29261, 29263, 29265, 29266, 29269, 29270, 29273, 29281, 29289, 29290, 29294, 29297, 29301, 29306, 29307, 29308, 29309, 29311, or 29313. In some embodiments, the sense strand comprises the nucleoside sequence of any one of SEQ ID NOs: 17534, 17539, 17540, 17542, 17549, 17551, 17596, 17627, 17631, 17632, 17633, 17635, 17639, 17640, 17641, 17642, 17643, 17649, 17651, 17674, 17686, 17688, 17689, 17690, 17694, 17699, 17700, 17703, 17706, 17715, 17719, 17720, 17756, 17776, 17778, 17779, 17780, 17782, 17783, 17786, 17787, 17822, 17827, 17828, 17830, 17833, 17838, 17844, 17852, 17855, 17864, 17868, 17870, 17871, 17875, 17886, 17894, 17899, 17906, 17914, 17916, or 17918; and/or wherein the antisense strand comprises the nucleoside sequence of any one of SEQ ID NOs: 28929, 28934, 28935, 28937, 28944, 28946, 28991, 29022, 29026, 29027, 29028, 29030, 29034, 29035, 29036, 29037, 29038, 29044, 29046, 29069, 29081, 29083, 29084, 29085, 29089, 29094, 29095, 29098, 29101, 29110, 29114, 29115, 29151, 29171, 29173, 29174, 29175, 29177, 29178, 29181, 29182, 29217, 29222, 29223, 29225, 29228, 29233, 29239, 29247, 29250, 29259, 29263, 29265, 29266, 29270, 29281, 29289, 29294, 29301, 29309, 29311, or 29313. In some embodiments, the sense strand comprises the nucleoside sequence of any one of SEQ ID NOs: 17633, 17640, 17643, 17674, 17688, 17703, 17706, 17715, 17720, 17779, 17786, 17822, 17827, 17830, 17833, 17844, 17864, 17870, 17899, or 17918; and/or wherein the antisense strand comprises the nucleoside sequence of any one of SEQ ID NOs: 29028, 29035, 29038, 29069, 29083, 29098, 29101, 29110, 29115, 29174, 29181, 29217, 29222, 29225, 29228, 29239, 29259, 29265, 29294, or 29313. In some embodiments, the sense strand comprises the nucleoside sequence of any one of SEQ ID NOs: 17640, 17643, 17674, 17688, 17703, 17706, 17715, 17720, 17786, 17822, 17827, 17830, 17833, 17844, 17864, 17870, 17899, or 17918; and/or wherein the antisense strand comprises the nucleoside sequence of any one of SEQ ID NOs: 29035, 29038, 29069, 29083, 29098, 29101, 29110, 29115, 29181, 29217, 29222, 29225, 29228, 29239, 29259, 29265, 29294, or 29313. In some embodiments, the oligonucleotide comprises an antisense oligonucleotide (ASO). In some embodiments, the ASO is single-stranded and 12-30 nucleosides in length. Also described herein, in some embodiments, are compositions comprising an oligonucleotide that targets 1fTSLP, wherein the oligonucleotide comprises an ASO comprising an antisense strand about 12-30 nucleosides in length and comprising a nucleoside sequence comprising about 12-30 contiguous nucleosides of one of SEQ ID NO: 14923. Also described herein, in some embodiments, are compositions comprising an oligonucleotide that targets TSLP, wherein the oligonucleotide comprises an ASO comprising an antisense strand about 12-30 nucleosides in length and comprising a nucleoside sequence comprising about 12-30 contiguous nucleosides of one of SEQ ID NO: 14925. In some embodiments, the ASO is 15-25 nucleosides in length. In some embodiments, the ASO is 20 nucleosides in length. In some embodiments, the ASO comprises a nucleoside sequence comprising or consisting of the sequence of any one of SEQ ID NOs: 9971-12561, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 9971-12561. In some embodiments, the ASO comprises a nucleoside sequence comprising or consisting of the sequence of any one of SEQ ID NOs: 23299-25889, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 23299-25889. In some embodiments, the ASO comprises modification pattern: 5'-nsnsnsnsnsdNsdNsdNsdNsdNsdNsdNsdNsdNsnsnsn snsn-3' (SEQ ID NO: 34506) where "dN" is any deoxynucleotide, "n" is a 2'O-methyl or 2'O-methoxyethyl-modified nucleoside, and "s" is a phosphorothioate linkage. In some embodiments, the composition is a pharmaceutical composition. In some embodiments, the composition is sterile. Some embodiments further comprise a pharmaceutically acceptable carrier. In some embodiments, the pharmaceutically acceptable carrier comprises water, a buffer, or a saline solution. In some embodiments, the composition is formulated for administration by inhalation. In some embodiments, the oligonucleotide targets a sequence within the first 412 nucleotides of SEQ ID NO: 14923.

Described herein, in some embodiments, are methods of treating an airway disorder such as an airway inflammation disorder in a subject in need thereof, the method comprising administering to the subject a composition comprising an oligonucleotide that targets 1fTSLP. In some embodiments, the airway inflammation disorder comprises asthma. In some embodiments, the airway inflammation disorder comprises nasal polyps. In some embodiments, the airway inflammation disorder comprises allergic rhinitis. In some embodiments, the airway inflammation disorder comprises chronic rhinosinusitis. In some embodiments, the airway inflammation disorder comprises an increased blood eosinophil count. In some embodiments, the administration is by inhalation. In some embodiments, the subject is an animal, a mammal, a dog, a cat, cattle, a rodent, a mouse, a rat, a primate, or a monkey. In some embodiments, the subject is a human. In some embodiments, the subject is ≥40 years of age. In some embodiments, the subject is ≤85 years of age. In some embodiments, the subject is ≥40 and ≤85 years of age. In some embodiments, a baseline measurement is obtained from the subject prior to administering the composition to the subject. In some embodiments, the baseline measurement is a baseline observational measurement. In some embodiments, the baseline observational measurement is obtained using a scoring system. In some embodiments, the baseline observational measurement is obtained using microscopy. In some embodiments, the baseline observational measurement is obtained directly from the subject's skin or airway. In some embodiments, the baseline observational measurement is obtained from an image of the subject's skin or airway. In some embodiments, the baseline observational measurement is a baseline number of nasal polyps. In some embodiments, the baseline observational measurement is a baseline nasal polyp size. In some embodiments, the baseline observational measurement is a baseline mucus measurement. In some embodiments, the baseline observational measurement is a baseline mucus production measurement. In some embodiments, the baseline observational measurement is a baseline airway constriction measurement. In some embodiments, the baseline observational measurement is a baseline inflammation measurement, a baseline swelling measurement, or a baseline redness measurement. In some embodiments, the baseline measurement is obtained in a sample obtained from the subject prior to administering the composition to the subject. In some embodiments, the sample is an airway sample. In some embodiments, the sample is a mucus sample. In some embodiments, the sample is an airway tissue sample In some embodiments, the sample is an airway cell sample In some embodiments, the sample is a blood sample, a plasma sample, or a serum sample. In some embodiments, the baseline measurement is obtained using microscopy, PCR, an immunoassay, a colorimetric assay, or a fluorescence assay. In some embodiments, the baseline measurement is a baseline blood eosinophil measurement. In some embodiments, the baseline measurement is a baseline MUC5AC measurement. In some embodiments, the baseline measurement is a baseline inflammatory marker mRNA measurement. In some embodiments, the baseline measurement is a baseline inflammatory marker protein measurement. In some embodiments, the inflammatory marker comprises IL-4, IL-5, IL-13, or TNFα. In some embodiments, the baseline measurement is a baseline 1fTSLP mRNA measurement. In some embodiments, the baseline measurement is a baseline 1fTSLP protein measurement. In some embodiments, the baseline measurement is a baseline sfTSLP mRNA measurement. In some embodiments, the baseline measurement is a baseline sfTSLP protein measurement. In some embodiments, the composition reduces an observational measurement relative to the baseline observational measurement. In some embodiments, the observational measurement is obtained using a scoring system. In some embodiments, the observational measurement is obtained using microscopy. In some embodiments, the observational measurement is obtained directly from the subject's skin or airway. In some embodiments, the observational measurement is obtained from an image of the subject's skin or airway. In some embodiments, the observational measurement is a number of nasal polyps. In some embodiments, the observational measurement is a nasal polyp size. In some embodiments, the observational measurement is a mucus measurement. In some embodiments, the observational measurement is a mucus production measurement. In some embodiments, the observational measurement is an airway constriction measurement. In some embodiments, the observational measurement is an inflammation measurement, a swelling measurement, or a redness measurement. In some embodiments, the composition reduces a blood eosinophil measurement relative to the baseline blood eosinophil measurement. In some embodiments, the blood eosinophil measurement is obtained using microscopy, PCR, an immunoassay, a colorimetric assay, or a fluorescence assay. In some embodiments, the composition reduces a MUC5AC measurement relative to the baseline MUC5AC measurement. In some embodiments, the MUC5AC measurement is obtained using microscopy, PCR, an immunoassay, a colorimetric assay, or a fluorescence assay. In some embodiments, the composition reduces an inflammatory marker mRNA measurement relative to the baseline inflammatory marker mRNA measurement. In some embodiments, the inflammatory marker mRNA measurement is obtained using PCR. In some embodiments, the composition reduces an inflammatory marker protein measurement relative to the baseline inflammatory marker protein measurement. In some embodiments, the inflammatory marker protein measurement is obtained using microscopy, an immunoassay, a colorimetric assay, or a fluorescence assay. In some embodiments, the inflammatory marker comprises IL-4, IL-5, IL-13, or TNFα. In some embodiments, the composition reduces a 1fTSLP mRNA measurement relative to the baseline 1fTSLP mRNA measurement. In some embodiments, the 1fTSLP mRNA measurement is obtained using PCR. In some embodiments, the composition reduces a 1fTSLP protein measurement relative to the baseline 1fTSLP protein measurement. In some embodiments, the 1fTSLP protein measurement is obtained using microscopy, an immunoassay, a colorimetric assay, or a fluorescence assay. In some embodiments, the composition does not affect a sfTSLP mRNA measurement relative to the baseline sfTSLP mRNA measurement. In some embodiments, the sfTSLP mRNA measurement is obtained using PCR. In some embodiments, the composition does not affect a sfTSLP protein measurement relative to the baseline sfTSLP protein measurement. In some embodiments, the sfTSLP protein measurement is obtained using microscopy, an immunoassay, a colorimetric assay, or a fluorescence assay. In some embodiments, the blood eosinophil measurement is obtained in a second sample obtained from the subject after administering the composition to the subject. In some embodiments, the MUC5AC measurement is obtained in a second sample obtained from the subject after administering the composition to the subject. In some embodiments, the inflammatory marker mRNA measurement is obtained in a second sample obtained from the subject after administering the composition to the subject. In some embodiments, the inflammatory marker protein measurement is obtained in a second sample obtained from the subject after administering the composition to the subject. In some embodiments, the 1fTSLP mRNA measurement is obtained in a second sample obtained from the subject after administering the composition to the subject. In some embodiments, the 1fTSLP protein measurement is obtained in a second sample obtained from the subject after administering the composition to the subject. In some embodiments, the sfTSLP mRNA measurement is obtained in a second sample obtained from the subject after administering the composition to the subject. In some embodiments, the sfTSLP protein measurement is obtained in a second sample obtained from the subject after administering the composition to the subject. In some embodiments, the second sample is an airway sample. In some embodiments, the second sample is a mucus sample. In some embodiments, the second sample is an airway tissue sample. In some embodiments, the second sample is an airway cell sample. In some embodiments, the second sample is a blood sample, a plasma sample, or a serum sample. In some embodiments, the composition and/or oligonucleotide is a composition and/or oligonucleotide as described herein.

Described herein, in some embodiments, are uses of a composition described herein embodiments in a method as described herein.

In some aspects, the present disclosure relates to molecules for inhibition of long-form thymic stromal lymphopoietin (1fTSLP) gene products including dsRNA (dsRNA) agents such as small interfering RNAs (siRNAs) and antisense oligonucleotides for therapeutic use. Further provided are methods of inhibiting the expression of a target gene by administering these agents, e.g., for the treatment of various diseases involving 1fTSLP gene products.

A non-limiting example of a therapeutic molecule for inhibiting TSLP is RNA interference (RNAi), where double-stranded RNAi (dsRNA) can be utilized to block gene expression. Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

Another non-limiting example of a therapeutic molecule for inhibiting TSLP is antisense oligonucleotides. DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H (RNaseH), an activity that is present in most cell types. Antisense molecules can be delivered into cells, as is the case for oligodeoxynucleotides (ODNs), or they can be expressed from endogenous genes as RNA molecules.

Another non-limiting example of a therapeutic molecule for inhibiting TSLP is splice switching antisense oligonucleotides (SSOs). These are short, synthetic, antisense, modified nucleic acids that hybridize with a pre-mRNA and disrupt the normal splicing repertoire of the transcript by blocking the RNA-RNA base-pairing or protein-RNA binding interactions that occur between components of the splicing machinery and the pre-mRNA. Splicing of pre-mRNA is required for the proper expression of the vast majority of protein-coding genes, and thus, targeting the process offers a means to manipulate protein production from a gene. As an example, the splicing of a pre-mRNA can also be used to alter the reading frame downstream of the splice site leading to a truncated protein with impaired function.

Splice switching antisense oligonucleotides differ from mRNA cleaving antisense oligonucleotides in that they do not recruit RNaseH to degrade the pre-mRNA-SSO complex and are strictly steric blocking. This is accomplished through the use of fully, or nearly fully, 2'-modified antisense oligonucleotides that therefore lack the necessary DNA-RNA hybrid region that is recognized by RNaseH. Another type of modified oligonucleotide that has been used extensively to modify splicing are phosphoramidite morpholinos (PMOs). PMOs have a morpholine ring in place of the furanose ring found in natural nucleic acids and a neutral phosphorodiamidate backbone in place of the negatively charged phosphodiester backbone.

In some embodiments, the present disclosure provides methods for inhibiting the action of a natural transcript by using antisense oligonucleotide(s) targeted to any region of the natural transcript. It is also contemplated herein that inhibition of the natural transcript can be achieved by siRNA, ribozymes and small molecules. In an exemplary embodiment, the natural transcript encodes for TSLP, and in some cases, 1fTSLP.

One embodiment provides a method of modulating function and/or expression of an 1fTSLP polynucleotide in patient cells or tissues, in vivo or in vitro, the method comprising contacting said cells or tissues with an antisense oligonucleotide 5 to 30 nucleotides in length, wherein said antisense oligonucleotide has at least 50% sequence identity to a reverse complement of a polynucleotide comprising 5 to 30 consecutive nucleotides within nucleotides 1 to 2629 of SEQ ID NO: 14923, and any variants, alleles, homologs, mutants, derivatives, fragments and complementary sequences thereof, thereby modulating function and/or expression of the 1fTSLP polynucleotide in patient cells or tissues, in vivo or in vitro. In some embodiments, the oligonucleotide comprises a sequence selected from SEQ ID NOS: 9971-12561. In some embodiments, the oligonucleotide comprises a sequence at least about 80%, 85%, 90%, or 95% identical to a sequence selected from SEQ ID NOS: 9971-12561.

In some embodiments, an oligonucleotide targets a natural sequence of 1fTSLP polynucleotides, for example, nucleotides set forth in SEQ ID NO: 14923, and any variants, alleles, homologs, mutants, derivatives, fragments and complementary sequences thereto. In some embodiments, the oligonucleotide comprises a sequence selected from SEQ ID NOS: 1-12561. In some embodiments, the oligonucleotide comprises a sequence at least about 80%, 85%, 90%, or 95% identical to a sequence selected from SEQ ID NOS: 1-12561.

In some embodiments, an oligonucleotide targets a natural sequence of 1fTSLP polynucleotides, for example, nucleotides set forth in SEQ ID NO: 14925, and any variants, alleles, homologs, mutants, derivatives, fragments and complementary sequences thereto. In some embodiments, the oligonucleotide comprises a sequence selected from SEQ ID NOS: 1-12561. In some embodiments, the oligonucleotide comprises a sequence at least about 80%, 85%, 90%, or 95% identical to a sequence selected from SEQ ID NOS: 1-12561.

In some embodiments, a composition comprises one or more antisense oligonucleotides which bind to sense 1fTSLP polynucleotides. In some embodiments, the oligonucleotide comprises a sequence selected from SEQ ID NOS: 9971-12561. In some embodiments, the oligonucleotide comprises a sequence at least about 80%, 85%, 90%, or 95% identical to a sequence selected from SEQ ID NOS: 9971-12561.

In some embodiments, the oligonucleotides comprise one or more modified or substituted nucleotides. In some embodiments, the oligonucleotides comprise one or more modified bonds. In some embodiments, the modified nucleotides comprise modified bases comprising phosphorothioate, methylphosphonate, peptide nucleic acids, 2'-O-methyl, methoxyethly, fluoro- or carbon, methylene or other locked nucleic acid (LNA) molecules. In some embodiments, the modified nucleotides are locked nucleic acid molecules, including a-L-LNA.

In some embodiments, the oligonucleotides are administered to a patient by inhalation, intranasally, subcutaneously, intramuscularly, intravenously or intraperitoneally.

In some embodiments, the oligonucleotides are administered in a pharmaceutical composition. A treatment regimen comprises administering the antisense compounds at least once to a patient; however, this treatment can be modified to include multiple doses over a period of time. The treatment can be combined with one or more other types of therapies.

In some embodiments, the oligonucleotides are encapsulated in a liposome or attached to a carrier molecule (e.g. cholesterol, TAT peptide).

In one aspect, provided herein is an RNA interference (RNAi) agent capable of inhibiting the expression of long-form thymic stromal lymphopoietin (1fTSLP), wherein the RNAi agent comprises a double-stranded RNA (dsRNA) comprising a sense strand and an antisense strand, each strand having 14 to 30 nucleotides. In some embodiments, the dsRNA has a length of 17-30 nucleotide pairs. In some embodiments, the sense strand and antisense strand each have 17-30 nucleotides. In some embodiments, the sense strand comprises a sequence at least about 80%, 85%, 90%, 95%, or 100% identical to a sequence selected from SEQ ID NOS: 1-5184. In some embodiments, the antisense strand comprises a sequence at least about 80%, 85%, 90%, 95%, or 100% identical to the reverse complement of the sense strand. In some embodiments, the antisense strand comprises a sequence at least about 80%, 85%, 90%, 95%, or 100% identical to a sequence selected from SEQ ID NOS: 1-5184. In some embodiments, the sequence of the sense strand comprises SEQ ID NO: 14929 and the sequence of the antisense strand comprises SEQ ID NO: 14930. In some embodiments, the RNAi agent comprises one or more nucleotide modifications selected from the group consisting of LNA, HNA, CeNA, 2'-methoxyethyl, 2'-O-alkyl, 2'-O-allyl, 2'-C-allyl, 2'-fluoro, and 2'-deoxy. In some embodiments, the nucleotides are modified with either 2'-OCH3 or 2'-F. In some embodiments, the RNAi agent comprises at least one ligand. In some embodiments, the RNAi agent comprises one or more nucleotide modifications selected from the group consisting of 2'-O-methyl nucleotide, 2'-deoxyfluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, and 2'-ara-F. In some embodiments, the RNAi agent comprises at least one phosphorothioate or methylphosphonate internucleotide linkage. In some embodiments, the nucleotide at the 1 position of the 5'-end of the antisense strand of the dsRNA is selected from the group consisting of A, dA, dU, U, and dT. In some embodiments, the base pair at the 1 position of the 5'-end of the dsRNA is an AU base pair.

In another aspect, provided here is an RNA interference (RNAi) agent capable of inhibiting the expression of 1fTSLP, wherein the RNAi agent comprises a double-stranded RNA (dsRNA) comprising a sense strand and an antisense strand, each of the strands having 14 to 30 nucleotides, wherein the sense strand contains at least two motifs of three identical modifications on three consecutive nucleotides, a first of said sense strand motifs occurring at a cleavage site in the sense strand and a second of said sense strand motifs occurring at a different region of the sense strand that is separated from the first sense strand motif by at least one nucleotide; and wherein the antisense strand contains at least two motifs of three identical modifications on three consecutive nucleotides, a first of said antisense strand motifs occurring at or near the cleavage site in the antisense strand and a second of said antisense strand motifs occurring at a different region of the antisense strand that is separated from the first antisense strand motif by at least one nucleotide; wherein the modification in the first antisense strand motif is different than the modification in the second antisense strand motif. In some embodiments, at least one of the nucleotides occurring in the first sense strand motif forms a base pair with one of the nucleotides in the first antisense strand motif. In some embodiments, the dsRNA has 17-30 nucleotide base pairs. In some embodiments, the dsRNA has 17-19 nucleotide base pairs. In some embodiments, each strand has 17-23 nucleotides. In some embodiments, the modifications on the nucleotides of the sense strand and/or antisense strand are selected from the group consisting of LNA, HNA, CeNA, 2'-methoxyethyl, 2'-O-alkyl, 2'-O-allyl, 2'-C— allyl, 2'-fluoro, 2'-deoxy, and combinations thereof. In some embodiments, the modifications on the nucleotides of the sense strand and/or antisense strand are 2'-OCH3 or 2'-F. In some embodiments, the RNAi agent comprises a ligand attached to the 3' end of the sense strand.

In another aspect, provided herein is an RNA interference (RNAi) agent capable of inhibiting the expression of 1fTSLP, wherein the RNAi agent comprises a double-stranded RNA (dsRNA) comprising a sense strand and an antisense strand, each of the strands having 14 to 30 nucleotides, wherein the sense strand contains at least one motif of three 2'-F modifications on three consecutive nucleotides, one of said motifs occurring at or near the cleavage site in the sense strand; and wherein the antisense strand contains at least one motif of three 2'-O-methyl modifications on three consecutive nucleotides, one of said motifs occurring at or near the cleavage site in the antisense strand. In some embodiments, the sense strand comprises a sequence at least about 80%, 85%, 90%, 95%, or 100% identical to a sequence selected from SEQ ID NOS: 1-5184. In some embodiments, the antisense strand comprises a sequence at least about 80%, 85%, 90%, 95%, or 100% identical to the reverse complement of the sense strand. In some embodiments, the antisense strand comprises a sequence at least about 80%, 85%, 90%, 95%, or 100% identical to a sequence selected from SEQ ID NOS: 1-5184.

In another aspect, provided herein is a method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least 50% sequence identity to a reverse complement of a polynucleotide comprising 5 to 30 consecutive nucleotides within nucleotides 1 to 2610 of SEQ ID NO: 14923; thereby modulating a function of and/or the expression of the long-form thymic stromal lymphopoietin (1fTSLP) polynucleotide in patient cells or tissues, in vivo or in vitro. In some embodiments, at least one antisense oligonucleotide comprises SEQ ID NO: 14926. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561. In some embodiments, a function of and/or the expression of the long-form thymic stromal lymphopoietin (1fTSLP) is increased in vivo or in vitro with respect to a control oligonucleotide that does not target or specifically hybridize to 1fTSLP. In some embodiments, a function of and/or the expression of the long-form thymic stromal lymphopoietin (1fTSLP) is decreased in vivo or in vitro with respect to a control oligonucleotide that does not target or specifically hybridize to 1fTSLP. In some embodiments, the at least one anti sense oligonucleotide targets a natural antisense sequence of a long-form thymic stromal lymphopoietin (1fTSLP) polynucleotide. In some embodiments, the at least one antisense oligonucleotide targets a natural sense sequence of a long-form thymic stromal lymphopoietin (1fTSLP) polynucleotide. In some embodiments, the at least one antisense oligonucleotide targets a nucleic acid sequence comprising coding and/or non-coding nucleic acid sequences of a long-form thymic stromal lymphopoietin (1fTSLP) polynucleotide. In some embodiments, the at least one antisense oligonucleotide targets overlapping and/or non-overlapping sequences of a long-form thymic stromal lymphopoietin (1fTSLP) polynucleotide. In some embodiments, the at least one antisense oligonucleotide comprises one or more modifications. In some embodiments, the one or more modifications is selected from: at least one modified sugar moiety, at least one modified internucleoside linkage, at least one modified nucleotide, and combinations thereof. In some embodiments, the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof. In some embodiments, the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another aspect, provided herein is a method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide 5 to 30 nucleotides in length, wherein said antisense oligonucleotide has at least 50% sequence identity to an antisense oligonucleotide to the long-form thymic stromal lymphopoietin Off SLP) polynucleotide; thereby modulating a function of and/or the expression of the long-form thymic stromal lymphopoietin (1fTSLP) polynucleotide in patient cells or tissues, in vivo or in vitro. In some embodiments, at least one antisense oligonucleotide comprises SEQ ID NO: 14926. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561. In some embodiments, a function of and/or the expression of the long-form thymic stromal lymphopoietin (1fTSLP) is increased in vivo or in vitro with respect to a control oligonucleotide that does not target or specifically hybridize to 1fTSLP. In some embodiments, a function of and/or the expression of the long-form thymic stromal lymphopoietin (1fTSLP) is decreased in vivo or in vitro with respect to a control oligonucleotide that does not target or specifically hybridize to 1fTSLP. In some embodiments, the at least one antisense oligonucleotide targets a natural antisense sequence of a long-form thymic stromal lymphopoietin (1fTSLP) polynucleotide. In some embodiments, the at least one antisense oligonucleotide targets a natural sense sequence of a long-form thymic stromal lymphopoietin (1fTSLP) polynucleotide. In some embodiments, the at least one anti sense oligonucleotide targets a nucleic acid sequence comprising coding and/or non-coding nucleic acid sequences of a long-form thymic stromal lymphopoietin (1fTSLP) polynucleotide. In some embodiments, the at least one anti sense oligonucleotide targets overlapping and/or non-overlapping sequences of a long-form thymic stromal lymphopoietin (1fTSLP) polynucleotide. In some embodiments, the at least one anti sense oligonucleotide comprises one or more modifications. In some embodiments, the one or more modifications is selected from: at least one modified sugar moiety, at least one modified internucleoside linkage, at least one modified nucleotide, and combinations thereof. In some embodiments, the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof. In some embodiments, the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another aspect, provided herein is a method of modulating a function of and/or the expression of a long-form thymic stromal lymphopoietin Off SLP) polynucleotide in patient cells or tissues, in vivo or in vitro, the method comprising: contacting said cells or tissues with at least one anti sense oligonucleotide that targets a region of a natural antisense oligonucleotide of the long-form thymic stromal lymphopoietin (1fTSLP) polynucleotide; thereby modulating a function of and/or the expression of the long-form thymic stromal lymphopoietin (1fTSLP) polynucleotide in patient cells or tissues, in vivo or in vitro. In some embodiments, at least one antisense oligonucleotide comprises SEQ ID NO: 14926. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561. In some embodiments, a function of and/or the expression of the long-form thymic stromal lymphopoietin (1fTSLP) is increased in vivo or in vitro with respect to a control oligonucleotide that does not target or specifically hybridize to 1fTSLP. In some embodiments, a function of and/or the expression of the long-form thymic stromal lymphopoietin (1fTSLP) is decreased in vivo or in vitro with respect to a control oligonucleotide that does not target or specifically hybridize to 1fTSLP. In some embodiments, the at least one antisense oligonucleotide targets a natural antisense sequence of a long-form thymic stromal lymphopoietin (1fTSLP) polynucleotide. In some embodiments, the at least one antisense oligonucleotide targets a natural sense sequence of a long-form thymic stromal lymphopoietin (1fTSLP) polynucleotide. In some embodiments, the at least one anti sense oligonucleotide targets a nucleic acid sequence comprising coding and/or non-coding nucleic acid sequences of a long-form thymic stromal lymphopoietin (1fTSLP) polynucleotide. In some embodiments, the at least one anti sense oligonucleotide targets overlapping and/or non-overlapping sequences of a long-form thymic stromal lymphopoietin (1fTSLP) polynucleotide. In some embodiments, the at least one anti sense oligonucleotide comprises one or more modifications. In some embodiments, the one or more modifications is selected from: at least one modified sugar moiety, at least one modified internucleoside linkage, at least one modified nucleotide, and combinations thereof. In some embodiments, the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof. In some embodiments, the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another aspect, provided herein is a method of modulating a function of and/or the expression of a long-form thymic stromal lymphopoietin Off SLP) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least about 80%, 85%, 90%, 95%, or 100% sequence identity to a sequence selected from SEQ ID NOS: 9971-12561; thereby modulating a function of and/or the expression of the 1fTSLP polynucleotide in patient cells or tissues, in vivo or in vitro. In some embodiments, at least one antisense oligonucleotide comprises SEQ ID NO: 14926. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561. In some embodiments, a function of and/or the expression of the long-form thymic stromal lymphopoietin (1fTSLP) is increased in vivo or in vitro with respect to a control oligonucleotide that does not target or specifically hybridize to 1fTSLP. In some embodiments, a function of and/or the expression of the long-form thymic stromal lymphopoietin (1fTSLP) is decreased in vivo or in vitro with respect to a control oligonucleotide that does not target or specifically hybridize to 1fTSLP. In some embodiments, the at least one antisense oligonucleotide targets a natural antisense sequence of a long-form thymic stromal lymphopoietin (1fTSLP) polynucleotide. In some embodiments, the at least one antisense oligonucleotide targets a natural sense sequence of a long-form thymic stromal lymphopoietin (1fTSLP) polynucleotide. In some embodiments, the at least one antisense oligonucleotide targets a nucleic acid sequence comprising coding and/or non-coding nucleic acid sequences of a long-form thymic stromal lymphopoietin (1fTSLP) polynucleotide. In some embodiments, the at least one antisense oligonucleotide targets overlapping and/or non-overlapping sequences of a long-form thymic stromal lymphopoietin (1fTSLP) polynucleotide. In some embodiments, the at least one antisense oligonucleotide comprises one or more modifications. In some embodiments, the one or more modifications is selected from: at least one modified sugar moiety, at least one modified internucleoside linkage, at least one modified nucleotide, and combinations thereof. In some embodiments, the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof. In some embodiments, the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another aspect, provided herein is a method of modulating a function of and/or the expression of a long-form thymic stromal lymphopoietin (1fTSLP) gene in mammalian cells or tissues, in vivo or in vitro, the method comprising: contacting said cells or tissues with at least one short interfering RNA (siRNA) oligonucleotide 5 to 30 nucleotides in length, said at least one siRNA oligonucleotide being specific for an antisense polynucleotide of a long-form thymic stromal lymphopoietin (1fTSLP) polynucleotide, wherein said at least one siRNA oligonucleotide has at least 50% sequence identity to a complementary sequence of at least about five consecutive nucleic acids of the antisense and/or sense nucleic acid molecule of the long-form thymic stromal lymphopoietin (1fTSLP) polynucleotide; thereby modulating a function of and or the expression of long-form thymic stromal lymphopoietin, (1fTSLP) in mammalian cells or tissues in vivo or in vitro. In some embodiments, said oligonucleotide has at least 80% sequence identity to a sequence of at least about five consecutive nucleic acids that is complementary to the antisense and/or sense nucleic acid molecule of the long-form thymic stromal lymphopoietin (1fTSLP) polynucleotide. In some embodiments, the at least one siRNA oligonucleotide comprises a sequence selected from SEQ ID NOS: 1-5184. In some embodiments, the at least one siRNA oligonucleotide comprises a sequence at least about 80%, 85%, 90%, 95%, or 100% identical to a sequence selected from SEQ ID NOS: 1-5184.

In another aspect, provided herein is a method of modulating a function of and/or the expression of long-form thymic stromal lymphopoietin, (1fTSLP) in mammalian cells or tissues, in vivo or in vitro, the method comprising: contacting said cells or tissues with at least one antisense oligonucleotide of about 5 to 30 nucleotides in length, the antisense oligonucleotide specific for noncoding and/or coding sequences of a sense and/or natural antisense strand of a long-form thymic stromal lymphopoietin (1fTSLP) polynucleotide, wherein said at least one antisense oligonucleotide has at least 50% sequence identity to at least one nucleic acid sequence set forth as 1 to 2610 of SEQ ID NO: 14923 or its complement; thereby modulating the function and/or expression of the long-form thymic stromal lymphopoietin (1fTSLP) in mammalian cells or tissues, in vivo or in vitro. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561.

In another aspect, provided herein is a synthetic, modified oligonucleotide comprising at least one modification wherein the at least one modification is selected from: at least one modified sugar moiety; at least one modified intenucleotide linkage; at least one modified nucleotide, and combinations thereof; wherein said oligonucleotide is an antisense compound which hybridizes to and modulates the function and/or expression of a long-form thymic stromal lymphopoietin (1fTSLP) polynucleotide in vivo or in vitro as compared to a control oligonucleotide that does not specifically hybridize to the 1fTSLP polynucleotide. In some embodiments, the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof. In some embodiments, said oligonucleotide comprises at least one phosphorothioate internucleotide linkage. In some embodiments, said oligonucleotide comprises a backbone of phosphorothioate internucleotide linkages. In some embodiments, the oligonucleotide comprises at least one modified nucleotide, said modified nucleotide selected from: a peptide nucleic acid, a locked nucleic acid (LNA), and an analogue, derivative, and a combination thereof. In some embodiments, the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof. In some embodiments, the oligonucleotide comprises a plurality of modifications, wherein said modifications comprise modified nucleotides selected from: peptide nucleic acids, locked nucleic acids (LNA), and analogues, derivatives, and a combination thereof. In some embodiments, the oligonucleotide comprises at least one modified sugar moiety selected from: a 2'-O-methoxyethyl modified sugar moiety, a 2'-methoxy modified sugar moiety, a 2-O-alkyl modified sugar moiety, a bicyclic sugar moiety, and a combination thereof. In some embodiments, the oligonucleotide comprises a plurality of modifications, wherein said modifications comprise modified sugar moieties selected from: a 2'-O-methoxyethyl modified sugar moiety, a 2-methoxy modified sugar moiety, a 2'-O-alkyl modified sugar moiety, a bicyclic sugar moiety, and a combination thereof. In some embodiments, the oligonucleotide is of at least about 5 to 30 nucleotides in length and hybridizes to an antisense and/or sense strand of a long-form thymic stromal lymphopoietin Off SLP) polynucleotide, wherein said oligonucleotide has at least about 20% sequence identity to a complementary sequence of at least about five consecutive nucleic acids of the antisense and/or sense coding and/or noncoding nucleic acid sequences of the long-form thymic stromal lymphopoietin (1fTSLP) polynucleotide. In some embodiments, the oligonucleotide has at least about 80% sequence identity to a complementary sequence of at least about five consecutive nucleic acids of the antisense and or sense coding and/or noncoding nucleic acid sequence of the long-form thymic stromal lymphopoietin (1fTSLP) polynucleotide. In some embodiments, said oligonucleotide hybridizes to and modulates expression and/or function of at least one long-form thymic stromal lymphopoietin (1fTSLP) polynucleotide, in vivo or in vitro, as compared to the control oligonucleotide. In some embodiments, the oligonucleotide comprises the sequence set forth as SEQ ID NO: 14926. In some embodiments, the at least one antisense oligonucleotide comprises a sequence selected from SEQ ID NOS: 9971-12561. In some embodiments, the at least one antisense oligonucleotide comprises a sequence at least about 80%, 85%, 90%, 95%, or 100% identical to a sequence selected from SEQ ID NOS: 9971-12561.

In another aspect, provided herein is a composition comprising one or more oligonucleotides specific for one or more long-form thymic stromal lymphopoietin (1fTSLP) polynucleotides, said one or more oligonucleotides comprising an antisense sequence, complementary sequence, allele, homolog, isoform, variant, derivative, mutant, or fragment of the 1fTSLP polynucleotide, or a combination thereof. In some embodiments, the one or more oligonucleotides have at least about 40% sequence identity as compared to the nucleotide sequence set forth as SEQ ID NO: 14926. In some embodiments, the oligonucleotide comprises the nucleotide sequence set forth as SEQ ID NO: 14926. In some embodiments, the one or more oligonucleotides comprises a sequence selected from SEQ ID NOS: 1-14922. In some embodiments, the one or more oligonucleotides comprises a sequence at least about 80%, 85%, 90%, 95%, or 100% identical to a sequence selected from SEQ ID NOS: 1-14922. In some embodiments, the one or more oligonucleotides comprises one or more modifications or substitutions. In some embodiments, the one or more modifications are selected from: phosphorothioate, methylphosphonate, peptide nucleic acid, locked nucleic acid (LNA) molecules, and combinations thereof.

In another aspect, provided herein is a method of preventing or treating a disease associated with at least one long-form thymic stromal lymphopoietin (1fTSLP) polynucleotide and/or at least one encoded product thereof, the method comprising: administering to a subject in need thereof a therapeutically effective dose of at least one antisense oligonucleotide that binds to a natural antisense sequence of said at least one long-form thymic stromal lymphopoietin (1fTSLP) polynucleotide and modulates expression of said at least one long-form thymic stromal lymphopoietin (1fTSLP) polynucleotide; thereby preventing or treating the disease associated with the at least one long-form thymic stromal lymphopoietin (1fTSLP) polynucleotide and or at least one encoded product thereof. In some embodiments, a disease associated with the at least one long-form thymic stromal lymphopoietin (1fTSLP) polynucleotide is selected from: a disease or disorder associated with abnormal function and/or expression of 1fTSLP, inflammation of the nasal passageways, inflammation of the lower airway, a proliferative skin disease or disorder, ichthyosis, a disease or disorder associated with impaired epidermal lipid barrier, a disease or disorder associated with impaired adipocyte differentiation, a disease or disorder associated with impaired keratinocyte differentiation, an inflammatory skin disease or disorder, a cardiovascular disease or disorder, a coronary disease or disorder, myocardial infarction, cancer, glandular neoplasm, epithelial neoplasm, ovarian neoplasm, breast neoplasm, stroke and brain ischemia. In some embodiments, the proliferative skin disease or disorder comprises psoriasis, chronic proliferative dermatitis, atopic dermatitis, or a combination thereof. In some embodiments, the ichthyosis comprises autosomal recessive congenital ichthyosis (ARCI), collodion baby syndrome, nonbullous congenital ichthyosiform eiythroderma, lamellar ichthyosis, or a combination thereof. In some embodiments, the cancer is selected from lung cancer, epidermoid carcinoma, breast cancer, or a combination thereof.

In another aspect, provided herein is a method of preventing or treating a disease associated with at least one long-form thymic stromal lymphopoietin (1fTSLP) polynucleotide and/or at least one encoded product thereof, the method comprising: administering to a subject in need thereof a therapeutically effective dose of at least one anti sense oligonucleotide that binds to a natural sense sequence of said at least one long-form thymic stromal lymphopoietin (1fTSLP) polynucleotide and modulates expression of said at least one long-form thymic stromal lymphopoietin (1fTSLP) polynucleotide; thereby preventing or treating the disease associated with the at least one long-form thymic stromal lymphopoietin (1fTSLP) polynucleotide and or at least one encoded product thereof. In some embodiments, a disease associated with the at least one long-form thymic stromal lymphopoietin (1fTSLP) polynucleotide is selected from: a disease or disorder associated with abnormal function and/or expression of 1fTSLP, inflammation of the nasal passageways, inflammation of the lower airway, a proliferative skin disease or disorder, ichthyosis, a disease or disorder associated with impaired epidermal lipid barrier, a disease or disorder associated with impaired adipocyte differentiation, a disease or disorder associated with impaired keratinocyte differentiation, an inflammatory skin disease or disorder, a cardiovascular disease or disorder, a coronary disease or disorder, myocardial infarction, cancer, glandular neoplasm, epithelial neoplasm, ovarian neoplasm, breast neoplasm, stroke and brain ischemia. In some embodiments, the proliferative skin disease or disorder comprises psoriasis, chronic proliferative dermatitis, atopic dermatitis, or a combination thereof. In some embodiments, the ichthyosis comprises autosomal recessive congenital ichthyosis (ARCI), collodion baby syndrome, nonbullous congenital ichthyosiform eiythroderma, lamellar ichthyosis, or a combination thereof. In some embodiments, the cancer is selected from lung cancer, epidermoid carcinoma, breast cancer, or a combination thereof.

In another aspect, provided herein is a method of identifying and selecting at least one oligonucleotide for in vivo administration comprising: identifying at least one oligonucleotide comprising at least five consecutive nucleotides which are complementary to 1fTSLP or to a polynucleotide that is antisense to 1fTSLP; measuring the thermal melting point of a hybrid of an antisense oligonucleotide and the 1fTSLP or the polynucleotide that is antisense to the 1fTSLP under stringent hybridization conditions; and selecting at least one oligonucleotide for in vivo administration based on the information obtained.

In another aspect, provided herein is a method of treating a disease or condition mediated by TSLP, the method comprising administering to a subject in need thereof an oligonucleotide comprising a sequence at least about 80%, 85%, 90%, 95%, or 100% identical to a sequence selected from SEQ ID NOS: 1-14922. In some embodiments, the oligonucleotide comprises a sequence selected from SEQ ID NOS: 1-14922. In some embodiments, the TSLP is 1fTSLP. In some embodiments, the disease or condition comprises allergic rhinitis (AR), non-allergic rhinitis (NAR), chronic rhinosinusitis (CRS), asthma, COPD and asthma-COPD overlap syndrome (ACOS), or a combination thereof. In some embodiments, the oligonucleotide comprises dsRNA. In some embodiments, the oligonucleotide comprises a sequence at least about 80%, 85%, 90%, 95%, or 100% identical to a sequence selected from SEQ ID NOS: 1-9970. In some embodiments, the oligonucleotide comprises a sequence at least about 80%, 85%, 90%, 95%, or 100% identical to a sequence selected from SEQ ID NOS: 1-5184. In some embodiments, the oligonucleotide comprises a sequence at least about 80%, 85%, 90%, 95%, or 100% identical to a sequence selected from SEQ ID NOS: 9971-14922. In some embodiments, the oligonucleotide comprises a sequence at least about 80%, 85%, 90%, 95%, or 100% identical to a sequence selected from SEQ ID NOS: 9971-12561.

DETAILED DESCRIPTION

Figure 1:
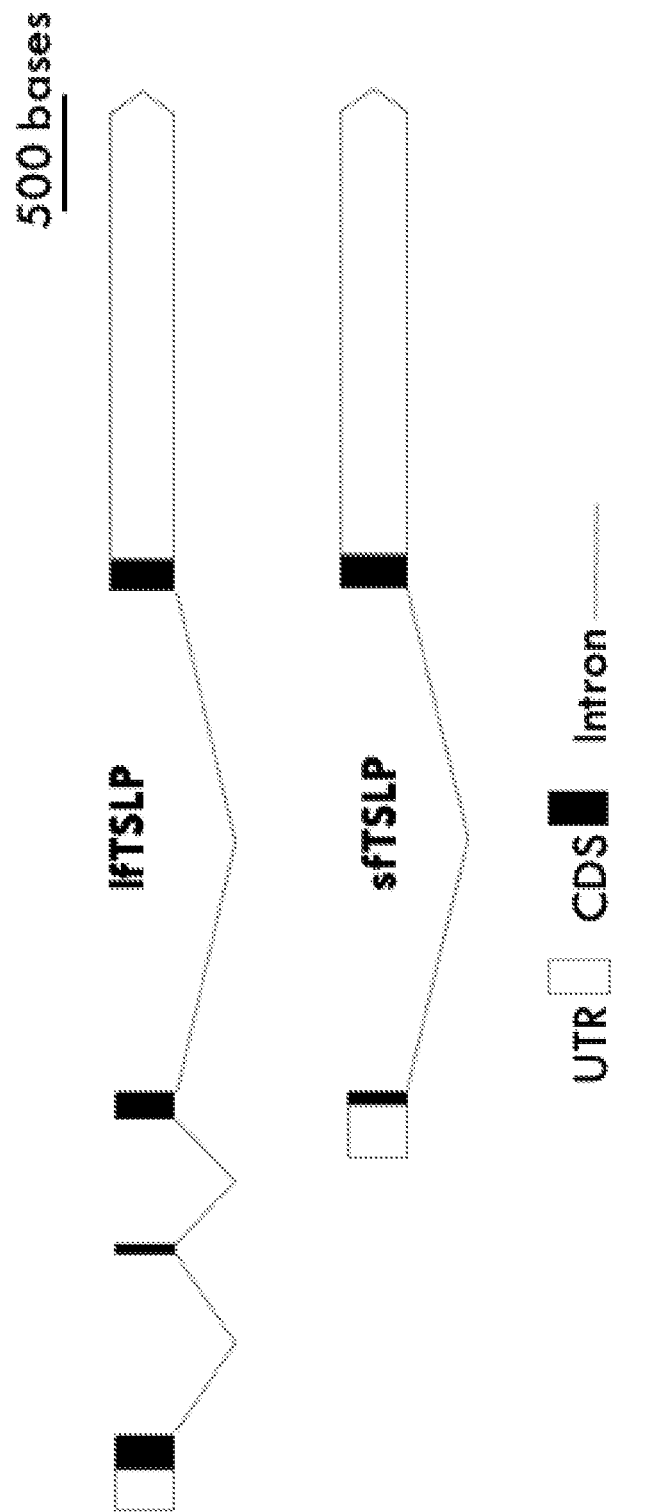
FIG. 1 is a schematic of the two isoforms of TSLP: 1fTSLP and sfTSLP.

Disclosed herein are compositions comprising an oligonucleotide that targets Thymic stromal lymphopoietin (TSLP). The oligonucleotide may include a small interfering RNA (siRNA) or an antisense oligonucleotide (ASO). Also provided herein are methods of treating an airway disorder by providing an oligonucleotide that targets TSLP to a subject in need thereof.

Definitions

The terminology used herein is for the purpose of describing particular embodiments only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, and up to 1% of a given value. Alternatively, particularly with respect to biological systems or processes, the term can mean within an order of magnitude, e.g., within 5-fold, or within 2-fold, of a value. Where particular values are described in the application and claims, unless otherwise stated the term "about" meaning within an acceptable error range for the particular value should be assumed.

In some embodiments, the term "mRNA" means the presently known mRNA transcript(s) of a targeted gene, and any further transcripts which may be elucidated.

In some embodiments, "dsRNA", "siRNA", and "iRNA agent" are used interchangeably as agents that can mediate silencing of a target RNA, e.g., mRNA, e.g., a transcript of a gene that encodes a protein. In some cases, the target RNA is TSLP or 1fTSLP. Such mRNA may also be referred to herein as mRNA to be silenced. Such a gene is also referred to as a target gene. In some cases, the RNA to be silenced is an endogenous gene or a pathogen gene. In addition, RNAs other than mRNA, e.g., tRNAs, and viral RNAs, can also be targeted.

In some embodiments, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent.

In some embodiments, "specifically hybridizable" and "complementary" are terms which are used to indicate a sufficient degree of complementarity such that stable and specific binding occurs between a compound described herein and a target RNA molecule.

Specific binding may require a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences may differ by at least 5 nucleotides.

In some embodiments, a dsRNA agent of the invention is "sufficiently complementary" to a target RNA, e.g., a target mRNA, such that the dsRNA agent silences production of protein encoded by the target mRNA. In some embodiments, the dsRNA agent of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent of the invention specifically discriminates a single-nucleotide difference. In this case, the dsRNA agent only mediates RNAi if exact complementary is found in the region (e.g., within 7 nucleotides of) the single-nucleotide difference.

In some embodiments, the term "oligonucleotide" refers to a nucleic acid molecule (RNA or DNA) for example of length less than 100, 200, 300, or 400 nucleotides. Some embodiments relate to an oligonucleotide or nucleic acid sequence comprising one or more uracil nucleobases. In some embodiments, one or more of the uracil nucleobases may be substituted for one or more thymine nucleobases. Some embodiments relate to an oligonucleotide or nucleic acid sequence comprising one or more thymine nucleobases. In some embodiments, one or more of the thymine nucleobases may be substituted for one or more uracil nucleobases.

In some embodiments, "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA and DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In some embodiments, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

In some embodiments, the oligonucleotide is "chimeric", that is, composed of different regions. "Chimeric" oligonucleotides contain two or more chemical regions, for example, DNA region(s), RNA region(s), PNA region(s), etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. Chimeric oligonucleotides can be formed as mixed structures of two or more oligonucleotides, modified oligonucleotides, oligonucleosides and/or oligonucleotide analogs.

The oligonucleotide can be composed of regions that can be linked in "register", that is, when the monomers are linked consecutively, as in native DNA, or linked via spacers. The spacers are intended to constitute a covalent "bridge" between the regions and have, in some cases, a length not exceeding about 100 carbon atoms. The spacers may carry different functionalities, for example, having positive or negative charge, carry special nucleic acid binding properties (intercalators, groove binders, toxins, fluorophores etc.), being lipophilic, inducing special secondary structures like, for example, alanine containing peptides that induce alpha-helices.

In some embodiments, "1fTSLP" and "long-form thymic stromal lymphopoietin" are inclusive of all family members, mutants, alleles, fragments, species, coding and noncoding sequences, sense and antisense polynucleotide strands, etc. of the TSLP transcript variant 1 (NM_033035.5; SEQ ID NO: 14923). In some embodiments, "1fTSLP" and "long-form thymic stromal lymphopoietin" are used interchangeably in the present application.

In some embodiments, "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays.

In some embodiments, the term "target nucleic acid" encompasses DNA, RNA (including pre-mRNA and mRNA) transcribed from such DNA, and also cDNA derived from such RNA, coding, noncoding sequences, sense and antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA that are modulated include, for example, replication and transcription. The functions of RNA that are modulated, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs can be synthesized and used according to procedures that are well known in the art and that will be familiar to the ordinarily skilled artisan. Small interfering RNAs for use in the methods herein suitably comprise between about 1 to about 50 nucleotides (nt). In examples of non-limiting embodiments, siRNAs can comprise about 5 to about 40 nt, about 5 to about 30 nt, about 10 to about 30 nt, about 15 to about 25 nt, or about 20-25 nucleotides.

In some embodiments, selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes.

In some embodiments, "enzymatic RNA" is meant an RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

In some embodiments, "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and some embodiments can be readily generated using techniques generally known in the art.

In some embodiments, "monomers" typically indicates monomers linked by phosphodiester bonds or analogs thereof to form oligonucleotides ranging in size from a few monomelic units, e.g., from about 3-4, to about several hundreds of monomelic units. Analogs of phosphodiester linkages include: phosphorothioate, phosphorodithioate, methylphosphornates, phosphoroselenoate, phosphoramidate, and the like, as more fully described below.

In some embodiments, "nucleotide" covers naturally occurring nucleotides as well as non-naturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, ^aminopurine, 8-oxo-N6-memyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-memyl-4-triazolopyridin, isocytosine, isoguanin, inosine and the "non-naturally occurring" nucleotides described in Benner et al, U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, as well as their analogs.

In some embodiments, "analogs" in reference to nucleotides includes synthetic nucleotides having modified base moieties and/or modified sugar moieties. Such analogs include synthetic nucleotides designed to enhance binding properties, e.g., duplex or triplex stability, specificity, or the like.

In some embodiments, "hybridization" means the pairing of at least substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

In some embodiments, an antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In some embodiments, "stringent hybridization conditions" or "stringent conditions" refers to conditions under which a compound will hybridize to its target sequence, but to a minimal number of other sequences. Stringent conditions are sequence-dependent and will be different in different circumstances and "stringent conditions" under which oligomeric compounds hybridize to a target sequence are determined by the nature and composition of the oligomeric compounds and the assays in which they are being investigated. In some cases, stringent hybridization conditions comprise low concentrations (<0.15M) of salts with inorganic cations such as Na+ or K+ (i.e., low ionic strength), temperature higher than about 20° C. to 25° C. and below the Tm of the oligomeric compound/target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

In some embodiments, "complementary" refers to the capacity for precise pairing between two nucleotides on one or two oligomeric strands. For example, if a nucleobase at a certain position of an anti sense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid may be considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which may be used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). In some embodiments, oligomeric compounds disclosed herein comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present disclosure. Percent complementarity of an antisense compound with a region of a target nucleic acid can be determined routinely using BLAST programs (basic local alignment search tools) and Power-BLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman.

In some embodiments, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

In some embodiments, "modulation" means either an increase (stimulation) or a decrease (inhibition) in the expression of a gene.

In some embodiments, the term "variant", when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, co factors, inhibitors, magnetic particles, and the like.

In some embodiments, a "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" includes the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.). The term "treatment" is intended to encompass also prophylaxis, therapy and cure. The patient receiving this treatment is any animal in need, including primates, in particular humans, and other mammals such as equines, cattle, swine and sheep; and poultry and pets in general.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In some embodiments, the genes or nucleic acid sequences are human.

In some embodiments, the term "halo" refers to any radical of fluorine, chlorine, bromine or iodine. In some embodiments, the term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, Ci-Cio indicates that the group may have from 1 to 10 (inclusive) carbon atoms in it. The term "alkoxy" refers to an —O-alkyl radical. In some embodiments, the term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. In some embodiments, the term "mercapto" refers to an —SH radical. The term "thioalkoxy" refers to an —S-alkyl radical.

In some embodiments, the term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. In some embodiments, the term "arylalkyl" or the term "aralkyl" refers to alkyl substituted with an aryl. In some embodiments, the term "arylalkoxy" refers to an alkoxy substituted with aryl.

In some embodiments, the term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

In some embodiments, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. In some embodiments, the term "heteroarylalkyl" or the term "heteroaralkyl" refers to an alkyl substituted with a heteroaryl. In some embodiments, the term "heteroarylalkoxy" refers to an alkoxy substituted with heteroaryl.

In some embodiments, the term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

In some embodiments, the term "oxo" refers to an oxygen atom, which forms a carbonyl when attached to carbon, an N-oxide when attached to nitrogen, and a sulfoxide or sulfone when attached to sulfur.

In some embodiments, the term "acyl" refers to an alkylcarbonyl, cycloalkylcarbonyl, arylcarbonyl, heterocyclylcarbonyl, or heteroarylcarbonyl substituent, any of which may be further substituted by substituents.

In some embodiments, the term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylamino carbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Oligonucleotide Compounds and Compositions

In some embodiments, provided herein are oligonucleotide compounds that target a nucleic acid sequence of long-form thymic stromal lymphopoietin (1fTSLP), including, without limitation, sense and/or anti sense noncoding and/or coding sequences associated with 1fTSLP. In some embodiments, the target nucleic acid molecule is not limited to 1fTSLP polynucleotides alone but extends to any of the isoforms, receptors, homologs, non-coding regions and the like of 1fTSLP.

In some embodiments, provided is a composition comprising one or more antisense oligonucleotides or dsRNA agents targeted to a first nucleic acid and one or more additional antisense compounds targeted to a second nucleic acid target. For example, the first target may be a particular sequence of long-form thymic stromal lymphopoietin (1fTSLP), and the second target may be a region from another nucleotide sequence. Alternatively, compositions of the invention may contain two or more antisense oligonucleotide or dsRNA compounds targeted to different regions of the same 1fTSLP nucleic acid target. Numerous examples of antisense oligonucleotide or dsRNA compounds are illustrated herein and others may be selected from among suitable compounds known in the art. Two or more combined compounds may be used together or sequentially.

In some embodiments, a composition is provided that includes a plurality of antisense oligonucleotide or dsRNA agent species. In some embodiments, the antisense oligonucleotide or dsRNA agent species has sequences that are non-overlapping and non-adjacent to another species with respect to a naturally occurring target sequence. In some embodiments, the plurality of antisense oligonucleotide or dsRNA agent species is specific for different naturally occurring target genes. In some embodiments, the dsRNA agent is allele specific.

The disclosure provides methods, compositions, and kits, for administration and delivery of antisense oligonucleotide or dsRNA agents described herein.

Disclosed herein, in some embodiments, is are compositions comprising an oligonucleotide that targets a long isoform of Thymic stromal lymphopoietin (1fTSLP) and when administered to a subject in an effective amount decreases an eosinophil count. In some embodiments, the eosinophil count is decreased by about 2.5% or more, about 5% or more, or about 7.5% or more. In some embodiments, the eosinophil count is decreased by about 10% or more. In some embodiments, the eosinophil count is decreased by about 20% or more, about 30% or more, about 40% or more, about 50% or more, about 60% or more, about 70% or more, about 80% or more, about 90% or more, or about 100% or more. In some embodiments, the eosinophil count is decreased by about 200% or more, about 300% or more, about 400% or more, about 500% or more, about 600% or more, about 700% or more, about 800% or more, about 900% or more, or about 1000% or more. In some embodiments, the eosinophil count is decreased by no more than about 2.5%, no more than about 5%, or no more than about 7.5%. In some embodiments, the eosinophil count is decreased by no more than about 10%. In some embodiments, the eosinophil count is decreased by no more than about 20%, no more than about 30%, no more than about 40%, no more than about 50%, no more than about 60%, no more than about 70%, no more than about 80%, no more than about 90%, or no more than about 100%. In some embodiments, the eosinophil count is decreased by no more than about 200%, no more than about 300%, no more than about 400%, no more than about 500%, no more than about 600%, no more than about 700%, no more than about 800%, no more than about 900%, or no more than about 1000%. In some embodiments, the eosinophil count is decreased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some aspects, the composition comprises an oligonucleotide that targets 1fTSLP and when administered to a subject in an effective amount decreases an inflammatory marker. In some embodiments, the inflammatory marker is decreased by about 2.5% or more, about 5% or more, or about 7.5% or more. In some embodiments, the inflammatory marker is decreased by about 10% or more. In some embodiments, the inflammatory marker is decreased by about 20% or more, about 30% or more, about 40% or more, about 50% or more, about 60% or more, about 70% or more, about 80% or more, about 90% or more, or about 100% or more. In some embodiments, the inflammatory marker is decreased by about 200% or more, about 300% or more, about 400% or more, about 500% or more, about 600% or more, about 700% or more, about 800% or more, about 900% or more, or about 1000% or more. In some embodiments, the inflammatory marker is decreased by no more than about 2.5%, no more than about 5%, or no more than about 7.5%. In some embodiments, the inflammatory marker is decreased by no more than about 10%. In some embodiments, the inflammatory marker is decreased by no more than about 20%, no more than about 30%, no more than about 40%, no more than about 50%, no more than about 60%, no more than about 70%, no more than about 80%, no more than about 90%, or no more than about 100%. In some embodiments, the inflammatory marker is decreased by no more than about 200%, no more than about 300%, no more than about 400%, no more than about 500%, no more than about 600%, no more than about 700%, no more than about 800%, no more than about 900%, or no more than about 1000%. In some embodiments, the inflammatory marker is decreased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some aspects, the composition comprises an oligonucleotide that targets 1fTSLP and when administered to a subject in an effective amount decreases mucus production. In some embodiments, the mucus production is decreased by about 2.5% or more, about 5% or more, or about 7.5% or more. In some embodiments, the mucus production is decreased by about 10% or more. In some embodiments, the mucus production is decreased by about 20% or more, about 30% or more, about 40% or more, about 50% or more, about 60% or more, about 70% or more, about 80% or more, about 90% or more, or about 100% or more. In some embodiments, the mucus production is decreased by about 200% or more, about 300% or more, about 400% or more, about 500% or more, about 600% or more, about 700% or more, about 800% or more, about 900% or more, or about 1000% or more. In some embodiments, the mucus production is decreased by no more than about 2.5%, no more than about 5%, or no more than about 7.5%. In some embodiments, the mucus production is decreased by no more than about 10%. In some embodiments, the mucus production is decreased by no more than about 20%, no more than about 30%, no more than about 40%, no more than about 50%, no more than about 60%, no more than about 70%, no more than about 80%, no more than about 90%, or no more than about 100%. In some embodiments, the mucus production is decreased by no more than about 200%, no more than about 300%, no more than about 400%, no more than about 500%, no more than about 600%, no more than about 700%, no more than about 800%, no more than about 900%, or no more than about 1000%. In some embodiments, the mucus production is decreased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the 1fTSLP is encoded by a nucleic acid comprising SEQ ID NO: 14923, or a variant thereof at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical, to SEQ ID NO: 14923. In some embodiments, the 1fTSLP is encoded by a nucleic acid comprising SEQ ID NO: 14923.

In some embodiments, the oligonucleotide is specific for 1fTSLP, and/or does not target a short isoform of TSLP (sfTSLP). In some embodiments, the oligonucleotide is specific for sfTSLP, and/or does not target a long form of TSLP (1fTSLP). In some embodiments, the oligonucleotide targets both sfTSLP and 1fTSLP.

In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. In some embodiments, the oligonucleotide comprises no more than 18 modified internucleoside linkages. In some embodiments, the oligonucleotide comprises no more than 20 modified internucleoside linkages. In some embodiments, the oligonucleotide comprises 1, 2, 3, 4, 5, 6, 7, 8, 9, 10, 11, 12, 13, 14, 15, 16, 17, 18, 19, or 20 modified internucleoside linkages, or a range of modified internucleoside linkages defined by any two of the aforementioned numbers. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

In some embodiments, the oligonucleotide comprises a modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof. In some embodiments, the modified nucleoside comprises an LNA. In some embodiments, the modified nucleoside comprises a 2',4' constrained ethyl nucleic acid. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises one or more 2'fluoro modified nucleosides. In some embodiments, the modified nucleoside comprises a 2' O-alkyl modified nucleoside.

In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof.

In some embodiments, the oligonucleotide comprises 1, 2, 3, 4, 5, 6, 7, 8, 9, 10, 11, 12, 13, 14, 15, 16, 17, 18, 19, 20, or 21 modified nucleosides, or a range of nucleosides defined by any two of the aforementioned numbers. In some embodiments, the oligonucleotide comprises no more than 19 modified nucleosides. In some embodiments, the oligonucleotide comprises no more than 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

dsRNA Agent

In one aspect, provided herein is a double-stranded RNAi (dsRNA) agent capable of inhibiting the expression of 1fTSLP. The dsRNA agent comprises a sense strand and an antisense strand. In some cases, the sense strand comprises a sequence at least about 80%, 85%, 90%, 95%, or 100% identical to a sequence selected from SEQ ID NOS: 1-5184. In some cases, the antisense strand comprises a sequence at least about 80%, 85%, 90%, 95%, or 100% identical to the reverse complement of the sense strand. In some cases, the antisense strand comprises a sequence at least about 80%, 85%, 90%, 95%, or 100% identical to a sequence selected from SEQ ID NOS: 1-5184.

In one aspect, provided herein is a double-stranded RNAi (dsRNA) agent capable of inhibiting the expression of sfTSLP. The dsRNA agent comprises a sense strand and an antisense strand. In some cases, the sense strand comprises a sequence at least about 80%, 85%, 90%, 95%, or 100% identical to a sequence selected from SEQ ID NOS: 5185-9970. In some cases, the antisense strand comprises a sequence at least about 80%, 85%, 90%, 95%, or 100% identical to the reverse complement of the sense strand. In some cases, the antisense strand comprises a sequence at least about 80%, 85%, 90%, 95%, or 100% identical to a sequence selected from SEQ ID NOS: 5185-9970.

In some cases, each strand of the dsRNA agent can range from 12-30 nucleotides in length. For example, each strand can be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and anti sense strand typically form a duplex dsRNA. The duplex region of a dsRNA agent may be 12-30 nucleotide pairs in length. For example, the duplex region can be between 14-30 nucleotide pairs in length, 17-30 nucleotide pairs in length, 25-30 nucleotides in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region has a length of about 15, 16, 17, 18, 19, 20, 21, 22, 23, 24, 25, 26, and 27.

In some embodiments, the dsRNA agent comprises one or more overhang regions and/or capping groups at the 3'-end, or 5'-end, or both ends of a strand. In some cases, the overhang is about 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhang can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

dsRNA Modifications

The modifications described herein in reference to dsRNA agents may be applicable to antisense oligonucleotides described elsewhere herein.

In some embodiments, one or more nucleotides in the sense and/or antisense strand of a dsRNA agent is modified. In some cases, every nucleotide in the sense strand and antisense strand of the dsRNA has been modified. The modifications on sense strand and antisense strand may each independently comprises at least two different modifications. In some cases, not every nucleotide in the sense and antisense strand is modified. In some cases, no nucleotide in the sense and/or antisense strand is modified. In some embodiments, the sense strand of the dsRNA agent comprises a modification pattern as described herein. In some embodiments, the antisense strand of the dsRNA agent comprises a modification pattern as described herein.

In some cases, the sense strand contains at least one motif of three identical modifications on three consecutive nucleotides, where at least one of the motifs occurs at or near the cleavage site in the antisense strand. In some cases, the antisense strand contains at least one motif of three identical modifications on three consecutive nucleotides. The modification pattern of the antisense strand may be shifted by one or more nucleotides relative to the modification pattern of the sense strand.

In some cases, the sense strand contains at least two motifs of three identical modifications on three consecutive nucleotides, when at least one of the motifs occurs at the cleavage site in the strand and at least one of the motifs occurs at another portion of the strand that is separated from the motif at the cleavage site by at least one nucleotide. In some cases, the antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide.

In some cases, the sense strand contains at least two motifs of three identical modifications on three consecutive nucleotides, where at least one of the motifs occurs at the cleavage site in the strand and at least one of the motifs occurs at another portion of the strand that is separated from the motif at the cleavage site by at least one nucleotide. In some cases, the antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide. In some cases, the modification in the motif occurring at the cleavage site in the sense strand is different than the modification in the motif occurring at or near the cleavage site in the antisense strand.

In some cases, the sense strand contains at least one motif of three 2'-F modifications on three consecutive nucleotides, where at least one of the motifs occurs at the cleavage site in the strand. In some cases, the antisense strand contains at least one motif of three 2'-O-methyl modifications on three consecutive nucleotides.

In some cases, the sense strand comprises one or more motifs of three identical modifications on three consecutive nucleotides, where the one or more additional motifs occur at another portion of the strand that is separated from the three 2'-F modifications at the cleavage site by at least one nucleotide. The antisense strand may comprise one or more motifs of three identical modifications on three consecutive nucleotides, where the one or more additional motifs occur at another portion of the strand that is separated from the three 2'-O-methyl modifications by at least one nucleotide. In some cases at least one of the nucleotides having a 2'-F modification may form a base pair with one of the nucleotides having a 2'-O-methyl modification.

In some embodiments, if the dsRNA agent comprises an overhang, the nucleotides in the overhang region of the dsRNA agent can each independently be a modified or unmodified nucleotide. Non-limiting examples of modifications include, but are not limited to, a 2'-sugar modification, such as, 2-F 2'-Omethyl, thymidine (T), 2'-O-methoxyethyl-5-methyluridine (Teo), 2'-O-methoxyethyl adenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

In some embodiments, if the dsRNA agent comprises an overhang, the 5'- and/or 3'-overhang at the sense strand, antisense strand or both strands of the dsRNA agent may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

In some embodiments, the modified dsRNA agent comprises one or more modified nucleotides including, but not limited to, 2'OMe nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, or combinations thereof. In some embodiments, the modified dsRNA agent comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, or combinations thereof. In certain instances, the modified dsRNA agent does not comprise 2'OMe-cytosine nucleotides. In some embodiments, the modified dsRNA agent comprises a hairpin loop structure.

In certain aspects, the modified dsRNA agent has an IC50 less than or equal to ten-fold that of the corresponding unmodified dsRNA (e.g., the modified dsRNA agent has an IC50 that is less than or equal to ten-times the IC50 of the corresponding unmodified dsRNA agent). In some embodiments, the modified dsRNA agent has an IC50 less than or equal to three-fold that of the corresponding unmodified dsRNA agent. In some embodiments, the modified dsRNA agent has an IC50 less than or equal to two-fold that of the corresponding unmodified dsRNA agent. It will be readily apparent to those of skill in the art that a dose response curve can be generated and the IC50 values for the modified dsRNA agent and the corresponding unmodified dsRNA agent can be readily determined using methods known to those of skill in the art.

The modified dsRNA agent may have 3' overhangs of one, two, three, four, or more nucleotides on one or both sides of the double-stranded region, or may lack overhangs (i.e., have blunt ends). In some cases, the modified dsRNA agent has 3' overhangs of two nucleotides on each side of the double-stranded region. In certain instances, the 3' overhang on the antisense strand has complementarity to the target sequence and the 3' overhang on the sense strand has complementarity to the complementary strand of the target sequence. In some cases, the 3' overhangs do not have complementarity to the target sequence or the complementary strand thereof. In some embodiments, the 3' overhangs comprise one, two, three, four, or more nucleotides such as 2'-deoxy(2'H) nucleotides. In some cases, the 3' overhangs comprise deoxythymidine (dT) nucleotides.

In some embodiments, the modified dsRNA agent comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region of the dsRNA agent. In some embodiments, less than about 30% (e.g., less than about 30%, 25%, 20%, 15%, 10%, or 5%) or from about 1% to about 30% (e.g., from about 1%-30%, 5%-30%, 10%-30%, 15%-30%, 20%-30%, or 25%-30%) of the nucleotides in the double-stranded region of the dsRNA agent comprise modified nucleotides.

In some embodiments, the dsRNA agent does not comprise phosphate backbone modifications, e.g., in the sense and/or antisense strand of the double-stranded region. In some embodiments, the modified dsRNA agent does not comprise 2'-deoxy nucleotides, e.g., in the sense and/or antisense strand of the double-stranded region. In certain instances, the nucleotide at the 3'-end of the double-stranded region in the sense and/or antisense strand is not a modified nucleotide. In certain instances, the nucleotides near the 3'-end (e.g., within one, two, three, or four nucleotides of the 3'-end) of the double-stranded region in the sense and/or antisense strand are not modified nucleotides.

The dsRNA agent may have 3' overhangs of one, two, three, four, or more nucleotides on one or both sides of the double-stranded region, or may lack overhangs (i.e., have blunt ends). In some cases, the dsRNA agent has 3' overhangs of two nucleotides on each side of the double-stranded region. In some embodiments, the 3' overhangs comprise one, two, three, four, or more nucleotides such as 2'-deoxy (2'H) nucleotides. In some cases, the 3' overhangs comprise deoxythymidine (dT) nucleotides.

The dsRNA agent may also have a blunt end, located at the 5'-end of the antisense strand (or the 3'-end of the sense strand) or vice versa. In some cases, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand may favor the guide strand loading into RISC process.

In some embodiments, the dsRNA agent may also have two blunt ends, at both ends of the dsRNA duplex.

In some embodiments, every nucleotide in the sense strand and antisense strand of the dsRNA agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone. In some embodiments, fewer than all nucleotides in the sense and antisense strand are modified.

As nucleic acids are polymers of subunits, in some cases, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in other cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a R A or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, purine nucleotides may be included in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. In some cases, overhangs need not be homologous with the target sequence.

In some embodiments, each residue of the sense strand and antisense strand is independently modified with LNA, HNA, CeNA, 2'-methoxyethyl, 2'-0-methyl, 2'-O-allyl, 2'-C-allyl, 2'-deoxy, or 2'-fluoro. The strands can contain more than one modification. In some embodiments, each residue of the sense strand and antisense strand is independently modified with 2'-0-methyl or 2'-fluoro.

In some embodiments, at least two different modifications are present on the sense strand and antisense strand. Those two modifications may be the 2'-0-methyl or 2'-fluoro modifications, or others.

In some embodiments, the sense strand and antisense strand each contains two differently modified nucleotides selected from 2'-O-methyl or 2'-fluoro.

In some embodiments, each residue of the sense strand and antisense strand is independently modified with 2'-O-methyl nucleotide, 2'-deoxyfluoro nucleotide, 2-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide.

The type of modifications contained in an alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "AC AC AC . . . " "BDBDBD . . . " or "CDCDCD . . . ," etc.

In some embodiments, the dsRNA agent comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5 of the strand within the duplex region. As another example, the alternating motif in the sense strand may start with "AABBAABB" from 5'-3' of the strand and the alternating motif in the anti sense strand may start with "BBAABBAA" from 3'-5 Of the strand within the duplex region, so that there is a complete or partial shift of the modification patterns between the sense strand and the anti sense strand.

In some embodiments, the dsRNA agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification. The introduction of one or more motifs of three identical modifications on three consecutive nucleotides to the sense strand and/or antisense strand interrupts the initial modification pattern present in the sense strand and/or antisense strand. This interruption of the modification pattern of the sense and/or anti sense strand by introducing one or more motifs of three identical modifications on three consecutive nucleotides to the sense and/or antisense strand may enhance the gene silencing activity to the target gene.

The dsRNA agent may comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. In some cases, these terminal three nucleotides may be at the 3'-end of the antisense strand.

In some embodiments the sense strand of the dsRNA agent comprises 1-10 blocks of two to ten phosphorothioate or methylphosphonate internucleotide linkages separated by about 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of two phosphorothioate or methylphosphonate internucleotide linkages separated by about 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of three phosphorothioate or methylphosphonate internucleotide linkages separated by about 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of four phosphorothioate or methylphosphonate internucleotide linkages separated by about 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of five phosphorothioate or methylphosphonate internucleotide linkages separated by about 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of six phosphorothioate or methylphosphonate internucleotide linkages separated by about 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of seven phosphorothioate or methylphosphonate internucleotide linkages separated by about 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of eight phosphorothioate or methylphosphonate internucleotide linkages separated by about 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of nine phosphorothioate or methylphosphonate internucleotide linkages separated by about 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments, the dsRNA agent comprises one or more phosphorothioate or methylphosphonate internucleotide linkage modification within 1-10 of the termini position(s) of the sense and/or antisense strand. For example, at least about 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA agent comprises one or more phosphorothioate or methylphosphonate internucleotide linkage modification within 1-10 of the internal region of the duplex of each of the sense and/or antisense strand. For example, at least about 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA can optionally further comprise one or more phosphorothioate or methylphosphonate internucleotide linkage modification within 1-10 of the termini position(s).

In some embodiments, the dsRNA agent comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA agent comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end). In some embodiments, the dsRNA agent comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA agent comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA agent comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA agent comprises one phosphorothioate internucleotide linkage modification within position 1-5 (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA agent comprises two phosphorothioate internucleotide linkage modifications within position 1-5 (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA agent comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA agent comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, the dsRNA agent comprises mismatch(es) with the target, within the duplex, or combinations thereof. The mismatch can occur in an overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In some cases, in terms of promoting dissociation: A:U is preferred over G:C; G:U is preferred over G:C; and I:C is preferred over G:C (I=inosine). In some cases, mismatches, e.g., non-canonical or other than canonical pairings (as described elsewhere herein) are preferred over canonical (A:T, A:U, G:C) pairings; and pairings which include a universal base are preferred over canonical pairings. In some embodiments, the dsRNA agent comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. In some embodiments, at least one of the first 1, 2 or 3 base pair within the duplex region from the 5'-end of the antisense strand is an AU base pair. For example, the first base pair within the duplex region from the 5'-end of the antisense strand is an AU base pair.

In some embodiments, the dsRNA agent is conjugated to one or more carbohydrate moieties, which may optimize one or more properties of the dsRNA agent. In some cases, the carbohydrate moiety is attached to a modified subunit of the dsRNA agent. For example, the ribose sugar of one or more ribonucleotide subunits of a dsRNA agent can be replaced with another moiety, e.g., a non-carbohydrate (e.g., cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

In some embodiments, a ligand is attached to the dsRNA via a carrier. In some cases, the carriers include (i) at least one "backbone attachment point" or two "backbone attachment points" and (ii) at least one "tethering attachment point." In some cases, a "backbone attachment point" refers to a functional group, e.g. a hydroxy 1 group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP), in some embodiments, refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier may include a functional group, e.g., an amino group, or generally, provide a bond, that is suitable for incorporation or tethering of another chemical entity, e.g., a ligand to the constituent ring.

In some embodiments the dsRNA agent is conjugated to a ligand via a carrier, wherein the carrier can be cyclic group or acyclic group; e.g., the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; e.g., the acyclic group is selected from serinol backbone or diethanolamine backbone. The dsRNA agent may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments, the dsRNA is modified to promote stability. Stabilization of synthetic siRNA, such as a dsRNA herein, against rapid nuclease degradation may be regarded as a prerequisite for in vivo and therapeutic applications. This can be achieved using a variety of stabilization chemistries previously developed for other nucleic acid drugs, such as ribozymes and antisense molecules. These include chemical modifications to the native 2'-OH group in the ribose sugar backbone, such as 2'-O-methyl (2'OMe) and 2'-Fluoro (2'F) substitutions that can be readily introduced into siRNA as 2'-modified nucleotides during RNA synthesis. In some cases, the introduction of chemical modifications to native siRNA duplexes can have a negative impact on RNAi activity, therefore the design of chemically modified siRNA may require a stochastic screening approach to identify duplexes that retain potent gene silencing activity.

In some cases, when cleavage of the sense strand is inhibited, the endonucleolytic cleavage of target mRNA is impaired In some cases, incorporation of a 2'-O-Me ribose to the Ago2 cleavage site in the sense strand inhibits RNAi. In some cases, with regard to phosphorothioate modifications, cleavage of the sense strand may be required for efficient RNAi.

In some cases, the dsRNA agent comprises 2'-F modified residues, e.g., at the Ago2 cleavage site. The modification may or may not be motif specific, e.g., one modification includes 2'-F modifications on all pyrimidines on both sense and antisense strands as long as pyrimidine residue is present, without any selectivity.

In some cases, the dsRNA agent comprises two T-F modified residues, e.g., at the Ago2 cleavage site, on the sense and/or antisense strand. In some cases, for each particular strand, either all pyrimidines or all purines are modified.

In some cases, the dsRNA agent comprises 2'-OMe modifications or various combinations of 2'-F, 2'-OMe and phosphorothioate modifications to stabilize the siRNA. In some cases, the residues at the cleavage site of the antisense strand are not be modified with 2'-OMe in order to increase the stability of the siRNA.

siRNAs

In some embodiments, the oligonucleotide comprises a small interfering RNA (siRNA) comprising a sense strand and an antisense strand. In some embodiments, the sense strand is 12-30 nucleosides in length. In some embodiments, the composition comprises a sense strand that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the composition comprises an antisense strand is 12-30 nucleosides in length. In some embodiments, the composition comprises an antisense strand that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers.

In some embodiments, the composition comprises an oligonucleotide that targets TSLP, wherein the oligonucleotides comprises a siRNA comprising a sense strand and an antisense strand. In some embodiments, the sense strand is 12-30 nucleosides in length. In some embodiments, the composition comprises a sense strand that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the composition comprises an antisense strand is 12-30 nucleosides in length. In some embodiments, the composition comprises an antisense strand that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers.

In certain aspects, the composition comprises an oligonucleotide that targets 1fTSLP, wherein the oligonucleotide comprises a siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14923. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 14923.

In certain aspects, the composition comprises an oligonucleotide that targets 1fTSLP, wherein the oligonucleotide comprises an siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14925. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 14925.

In certain aspects, the composition comprises an oligonucleotide that targets sfTSLP, wherein the oligonucleotide comprises a siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14924. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 14924.

In some embodiments, the sense strand and the antisense strand form a double-stranded RNA duplex. In some embodiments, the first base pair of the double-stranded RNA duplex is an AU base pair.

In some embodiments the composition comprises an oligonucleotide that inhibits the expression of 1fTSLP, wherein the sense strand comprises a nucleoside sequence comprising the sequence of any one of SEQ ID NOs: 14935-17526, or a nucleic acid sequence thereof having 1 or 2 nucleoside substitutions, additions, or deletions. In some embodiments, the sense strand comprises a nucleoside sequence consisting of the sequence of any one of SEQ ID NOs: 14935-17526, or a nucleic acid sequence thereof having 1 or 2 nucleoside substitutions, additions, or deletions. In some embodiments, the sense strand comprises a nucleoside sequence comprising the sequence of any one of SEQ ID NOs: 14935-17526. In some embodiments, the sense strand comprises a nucleoside sequence consisting of the sequence of any one of SEQ ID NOs: 14935-17526.

In some embodiments the composition comprises an oligonucleotide that inhibits the expression of sfTSLP, wherein the sense strand comprises a nucleoside sequence comprising or consisting of the sequence of any one of SEQ ID NOs: 22711-22906, or a nucleic acid sequence thereof having 1 or 2 nucleoside substitutions, additions, or deletions. In some embodiments, the sense strand comprises a nucleoside sequence comprising or consisting of the sequence of any one of SEQ ID NOs: 22711-22906.

In some embodiments, the composition comprises an oligonucleotide that inhibits the expression of 1fTSLP, wherein the oligonucleotide comprises a siRNA comprising a sense strand and an antisense strand, wherein the sense strand comprises a nucleoside sequence comprising or consisting of a sense strand sequence of any one of SEQ ID NOs: 14935-17526, or a nucleic acid sequence thereof having 1 or 2 nucleoside substitutions, additions, or deletions. In some embodiments, the sense strand comprises a nucleoside sequence comprising or consisting of a sense strand sequence of any one of SEQ ID NOs: 14935-17526, or a nucleic acid sequence thereof having 3 or 4 nucleoside substitutions, additions, or deletions. In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the sense strand comprises a nucleoside sequence comprising or consisting of a sense strand sequence of any one of SEQ ID NOs: 14935-17526, or a nucleic acid sequence thereof having 1 or 2 nucleoside additions at the 3' end.

In some embodiments, the composition comprises an oligonucleotide that inhibits the expression of sfTSLP, wherein the oligonucleotide comprises a siRNA comprising a sense strand and an antisense strand, wherein the sense strand comprises a nucleoside sequence comprising or consisting of a sense strand sequence of any one of SEQ ID NOs: 22711-22906, or a nucleic acid sequence thereof having 1 or 2 nucleoside substitutions, additions, or deletions. In some embodiments, the sense strand comprises a nucleoside sequence comprising or consisting of a sense strand sequence of any one of SEQ ID NOs: 22711-22906, or a nucleic acid sequence thereof having 3 or 4 nucleoside substitutions, additions, or deletions. In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the sense strand comprises a nucleoside sequence comprising or consisting of a sense strand sequence of any one of SEQ ID NOs: 22711-22906, or a nucleic acid sequence thereof having 1 or 2 nucleoside additions at the 3' end.

In some embodiments the composition comprises an oligonucleoside that inhibits the expression of 1fTSLP, wherein the antisense strand comprises a nucleoside sequence comprising or consisting of the sequence of any one of SEQ ID NOs: 26134-28725, or a nucleic acid sequence thereof having 1 or 2 nucleoside substitutions, additions, or deletions. In some embodiments, the antisense strand comprises a nucleoside sequence comprising or consisting of the sequence of any one of SEQ ID NOs: 26134-28725.

In some embodiments the composition comprises an oligonucleoside that inhibits the expression of sfTSLP, wherein the antisense strand comprises a nucleoside sequence comprising or consisting of the sequence of any one of SEQ ID NOs: 28726-28921, or a nucleic acid sequence thereof having 1 or 2 nucleoside substitutions, additions, or deletions. In some embodiments, the antisense strand comprises a nucleoside sequence comprising or consisting of the sequence of any one of SEQ ID NOs: 28726-28921.

In some embodiments, the composition comprises an oligonucleotide that inhibits the expression of 1fTSLP, wherein the oligonucleotide comprises a siRNA comprising a sense strand and an antisense strand, wherein the antisense strand comprises a nucleoside sequence comprising or consisting of a sense strand sequence of any one of SEQ ID NOs: 14935-17526, or a nucleic acid sequence thereof having 1 or 2 nucleoside substitutions, additions, or deletions. In some embodiments, the antisense strand comprises a nucleoside sequence comprising or consisting of a sense strand sequence of any one of SEQ ID NOs: 14935-17526, or a nucleic acid sequence thereof having 3 or 4 nucleoside substitutions, additions, or deletions. In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the antisense strand comprises a nucleoside sequence comprising or consisting of a antisense strand sequence of any one of SEQ ID NOs: 26134-28725, or a nucleic acid sequence thereof having 1 or 2 nucleoside additions at the 3' end.

In some embodiments, the composition comprises an oligonucleotide that inhibits the expression of sfTSLP, wherein the oligonucleotide comprises a siRNA comprising a sense strand and an antisense strand, wherein the antisense strand comprises a nucleoside sequence comprising or consisting of a sense strand sequence of any one of SEQ ID NOs: 22711-22906, or a nucleic acid sequence thereof having 1 or 2 nucleoside substitutions, additions, or deletions. In some embodiments, the antisense strand comprises a nucleoside sequence comprising or consisting of a sense strand sequence of any one of SEQ ID NOs: 22711-22906, or a nucleic acid sequence thereof having 3 or 4 nucleoside substitutions, additions, or deletions. In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the antisense strand comprises a nucleoside sequence comprising or consisting of a antisense strand sequence of any one of SEQ ID NOs: 28726-28921, or a nucleic acid sequence thereof having 1 or 2 nucleoside additions at the 3' end.

In some embodiments, the composition comprises an oligonucleotide that inhibits the expression of 1fTSLP, wherein the siRNA binds with a 17 mer in a non-human primate 1fTSLP mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a human 1fTSLP mRNA.

In some embodiments, the composition comprises an oligonucleotide that inhibits the expression of sfTSLP, wherein the siRNA binds with a 17 mer in a non-human primate sfTSLP mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a human sfTSLP mRNA.

In some embodiments, the composition comprises an oligonucleotide that inhibits the expression of 1fTSLP, wherein the siRNA binds with a 19 mer in a human 1fTSLP mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a human 1fTSLP mRNA.

In some embodiments, the composition comprises an oligonucleotide that inhibits the expression of sfTSLP, wherein the siRNA binds with a 19 mer in a human sfTSLP mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a human sfTSLP mRNA.

In some embodiments, the composition comprises an oligonucleotide that inhibits the expression of 1fTSLP, wherein the siRNA binds with a human 1fTSLP mRNA and less than or equal to 20 human off-targets, with no more than 2 mismatches in the antisense strand. In some embodiments, the composition comprises an oligonucleotide that inhibits the expression of 1fTSLP, wherein the oligonucleotide comprises a siRNA comprising a sense strand and an antisense strand, wherein the siRNA binds with a human 1fTSLP mRNA and less than or equal to 20 human off-targets, with no more than 2 mismatches in the antisense strand. In some embodiments, the siRNA binds with a human 1fTSLP mRNA and less than or equal to 10 human off-targets, with no more than 2 mismatches in the antisense strand. In some embodiments, the siRNA binds with a human 1fTSLP mRNA and less than or equal to 30 human off-targets, with no more than 2 mismatches in the antisense strand. In some embodiments, the siRNA binds with a human 1fTSLP mRNA and less than or equal to 40 human off-targets, with no more than 2 mismatches in the antisense strand. In some embodiments, the siRNA binds with a human 1fTSLP mRNA and less than or equal to 50 human off-targets, with no more than 2 mismatches in the antisense strand. In some embodiments, the siRNA binds with a human 1fTSLP mRNA and less than or equal to 10 human off-targets, with no more than 3 mismatches in the antisense strand. In some embodiments, the siRNA binds with a human 1fTSLP mRNA and less than or equal to 20 human off-targets, with no more than 3 mismatches in the antisense strand. In some embodiments, the siRNA binds with a human 1fTSLP mRNA and less than or equal to 30 human off-targets, with no more than 3 mismatches in the antisense strand. In some embodiments, the siRNA binds with a human 1fTSLP mRNA and less than or equal to 40 human off-targets, with no more than 3 mismatches in the antisense strand. In some embodiments, the siRNA binds with a human 1fTSLP mRNA and less than or equal to 50 human off-targets, with no more than 3 mismatches in the antisense strand.

In some embodiments, the composition comprises an oligonucleotide that inhibits the expression of sfTSLP, wherein the siRNA binds with a human sfTSLP mRNA and less than or equal to 20 human off-targets, with no more than 2 mismatches in the antisense strand. In some embodiments, the composition comprises an oligonucleotide that inhibits the expression of sfTSLP, wherein the oligonucleotide comprises a siRNA comprising a sense strand and an antisense strand, wherein the siRNA binds with a human sfTSLP mRNA and less than or equal to 20 human off-targets, with no more than 2 mismatches in the antisense strand. In some embodiments, the siRNA binds with a human sfTSLP mRNA and less than or equal to 10 human off-targets, with no more than 2 mismatches in the antisense strand. In some embodiments, the siRNA binds with a human sfTSLP mRNA and less than or equal to 30 human off-targets, with no more than 2 mismatches in the antisense strand. In some embodiments, the siRNA binds with a human sfTSLP mRNA and less than or equal to 40 human off-targets, with no more than 2 mismatches in the antisense strand. In some embodiments, the siRNA binds with a human sfTSLP mRNA and less than or equal to 50 human off-targets, with no more than 2 mismatches in the antisense strand. In some embodiments, the siRNA binds with a human sfTSLP mRNA and less than or equal to 10 human off-targets, with no more than 3 mismatches in the antisense strand. In some embodiments, the siRNA binds with a human sfTSLP mRNA and less than or equal to 20 human off-targets, with no more than 3 mismatches in the antisense strand. In some embodiments, the siRNA binds with a human sfTSLP mRNA and less than or equal to 30 human off-targets, with no more than 3 mismatches in the antisense strand. In some embodiments, the siRNA binds with a human sfTSLP mRNA and less than or equal to 40 human off-targets, with no more than 3 mismatches in the antisense strand. In some embodiments, the siRNA binds with a human sfTSLP mRNA and less than or equal to 50 human off-targets, with no more than 3 mismatches in the antisense strand.

In some embodiments, the composition comprises an oligonucleotide that inhibits the expression of 1fTSLP, wherein the oligonucleotide comprises a siRNA comprising a sense and an anti sense sequence, wherein the siRNA binds with a human 1fTSLP mRNA target site that does not harbor an SNP, with a minor allele frequency (MAF) greater or equal to 1% (pos. 2-18). In some embodiments, the MAF is greater or equal to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, the composition comprises an oligonucleotide that inhibits the expression of sfTSLP, wherein the oligonucleotide comprises a siRNA comprising a sense and an anti sense sequence, wherein the siRNA binds with a human sfTSLP mRNA target site that does not harbor an SNP, with a minor allele frequency (MAF) greater or equal to 1% (pos. 2-18). In some embodiments, the MAF is greater or equal to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, the composition comprises an oligonucleotide that inhibits the expression of 1fTSLP, wherein the oligonucleotide comprises a siRNA comprising a sense and an antisense sequence, wherein the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326, or a nucleic acid sequence thereof having 1 or 2 nucleoside substitutions, additions, or deletions; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525, or a nucleic acid sequence thereof having 1 or 2 nucleoside substitutions, additions, or deletions.

In some embodiments, the composition comprises an oligonucleotide that inhibits the expression of 1fTSLP, wherein the oligonucleotide comprises a siRNA comprising a sense and an antisense sequence, the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525.

In some embodiments, the composition comprises an oligonucleotide that inhibits the expression of 1fTSLP, wherein the oligonucleotide comprises a siRNA comprising a sense and an antisense sequence, the sense strand comprising the nucleoside sequence of any one of SEQ ID NOs: 20125, 20126, 20131, 20132, 20134, 20141, 20143, 20144, 20145, 20146, 20157, 20188, 20189, 20197, 20219, 20223, 20224, 20225, 20227, 20231, 20232, 20233, 20234, 20235, 20236, 20240, 20241, 20243, 20246, 20266, 20278, 20280, 20281, 20282, 20285, 20286, 20291, 20292, 20295, 20298, 20301, 20307, 20311, 20312, 20348, 20358, 20362, 20368, 20370, 20371, 20372, 20374, 20375, 20378, 20379, 20381, 20414, 20419, 20420, 20422, 20424, 20425, 20430, 20436, 20437, 20444, 20447, 20448, 20456, 20458, 20460, 20462, 20463, 20466, 20467, 20470, 20478, 20486, 20487, 20491, 20494, 20498, 20503, 20504, 20505, 20506, 20508, or 20510, and/or the antisense strand comprising the nucleoside sequence of any one of SEQ ID NOs: 31520, 31521, 31526, 31527, 31529, 31536, 31538, 31539, 31540, 31541, 31552, 31583, 31584, 31592, 31614, 31618, 31619, 31620, 31622, 31626, 31627, 31628, 31629, 31630, 31631, 31635, 31636, 31638, 31641, 31661, 31673, 31675, 31676, 31677, 31680, 31681, 31686, 31687, 31690, 31693, 31696, 31702, 31706, 31707, 31743, 31753, 31757, 31763, 31765, 31766, 31767, 31769, 31770, 31773, 31774, 31776, 31809, 31814, 31815, 31817, 31819, 31820, 31825, 31831, 31832, 31839, 31842, 31843, 31851, 31853, 31855, 31857, 31858, 31861, 31862, 31865, 31873, 31881, 31882, 31886, 31889, 31893, 31898, 31899, 31900, 31901, 31903, or 31905.

In some embodiments, the composition comprises an oligonucleotide that inhibits the expression of 1fTSLP, wherein the oligonucleotide comprises a siRNA comprising a sense and an antisense sequence, the sense strand comprises the nucleoside sequence of any one of SEQ ID NOs: 14942, 14947, 14948, 14950, 14957, 14959, 15004, 15035, 15039, 15040, 15041, 15043, 15047, 15048, 15049, 15050, 15051, 15057, 15059, 15082, 15094, 15096, 15097, 15098, 15102, 15107, 15108, 15111, 15114, 15123, 15127, 15128, 15164, 15184, 15186, 15187, 15188, 15190, 15191, 15194, 15195, 15230, 15235, 15236, 15238, 15241, 15246, 15252, 15260, 15263, 15272, 15276, 15278, 15279, 15283, 15294, 15302, 15307, 15314, 15322, 15324, or 15326; and/or wherein the antisense strand comprises the nucleoside sequence of any one of SEQ ID NOs: 26141, 26146, 26147, 26149, 26156, 26158, 26203, 26234, 26238, 26239, 26240, 26242, 26246, 26247, 26248, 26249, 26250, 26256, 26258, 26281, 26293, 26295, 26296, 26297, 26301, 26306, 26307, 26310, 26313, 26322, 26326, 26327, 26363, 26383, 26385, 26386, 26387, 26389, 26390, 26393, 26394, 26429, 26434, 26435, 26437, 26440, 26445, 26451, 26459, 26462, 26471, 26475, 26477, 26478, 26482, 26493, 26501, 26506, 26513, 26521, 26523, or 26525. In some embodiments, the composition comprises an oligonucleotide that inhibits the expression of 1fTSLP, wherein the oligonucleotide comprises a siRNA comprising a sense and an antisense sequence, wherein the sense strand comprises the nucleoside sequence of any one of SEQ ID NOs: 15041, 15048, 15051, 15082, 15096, 15111, 15114, 15123, 15128, 15187, 15194, 15230, 15235, 15238, 15241, 15252, 15272, 15278, 15307, or 15326; and/or wherein the antisense strand comprises the nucleoside sequence of any one of SEQ ID NOs: 26240, 26247, 26250, 26281, 26295, 26310, 26313, 26322, 26327, 26386, 26393, 26429, 26434, 26437, 26440, 26451, 26471, 26477, 26506, or 26525.

In some embodiments, the composition comprises an oligonucleotide that inhibits the expression of 1fTSLP, wherein the oligonucleotide comprises a siRNA comprising a sense and an antisense sequence, wherein the sense strand comprises the nucleoside sequence of any one of SEQ ID NOs: 15048, 15051, 15082, 15096, 15111, 15114, 15123, 15128, 15194, 15230, 15235, 15238, 15241, 15252, 15272, 15278, 15307, or 15326; and/or wherein the antisense strand comprises the nucleoside sequence of any one of SEQ ID NOs: 26247, 26250, 26281, 26295, 26310, 26313, 26322, 26327, 26393, 26429, 26434, 26437, 26440, 26451, 26471, 26477, 26506, or 26525.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of SEQ ID NOS: 22734, 22736, 22738, 22746, 22773, 22778, 22780, 22781, 22782, 22783, 22785, 22786, 22787, 22788, 22789, 22790, 22824, 22825, 22827, 22828, 22872, 22873, 22874, 22876, 22877, 22879, 22880, 22881, 22882, 22884, 22885, 22887, 22889, 22890, 22895, 22898, or 22904; and/or wherein the antisense strand comprises the nucleoside sequence of any one of SEQ ID NOS: 28749, 28751, 28753, 28761, 28788, 28793, 28795, 28796, 28797, 28798, 28800, 28801, 28802, 28803, 28804, 28805, 28839, 28840, 28842, 28843, 28887, 28888, 28889, 28891, 28892, 28894, 28895, 28896, 28897, 28899, 28900, 28902, 28904, 28905, 28910, 28913, or 28919.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of SEQ ID NOs: 22930, 22932, 22934, 22942, 22969, 22974, 22976, 22977, 22978, 22979, 22981, 22982, 22983, 22984, 22985, 22986, 23020, 23021, 23023, 23024, 23068, 23069, 23070, 23072, 23073, 23075, 23076, 23077, 23078, 23080, 23081, 23083, 23085, 23086, 23091, 23094, or 23100; and/or wherein the antisense strand comprises the nucleoside sequence of any one of SEQ ID NOs: 34129, 34131, 34133, 34141, 34168, 34173, 34175, 34176, 34177, 34178, 34180, 34181, 34182, 34183, 34184, 34185, 34219, 34220, 34222, 34223, 34267, 34268, 34269, 34271, 34272, 34274, 34275, 34276, 34277, 34279, 34280, 34282, 34284, 34285, 34290, 34293, or 34299.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of 22969, 22974, or 23094, and/or wherein the antisense strand comprises the nucleoside sequence of any one of SEQ ID NOS: 34168, 34173, or 34293.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of SEQ ID NOs: 23126, 23128, 23130, 23138, 23165, 23170, 23172, 23173, 23174, 23175, 23177, 23178, 23179, 23180, 23181, 23182, 23216, 23217, 23219, 23220, 23264, 23265, 23266, 23268, 23269, 23271, 23272, 23273, 23274, 23276, 23277, 23279, 23281, 23282, 23287, 23290, or 23296, and/or wherein the antisense strand comprises the nucleoside sequence of any one of SEQ ID NOs: 34521, 34523, 34525, 34533, 34560, 34565, 34567, 34568, 34569, 34570, 34572, 34573, 34574, 34575, 34576, 34577, 34611, 34612, 34614, 34615, 34659, 34660, 34661, 34663, 34664, 34666, 34667, 34668, 34669, 34671, 34672, 34674, 34676, 34677, 34682, 34685, or 34691.

In some embodiments, the sense strand is complementary to or targets a sequence within the first 412 nucleotides of SEQ ID NO: 14923. In some embodiments, the antisense strand is complementary to or targets a sequence within the first 412 nucleotides of SEQ ID NO: 14923. In some embodiments, the sense strand is complementary to or targets a sequence within nucleotides 8-412 of SEQ ID NO: 14923. In some embodiments, the antisense strand is complementary to or targets a sequence within nucleotides 8-412 of SEQ ID NO: 14923.

In some embodiments, the sense strand is complementary to or targets a sequence within a sequence within a 5' UTR of 1fTSLP. In some embodiments, the antisense strand is complementary to or targets a sequence within a 5' UTR of 1fTSLP. In some embodiments, the sense strand is complementary to or targets a sequence within a 3' UTR of 1fTSLP. In some embodiments, the antisense strand is complementary to or targets a sequence within a 3' UTR of 1fTSLP. In some embodiments, the sense strand is complementary to or targets a sequence within a coding region of 1fTSLP. In some embodiments, the antisense strand is complementary to or targets a sequence within a coding region of 1fTSLP.

In some embodiments, the sense strand is complementary to or targets a sequence within a sequence within a 5' UTR of sfTSLP. In some embodiments, the antisense strand is complementary to or targets a sequence within a 5' UTR of sfTSLP. In some embodiments, the sense strand is complementary to or targets a sequence within a 3' UTR of sfTSLP. In some embodiments, the antisense strand is complementary to or targets a sequence within a 3' UTR of sfTSLP. In some embodiments, the sense strand is complementary to or targets a sequence within a coding region of sfTSLP. In some embodiments, the antisense strand is complementary to or targets a sequence within a coding region of sfTSLP.

siRNA Modifications

In some embodiments, the composition comprises an oligonucleotide that inhibits the expression of 1fTSLP, wherein the oligonucleotide comprises a siRNA comprising a sense strand and an antisense strand, wherein the sense strand comprises the nucleoside sequence of any one of SEQ ID NOs: 17527-20118. In some embodiments, the sense strand comprises the nucleoside sequence of any one of SEQ ID NOs: 17527-20118, or a nucleic acid sequence thereof having 1 or 2 nucleoside substitutions, additions, or deletions. In some embodiments, the sense strand comprises the nucleoside sequence of any one of SEQ ID NOs: 17527-20118, or a nucleic acid sequence thereof having 3 or 4 nucleoside substitutions, additions, or deletions.

In some embodiments, the composition comprises an oligonucleotide that inhibits the expression of sfTSLP, wherein the oligonucleotide comprises a siRNA comprising a sense strand and an antisense strand, wherein the sense strand comprises the nucleoside sequence of any one of SEQ ID NOs: 22907-23102. In some embodiments, the sense strand comprises the nucleoside sequence of any one of SEQ ID NOs: 22907-23102, or a nucleic acid sequence thereof having 1 or 2 nucleoside substitutions, additions, or deletions. In some embodiments, the sense strand comprises the nucleoside sequence of any one of SEQ ID NOs: 22907-23102, or a nucleic acid sequence thereof having 3 or 4 nucleoside substitutions, additions, or deletions.

In some embodiments, the composition comprises an oligonucleotide that inhibits the expression of 1fTSLP, wherein the oligonucleotide comprises an siRNA comprising a sense strand and an antisense strand, wherein the sense strand comprises the nucleoside sequence of any one of SEQ ID NOs: 20119-22710. In some embodiments, the sense strand comprises the nucleoside sequence of any one of SEQ ID NOs: 20119-22710, or a nucleic acid sequence thereof having 1 or 2 nucleoside substitutions, additions, or deletions. In some embodiments, the sense strand comprises the nucleoside sequence of any one of SEQ ID NOs: 20119-22710, or a nucleic acid sequence thereof having 3 or 4 nucleoside substitutions, additions, or deletions.

In some embodiments, the composition comprises an oligonucleotide that inhibits the expression of 1fTSLP, wherein the oligonucleotide comprises an siRNA comprising a sense strand and an antisense strand, wherein the anti sense strand comprises the nucleoside sequence of any one of SEQ ID NOs: 28922-31513. In some embodiments, the antisense strand comprises the nucleoside sequence of any one of SEQ ID NOs: 28922-31513, or a nucleic acid sequence thereof having 1 or 2 nucleoside substitutions, additions, or deletions. In some embodiments, the antisense strand comprises the nucleoside sequence of any one of SEQ ID NOs: 28922-31513, or a nucleic acid sequence thereof having 3 or 4 nucleoside substitutions, additions, or deletions.

In some embodiments, the composition comprises an oligonucleotide that inhibits the expression of sfTSLP, wherein the oligonucleotide comprises an siRNA comprising a sense strand and an antisense strand, wherein the anti sense strand comprises the nucleoside sequence of any one of SEQ ID NOs: 34106-34301. In some embodiments, the antisense strand comprises the nucleoside sequence of any one of SEQ ID NOs: 34106-34301, or a nucleic acid sequence thereof having 1 or 2 nucleoside substitutions, additions, or deletions. In some embodiments, the antisense strand comprises the nucleoside sequence of any one of SEQ ID NOs: 34106-34301, or a nucleic acid sequence thereof having 3 or 4 nucleoside substitutions, additions, or deletions.

In some embodiments, the composition comprises an oligonucleotide that inhibits the expression of 1fTSLP, wherein the oligonucleotide comprises an siRNA comprising a sense strand and an antisense strand, wherein the antisense strand comprises the nucleoside sequence of any one of SEQ ID NOs: 31514-34105. In some embodiments, the antisense strand comprises the nucleoside sequence of any one of SEQ ID NOs: 31514-34105, or a nucleic acid sequence thereof having 1 or 2 nucleoside substitutions, additions, or deletions. In some embodiments, the antisense strand comprises the nucleoside sequence of any one of SEQ ID NOs: 31514-34105, or a nucleic acid sequence thereof having 3 or 4 nucleoside substitutions, additions, or deletions.

In some embodiments, the composition comprises an oligonucleotide that inhibits the expression of sfTSLP, wherein the oligonucleotide comprises an siRNA comprising a sense strand and an antisense strand, wherein the antisense strand comprises the nucleoside sequence of any one of SEQ ID NOs: 34302-34497. In some embodiments, the antisense strand comprises the nucleoside sequence of any one of SEQ ID NOs: 34302-34497, or a nucleic acid sequence thereof having 1 or 2 nucleoside substitutions, additions, or deletions. In some embodiments, the antisense strand comprises the nucleoside sequence of any one of SEQ ID NOs: 34302-34497, or a nucleic acid sequence thereof having 3 or 4 nucleoside substitutions, additions, or deletions.

In some embodiments, the composition comprises an oligonucleotide that inhibits the expression of 1fTSLP, wherein the oligonucleotide comprises an siRNA comprising a sense strand and an antisense strand, wherein the sense strand comprises modification pattern 1S: 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5'-nsnsnnNfnNfNfNfnnnnnnnnnsnsn-3' (SEQ ID NO: 34504), wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5'-nsnsnnNfnNfnNfnnnnnnnnnnnsnsn-3' (SEQ ID NO: 34507), wherein "Nf" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfnNfnNfNfNfnNfnNffiNffiNfnNfnNfsnsnN-Lipid-3' (SEQ ID NO: 34508), wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 5S: 5'-nsnsnnNffiNfNfNfnnnnnnnnnnsnsnN-Lipid-3' (SEQ ID NO: 34509), wherein "Nf" is a 2' fluoro-modified nucleoside, "n" is a 2' O-methyl modified nucleoside, "s" is a phosphorothioate linkage, and N comprises one or more nucleosides.

In some embodiments, the composition comprises an oligonucleotide that inhibits the expression of sfTSLP, wherein the oligonucleotide comprises an siRNA comprising a sense strand and an antisense strand, wherein the sense strand comprises modification pattern 1S 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5'-nsnsnnNfnNfNfNfnnnnnnnnnnsnsn-3' (SEQ ID NO: 34504), wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5'-nsnsnnNfnNfnNfnnnnnnnnnnnsnsn-3' (SEQ ID NO: 34507), wherein "Nf" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfnNfnNfNfNfnNfnNfnNfnNfnNfsnsnN-Lipid-3' (SEQ ID NO: 34508), wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 5S: 5'-nsnsnnNfnNfNfNfnnnnnnnnnnnsnsnN-Lipid-3' (SEQ ID NO: 34509), wherein "Nf" is a 2' fluoro-modified nucleoside, "n" is a 2' O-methyl modified nucleoside, "s" is a phosphorothioate linkage, and N comprises one or more nucleosides.

In some embodiments, the composition comprises an oligonucleotide that inhibits the expression of 1fTSLP, wherein the oligonucleotide comprises an siRNA comprising a sense strand and an antisense strand, wherein the antisense strand comprises modification pattern 1AS: 5'-nsNfsnNfnNfnNfnNfnNfnnnNfnNfnNfsnsn-3' (SEQ ID NO: 34503), wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnnnNfnNfNfnnnnNfnNfnnnsnsn-3' (SEQ ID NO: 34510), wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsNfsnnnNfnnnnnnnNfnNfnnnsnsn-3' (SEQ ID NO: 34505), wherein "Nf" is a 2' fluoro-modified nucleoside, "n" is a 2' O-methyl modified nucleoside, and "s" is a phosphorothioate linkage. In some embodiments, the antisense strand comprises modification pattern 4AS: 5'-nsNfsnNfnNfnnnnnnnNfnNfnnnsnsn-3' (SEQ ID NO: 34511), wherein "Nf" is a 2' fluoro-modified nucleoside, "n" is a 2' O-methyl modified nucleoside, and "s" is a phosphorothioate linkage.

In some embodiments, the composition comprises an oligonucleotide that inhibits the expression of sfTSLP, wherein the oligonucleotide comprises an siRNA comprising a sense strand and an antisense strand, wherein the antisense strand comprises modification pattern 1AS: 5'-nsNfsnNfnNfnNfnNfnNfnnnNfnNfnNfsnsn-3' (SEQ ID NO: 34503), wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnnnNfnNfNfnnnnNfnNfnnnsnsn-3' (SEQ ID NO: 34510), wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsNfsnnnNfnnnnnnnNfnNfnnnsnsn-3' (SEQ ID NO: 34505), wherein "Nf" is a 2' fluoro-modified nucleoside, "n" is a 2' O-methyl modified nucleoside, and "s" is a phosphorothioate linkage. In some embodiments, the antisense strand comprises modification pattern 4AS: 5'-nsNfsnNfnNfnnnnnnnNfnNfnnnsnsn-3' (SEQ ID NO: 34511), wherein "Nf" is a 2' fluoro-modified nucleoside, "n" is a 2' O-methyl modified nucleoside, and "s" is a phosphorothioate linkage.

In some embodiments, the composition comprises an oligonucleotide that inhibits the expression of 1fTSLP, wherein the oligonucleotide comprises an siRNA comprising a sense strand and an antisense strand, wherein the sense strand comprises pattern 1S and the antisense strand comprises pattern 1AS, 2AS, 3AS, or 4AS. In some embodiments the sense strand comprises pattern 2S and the antisense strand comprises pattern 1AS, 2AS, 3AS, or 4AS. In some embodiments the sense strand comprises pattern 3S and the antisense strand comprises pattern 1AS, 2AS, 3AS, or 4AS. In some embodiments the sense strand comprises pattern 4S and the antisense strand comprises pattern 1AS, 2AS, 3AS, or 4AS.

In some embodiments, the composition comprises an oligonucleotide that inhibits the expression of sfTSLP, wherein the oligonucleotide comprises an siRNA comprising a sense strand and an antisense strand, wherein the sense strand comprises pattern 1S and the antisense strand comprises pattern 1AS, 2AS, 3AS, or 4AS. In some embodiments the sense strand comprises pattern 2S and the antisense strand comprises pattern 1AS, 2AS, 3AS, or 4AS. In some embodiments the sense strand comprises pattern 3S and the antisense strand comprises pattern 1AS, 2AS, 3AS, or 4AS. In some embodiments the sense strand comprises pattern 4S and the antisense strand comprises pattern 1AS, 2AS, 3AS, or 4AS.

In some embodiments, the composition comprises an oligonucleotide that inhibits the expression of 1fTSLP, wherein the oligonucleotide comprises an siRNA comprising a sense strand and an antisense strand, wherein the sense strand comprises the nucleoside sequence of any one of SEQ ID NOs: 17533, 17534, 17539, 17540, 17542, 17549, 17551, 17552, 17553, 17554, 17565, 17596, 17597, 17605, 17627, 17631, 17632, 17633, 17635, 17639, 17640, 17641, 17642, 17643, 17644, 17648, 17649, 17651, 17654, 17674, 17686, 17688, 17689, 17690, 17693, 17694, 17699, 17700, 17703, 17706, 17709, 17715, 17719, 17720, 17756, 17766, 17770, 17776, 17778, 17779, 17780, 17782, 17783, 17786, 17787, 17789, 17822, 17827, 17828, 17830, 17832, 17833, 17838, 17844, 17845, 17852, 17855, 17856, 17864, 17866, 17868, 17870, 17871, 17874, 17875, 17878, 17886, 17894, 17895, 17899, 17902, 17906, 17911, 17912, 17913, 17914, 17916, or 17918; and/or wherein the antisense strand comprises the nucleoside sequence of any one of SEQ ID NOs: 28928, 28929, 28934, 28935, 28937, 28944, 28946, 28947, 28948, 28949, 28960, 28991, 28992, 29000, 29022, 29026, 29027, 29028, 29030, 29034, 29035, 29036, 29037, 29038, 29039, 29043, 29044, 29046, 29049, 29069, 29081, 29083, 29084, 29085, 29088, 29089, 29094, 29095, 29098, 29101, 29104, 29110, 29114, 29115, 29151, 29161, 29165, 29171, 29173, 29174, 29175, 29177, 29178, 29181, 29182, 29184, 29217, 29222, 29223, 29225, 29227, 29228, 29233, 29239, 29240, 29247, 29250, 29251, 29259, 29261, 29263, 29265, 29266, 29269, 29270, 29273, 29281, 29289, 29290, 29294, 29297, 29301, 29306, 29307, 29308, 29309, 29311, or 29313. In some embodiments, the oligonucleotide comprises a modification pattern as described herein. In some embodiments, the oligonucleotide comprises a sense strand having the sequence of any one of SEQ ID NOs: 25890-25977. In some embodiments, the oligonucleotide comprises an antisense strand having the sequence of any one of SEQ ID NOs: 26012-26099. In some embodiments, the siRNA specifically targets 1fTSLP.

In some embodiments, the composition comprises an oligonucleotide that inhibits the expression of 1fTSLP, wherein the oligonucleotide comprises a siRNA comprising a sense and an antisense sequence, the sense strand comprising the nucleoside sequence of any one of SEQ ID NOs: 20125, 20126, 20131, 20132, 20134, 20141, 20143, 20144, 20145, 20146, 20157, 20188, 20189, 20197, 20219, 20223, 20224, 20225, 20227, 20231, 20232, 20233, 20234, 20235, 20236, 20240, 20241, 20243, 20246, 20266, 20278, 20280, 20281, 20282, 20285, 20286, 20291, 20292, 20295, 20298, 20301, 20307, 20311, 20312, 20348, 20358, 20362, 20368, 20370, 20371, 20372, 20374, 20375, 20378, 20379, 20381, 20414, 20419, 20420, 20422, 20424, 20425, 20430, 20436, 20437, 20444, 20447, 20448, 20456, 20458, 20460, 20462, 20463, 20466, 20467, 20470, 20478, 20486, 20487, 20491, 20494, 20498, 20503, 20504, 20505, 20506, 20508, or 20510, and/or the antisense strand comprising the nucleoside sequence of any one of SEQ ID NOs: 31520, 31521, 31526, 31527, 31529, 31536, 31538, 31539, 31540, 31541, 31552, 31583, 31584, 31592, 31614, 31618, 31619, 31620, 31622, 31626, 31627, 31628, 31629, 31630, 31631, 31635, 31636, 31638, 31641, 31661, 31673, 31675, 31676, 31677, 31680, 31681, 31686, 31687, 31690, 31693, 31696, 31702, 31706, 31707, 31743, 31753, 31757, 31763, 31765, 31766, 31767, 31769, 31770, 31773, 31774, 31776, 31809, 31814, 31815, 31817, 31819, 31820, 31825, 31831, 31832, 31839, 31842, 31843, 31851, 31853, 31855, 31857, 31858, 31861, 31862, 31865, 31873, 31881, 31882, 31886, 31889, 31893, 31898, 31899, 31900, 31901, 31903, or 31905; wherein the sense strand comprises Modification Pattern 2S, and/or the antisense strand comprises Modification Pattern 3AS.

In some embodiments, the composition comprises an oligonucleotide that inhibits the expression of 1fTSLP, wherein the oligonucleotide comprises an siRNA comprising a sense strand and an antisense strand, wherein the sense strand comprises the nucleoside sequence of any one of SEQ ID NOs: 17534, 17539, 17540, 17542, 17549, 17551, 17596, 17627, 17631, 17632, 17633, 17635, 17639, 17640, 17641, 17642, 17643, 17649, 17651, 17674, 17686, 17688, 17689, 17690, 17694, 17699, 17700, 17703, 17706, 17715, 17719, 17720, 17756, 17776, 17778, 17779, 17780, 17782, 17783, 17786, 17787, 17822, 17827, 17828, 17830, 17833, 17838, 17844, 17852, 17855, 17864, 17868, 17870, 17871, 17875, 17886, 17894, 17899, 17906, 17914, 17916, or 17918; and/or wherein the antisense strand comprises the nucleoside sequence of any one of SEQ ID NOs: 28929, 28934, 28935, 28937, 28944, 28946, 28991, 29022, 29026, 29027, 29028, 29030, 29034, 29035, 29036, 29037, 29038, 29044, 29046, 29069, 29081, 29083, 29084, 29085, 29089, 29094, 29095, 29098, 29101, 29110, 29114, 29115, 29151, 29171, 29173, 29174, 29175, 29177, 29178, 29181, 29182, 29217, 29222, 29223, 29225, 29228, 29233, 29239, 29247, 29250, 29259, 29263, 29265, 29266, 29270, 29281, 29289, 29294, 29301, 29309, 29311, or 29313. In some embodiments, the composition comprises an oligonucleotide that inhibits the expression of 1fTSLP, wherein the oligonucleotide comprises an siRNA comprising a sense strand and an antisense strand, wherein the sense strand comprises the nucleoside sequence of any one of SEQ ID NOs: 17633, 17640, 17643, 17674, 17688, 17703, 17706, 17715, 17720, 17779, 17786, 17822, 17827, 17830, 17833, 17844, 17864, 17870, 17899, or 17918; and/or wherein the antisense strand comprises the nucleoside sequence of any one of SEQ ID NOs: 29028, 29035, 29038, 29069, 29083, 29098, 29101, 29110, 29115, 29174, 29181, 29217, 29222, 29225, 29228, 29239, 29259, 29265, 29294, or 29313.

In some embodiments, the composition comprises an oligonucleotide that inhibits the expression of 1fTSLP, wherein the oligonucleotide comprises an siRNA comprising a sense strand and an antisense strand, wherein the sense strand comprises the nucleoside sequence of any one of SEQ ID NOs: 17640, 17643, 17674, 17688, 17703, 17706, 17715, 17720, 17786, 17822, 17827, 17830, 17833, 17844, 17864, 17870, 17899, or 17918; and/or wherein the antisense strand comprises the nucleoside sequence of any one of SEQ ID NOs: 29035, 29038, 29069, 29083, 29098, 29101, 29110, 29115, 29181, 29217, 29222, 29225, 29228, 29239, 29259, 29265, 29294, or 29313.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of SEQ ID NOS: 22734, 22736, 22738, 22746, 22773, 22778, 22780, 22781, 22782, 22783, 22785, 22786, 22787, 22788, 22789, 22790, 22824, 22825, 22827, 22828, 22872, 22873, 22874, 22876, 22877, 22879, 22880, 22881, 22882, 22884, 22885, 22887, 22889, 22890, 22895, 22898, or 22904; and/or wherein the antisense strand comprises the nucleoside sequence of any one of SEQ ID NOS: 28749, 28751, 28753, 28761, 28788, 28793, 28795, 28796, 28797, 28798, 28800, 28801, 28802, 28803, 28804, 28805, 28839, 28840, 28842, 28843, 28887, 28888, 28889, 28891, 28892, 28894, 28895, 28896, 28897, 28899, 28900, 28902, 28904, 28905, 28910, 28913, or 28919. In some embodiments, the oligonucleotide comprises a modification pattern as described herein. In some embodiments, the siRNA targets sfTSLP. In some embodiments, the oligonucleotide comprises a sense strand having the sequence of any one of SEQ ID NOs: 25978-26011. In some embodiments, the oligonucleotide comprises an antisense strand having the sequence of any one of SEQ ID NOs: 26100-26133.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of SEQ ID NOs: 22930, 22932, 22934, 22942, 22969, 22974, 22976, 22977, 22978, 22979, 22981, 22982, 22983, 22984, 22985, 22986, 23020, 23021, 23023, 23024, 23068, 23069, 23070, 23072, 23073, 23075, 23076, 23077, 23078, 23080, 23081, 23083, 23085, 23086, 23091, 23094, or 23100; and/or wherein the antisense strand comprises the nucleoside sequence of any one of SEQ ID NOs: 34129, 34131, 34133, 34141, 34168, 34173, 34175, 34176, 34177, 34178, 34180, 34181, 34182, 34183, 34184, 34185, 34219, 34220, 34222, 34223, 34267, 34268, 34269, 34271, 34272, 34274, 34275, 34276, 34277, 34279, 34280, 34282, 34284, 34285, 34290, 34293, or 34299.

In some embodiments, the composition comprises an oligonucleotide that inhibits the expression of sfTSLP, wherein the oligonucleotide comprises a siRNA comprising a sense and an anti sense sequence, wherein the sense strand comprises the nucleoside sequence of any one of 22969, 22974, or 23094, and/or wherein the antisense strand comprises the nucleoside sequence of any one of SEQ ID NOS: 34168, 34173, or 34293; wherein the sense strand comprises modification pattern 1S and/or the antisense strand comprises modification pattern 1AS.

In some embodiments, the composition comprises an oligonucleotide that inhibits the expression of sfTSLP, wherein the oligonucleotide comprises a siRNA comprising a sense and an antisense sequence, wherein the sense strand comprises the nucleoside sequence of any one of SEQ ID NOs: 23126, 23128, 23130, 23138, 23165, 23170, 23172, 23173, 23174, 23175, 23177, 23178, 23179, 23180, 23181, 23182, 23216, 23217, 23219, 23220, 23264, 23265, 23266, 23268, 23269, 23271, 23272, 23273, 23274, 23276, 23277, 23279, 23281, 23282, 23287, 23290, or 23296, and/or wherein the antisense strand comprises the nucleoside sequence of any one of SEQ ID NOs: 34521, 34523, 34525, 34533, 34560, 34565, 34567, 34568, 34569, 34570, 34572, 34573, 34574, 34575, 34576, 34577, 34611, 34612, 34614, 34615, 34659, 34660, 34661, 34663, 34664, 34666, 34667, 34668, 34669, 34671, 34672, 34674, 34676, 34677, 34682, 34685, or 34691; wherein the sense strand comprises modification pattern 2S, and/or the antisense strand comprises modification pattern 3AS.

In some embodiments, the sense strand comprises any one of modification patterns 1S, 2S, 3S, 4S, or 5S. In some embodiments, the sense strand comprises any one of modification patterns 1AS, 2AS, 3AS, or 4AS. In some embodiments, the sense strand comprises the modification pattern of SEQ ID NO: 34506.

In some embodiments, the antisense strand comprises any one of modification patterns 1S, 2 S, 3S, 4S, or 5S. In some embodiments, the antisense strand comprises any one of modification patterns 1AS, 2AS, 3AS, or 4AS. In some embodiments, the antisense strand comprises the modification pattern of SEQ ID NO: 34506. In some embodiments, the modification or modification pattern provides nuclease resistance to the siRNA.

Antisense Compounds

In one aspect, provided herein is an antisense compound or oligonucleotide for modulating the activity and/or expression of a target nucleic acid, e.g., TSLP or specifically 1fTSLP. In some embodiments, the antisense compound inhibits expression of TSLP or specifically 1fTSLP. In some cases, the antisense compound comprises a sequence at least about 80%, 85%, 90%, 95%, or 100% identical to a sequence selected from SEQ ID NOS: 9971-14922. In some cases, the antisense compound comprises a sequence at least about 80%, 85%, 90%, 95%, or 100% identical to a sequence selected from SEQ ID NOS: 9971-12561. In some embodiments, the antisense compound inhibits expression of sfTSLP. In some cases, the antisense compound comprises a sequence at least about 80%, 85%, 90%, 95%, or 100% identical to a sequence selected from SEQ ID NOS: 12562-14922.

In some embodiments, the antisense compound is specifically hybridizable to the target nucleic acid, where binding of the compound to the target nucleic acid interferes with the normal function of the target nucleic acid to cause, e.g., a loss of activity, and there is a sufficient degree of complementarity to avoid non-specific binding of the antisense compound to non-target nucleic acid sequences under conditions in which specific binding is desired. Such conditions include physiological conditions in the case of in vivo assays or therapeutic treatment, and conditions in which assays are performed in the case of in vitro assays.

In some embodiments, the antisense compounds include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, an antisense compound, whether DNA, RNA, chimeric, substituted etc, is specifically hybridizable when binding of the compound to the target DNA or RNA molecule interferes with the normal function of the target DNA or RNA, e.g., to cause a loss of utility, and there is a sufficient degree of complementarily to avoid nonspecific binding of the antisense compound to non-target sequences under conditions in which specific binding is desired, i.e., under physiological conditions in the case of in vivo assays or therapeutic treatment, and in the case of in vitro assays, under conditions in which the assays are performed.

In some embodiments, targeting of 1fTSLP includes without limitation, antisense sequences which are identified and expanded, using for example, PCR, hybridization etc., one or more of the sequences set forth as SEQ ID NOS: 9971-14922, and the like (e.g., oligonucleotides having at least about 80%, 85%, 90%, 95%, or 100% identity to a sequence selected from SEQ ID NOS: 9971-14922), to modulate the expression or function of 1fTSLP. In some embodiments, expression or function is down-regulated as compared to a control oligonucleotide that does not specifically hybridize to 1fTSLP.

In some embodiments, an antisense oligonucleotide comprises one or more modified nucleotides, shorter or longer fragments, modified bonds and the like. Examples of modified bonds or internucleotide linkages comprise phosphorothioate, phosphorodithioate or the like. In some embodiments, the nucleotides comprise a phosphorus derivative. The phosphorus derivative (or modified phosphate group) which may be attached to the sugar or sugar analog moiety in the modified oligonucleotides may be a monophosphate, diphosphate, triphosphate, alkylphosphate, alkanephosphate, phosphorothioate and the like.

In embodiments, oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule can be a multistep process. The process may begin with the identification of a target nucleic acid whose function is to be modulated. This target nucleic acid may be, for example, a cellular gene (or mRNA transcribed from the gene) whose expression is associated with a particular disorder or disease state. In some embodiments, the target nucleic acid encodes long-form thymic stromal lymphopoietin (1fTSLP).

The targeting process may include determination of at least one target region, segment, or site within the target nucleic acid for the antisense interaction to occur such that the desired effect, e.g., modulation of expression, will result. In some embodiments, the term "region" is defined as a portion of the target nucleic acid having at least one identifiable structure, function, or characteristic. Within regions of target nucleic acids are segments. "Segments" may be defined as smaller or sub-portions of regions within a target nucleic acid. "Sites" may be defined as positions within a target nucleic acid.

In some embodiments, the antisense oligonucleotides bind to the natural antisense sequences of long-form thymic stromal lymphopoietin (1fTSLP) and modulate the expression and/or function of 1fTSLP (SEQ ID NO: 14923). An example of antisense sequences include SEQ ID NOS: 14926, 9971-14922, and a sequence at least about 80%, 85%, 90%, 95%, or 100% identical to a sequence selected from SEQ ID NOS: 9971-12561. In some embodiments, the anti sense oligonucleotides bind to the natural antisense sequences of sfTSLP and modulate the expression and/or function of sfTSLP (SEQ ID NO 14924). An example of antisense oligonucleotides include a sequence at least about 80%, 85%, 90%, 95%, or 100% identical to a sequence selected from SEQ ID NOs: 12562-14922.

In some embodiments, the antisense oligonucleotides bind to one or more segments of long-form thymic stromal lymphopoietin (1fTSLP) polynucleotides and modulate the expression and/or function of 1fTSLP. In some cases, the segments comprise at least five consecutive nucleotides of the 1fTSLP sense or antisense polynucleotides.

In some embodiments, the antisense oligonucleotides bind to one or more segments of short-form thymic stromal lymphopoietin (sfTSLP) polynucleotides and modulate the expression and/or function of sfTSLP. In some cases, the segments comprise at least five consecutive nucleotides of the sfTSLP sense or antisense polynucleotides.

Since the translation initiation codon is typically 5'-AUG (in transcribed mRNA molecules; 5-ATG in the corresponding DNA molecule), the translation initiation codon may be referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, in some cases, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In some embodiments, "start codon" and "translation initiation codon" refer to the codon or codons that are used in vivo to initiate translation of an mRNA transcribed from a gene encoding long-form thymic stromal lymphopoietin, (1fTSLP), regardless of the sequence(s) of such codons. In some cases, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

In some embodiments, the terms "start codon region" and "translation initiation codon region" refer to a portion of such an mRNA or gene that encompasses from about 25 to about 50 contiguous nucleotides in either direction (i.e., 5' or 3') from a translation initiation codon. In some cases, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds described herein.

The open reading frame (ORF) or "coding region," which is known in the art to refer to the region between the translation initiation codon and the translation termination codon, is also a region which may be targeted effectively. In some embodiments, a targeted region is the intragenic region encompassing the translation initiation or termination codon of the open reading frame (ORF) of a gene.

Another target region includes the 5' untranslated region (5'-UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'-UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5-most residue of the mRNA via a 5-5' triphosphate linkage. The 5' cap region of an mRNA is considered to include the 5' cap structure itself as well as the first 50 nucleotides adjacent to the cap site. Another target region is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In some embodiments, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In some embodiments, the antisense oligonucleotides bind to coding and/or non-coding regions of a target polynucleotide and modulate the expression and/or function of the target molecule.

In some embodiments, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In some embodiments, the types of variants described herein are also embodiments of target nucleic acids.

In some embodiments, the locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments. Additional target segments are readily identifiable by one having ordinary skill in the art in view of this disclosure.

Target segments 5-100 nucleotides in length comprising a stretch of at least five (5) consecutive nucleotides selected from within illustrative target segments are considered to be suitable for targeting as well.

In some embodiments, target segments can include DNA or RNA sequences that comprise at least the 5 consecutive nucleotides from the 5'-terminus of one of the target segments (the remaining nucleotides being a consecutive stretch of the same DNA or RNA beginning immediately upstream of the 54erminus of the target segment and continuing until the DNA or RNA contains about 5 to about 100 nucleotides). In some cases, target segments are represented by DNA or RNA sequences that comprise at least the 5 consecutive nucleotides from the 3'-terminus of one of the target segments (the remaining nucleotides being a consecutive stretch of the same DNA or RNA beginning immediately downstream of the 3'-terminus of the target segment and continuing until the DNA or RNA contains about 5 to about 100 nucleotides).

Once one or more target regions, segments or sites have been identified, antisense compounds are chosen which are sufficiently complementary to the target, i.e., hybridize sufficiently well and with sufficient specificity, to give the desired effect.

Antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like." In some (chimeric) embodiments, an antisense compound may contain both A- and B-form regions.

In some embodiments, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

In some embodiments, the "target segments" identified herein may be employed in a screen for additional compounds that modulate the expression of long-form thymic stromal lymphopoietin (1fTSLP) polynucleotides. "Modulators" are those compounds that decrease or increase the expression of a nucleic acid molecule encoding 1fTSLP and which comprise at least a 5-nucleotide portion that is complementary to a target segment. The screening method comprises the steps of contacting a target segment of a nucleic acid molecule encoding sense or natural antisense polynucleotides of 1fTSLP with one or more candidate modulators, and selecting for one or more candidate modulators which decrease or increase the expression of a nucleic acid molecule encoding 1fTSLP polynucleotides. Once it is shown that the candidate modulator or modulators are capable of modulating (e.g. either decreasing or increasing) the expression of a nucleic acid molecule encoding 1fTSLP polynucleotides, the modulator may then be employed in further investigative studies of the function of 1fTSLP polynucleotides, or for use as a research, diagnostic, or therapeutic agent.

The target segments may be also be combined with their respective complementary antisense compounds to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In some embodiments, an antisense oligonucleotide targets long-form thymic stromal lymphopoietin (1fTSLP) polynucleotides (e.g. accession number NM_033035.4), variants, alleles, isofolins, homologs, mutants, derivatives, fragments and complementary sequences thereto. In some embodiments, an antisense oligonucleotide targets short-form thymic stromal lymphopoietin (sfTSLP) polynucleotides (e.g. accession number NM 033035.4), variants, alleles, isofolins, homologs, mutants, derivatives, fragments and complementary sequences thereto. In some cases, the oligonucleotide is an antisense molecule.

In some embodiments, the target nucleic acid molecule is not limited to 1fTSLP alone but extends to any of the isoforms, receptors, homologs and the like of 1fTSLP molecules. In some embodiments, the target nucleic acid molecule is not limited to sfTSLP alone but extends to any of the isoforms, receptors, homologs and the like of sfTSLP molecules.

In some embodiments, the oligonucleotides are complementary to or bind to nucleic acid sequences of 1fTSLP transcripts and modulate expression and/or function of 1fTSLP molecules. In some embodiments, the oligonucleotides are complementary to or bind to nucleic acid sequences of sfTSLP transcripts and modulate expression and/or function of sfTSLP molecules.

In some embodiments, oligonucleotides comprise sequences of at least 5 consecutive nucleotides of to modulate expression and/or function of 1fTSLP molecules. In some embodiments, oligonucleotides comprise sequences of at least 5 consecutive nucleotides of to modulate expression and/or function of sfTSLP molecules.

The polynucleotide targets comprise 1fTSLP, including family members thereof, variants of 1fTSLP; mutants of 1fTSLP, including SNPs; noncoding sequences of 1fTSLP; alleles of 1fTSLP; species variants, fragments and the like. The polynucleotide targets comprise sfTSLP, including family members thereof, variants of sfTSLP; mutants of sfTSLP, including SNPs; noncoding sequences of sfTSLP; alleles of sfTSLP; species variants, fragments and the like. In some cases, the oligonucleotide is an antisense molecule.

In some embodiments, the oligonucleotide targeting 1fTSLP polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In some embodiments, targeting of long-form thymic stromal lymphopoietin (1fTSLP) polynucleotides, e.g. SEQ ID NO: 14923 modulate the expression or function of this target. In some embodiments, expression or function is down-regulated as compared to a control.

In some embodiments, targeting of long-form thymic stromal lymphopoietin (1fTSLP) polynucleotides, e.g. SEQ ID NO: 14925 modulate the expression or function of this target. In some embodiments, expression or function is down-regulated as compared to a control.

In some embodiments, targeting of short-form thymic stromal lymphopoietin (sfTSLP) polynucleotides, e.g. SEQ ID NO: 14924 modulate the expression or function of this target. In some embodiments, expression or function is down-regulated as compared to a control.

In some embodiments, antisense compounds comprise sequences set forth as SEQ ID NOS: 9971-12561, 14926 and 14927. These oligonucleotides can comprise one or more modified nucleotides, shorter or longer fragments, modified bonds and the like.

In some embodiments, SEQ ID NOS: 9971-14922, 14926, 14927 comprise one or more LNA nucleotides.

In some embodiments, SEQ ID NOS: 9971-14922, 14926, 14927 comprise one or more UNA nucleotides.

In some embodiments, SEQ ID NOS: 9971-14922, 14926, 14927 comprise one or more GNA nucleotides.

The antisense compounds can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound may comprise from 5 to about 80 nucleotides, and a double-stranded antisense compound (such as a dsRNA, for example) may comprise a sense and an antisense strand or portion of 5 to about 80 nucleotides in length. One of ordinary skill in the art will appreciate that this comprehends antisense portions of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range there within.

In some embodiments, the antisense compounds have antisense portions of 10 to 50 nucleotides in length. One having ordinary skill in the art will appreciate that this embodies oligonucleotides having antisense portions of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length.

In some embodiments, the antisense or oligonucleotide compounds have antisense portions of about 12 or 13 to 30 nucleotides in length. One having ordinary skill in the art will appreciate that this embodies antisense compounds having antisense portions of about 12, 13, 14, 15, 16, 17, 18, 19, 20, 21, 22, 23, 24, 25, 26, 27, 28, 29 or 30 nucleotides in length, or any range there within.

In some embodiments, the oligomeric compounds also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, the antisense oligonucleotides, such as for example, nucleic acid molecules set forth in SEQ ID NOS: 9971-14922, 14926, 14927 comprise one or more substitutions or modifications. In some embodiments, the nucleotides are substituted with locked nucleic acids (LNA).

In some embodiments, the oligonucleotides target one or more regions of the nucleic acid molecules sense and/or antisense of coding and/or non-coding sequences associated with 1fTSLP and the sequences set forth as SEQ ID NO: 14923. The oligonucleotides are also targeted to overlapping regions of SEQ ID NOS: 14923 and 14924.

In some embodiments, oligonucleotides disclosed herein are chimeric oligonucleotides. "Chimeric oligonucleotides" or "chimeras," are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In some embodiments, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide target pair, which is the temperature at which the oligonucleotide and target dissociate; dissociation is detected spectrophotometrically. The higher the Tm, the greater is the affinity of the oligonucleotide for the target.

Chimeric antisense compounds may be formed as composite structures of two or more oligonucleotides, modified oligonucleotides, oligonucleosides and/or oligonucleotides mimetics as described above. Such; compounds have also been referred to in the art as hybrids or gapmers.

In some embodiments, the composition comprises an oligonucleotide that targets TSLP, wherein the oligonucleotide comprises an antisense oligonucleotide (ASO). In some embodiments, the oligonucleotide targets 1fTSLP. In some embodiments, the oligonucleotide targets sfTSLP. An ASO is a single-stranded or double-stranded oligonucleotide compound, or analog, variant, mimic, or mimetic thereof, having a sequence that is at least six nucleotides long and is designed to hybridize to a nucleic acid transcript via the binding, partially or wholly, of such compound to the nucleic acid transcript. In some embodiments, the ASO is double stranded. In some embodiments the ASO comprises an siRNA. In some embodiments, the ASO comprises an oligonucleotide other than an siRNA. In some embodiments, the ASO is single stranded.

In some embodiments, the ASO is 12-30 nucleosides in length. In some embodiments, the ASO is 14-30 nucleosides in length. In some embodiments the ASO is single-stranded and 12-30 nucleosides in length. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length. In some embodiments, the ASO is double stranded. In some embodiments the ASO comprises an siRNA. In some embodiments, the ASO comprises an oligonucleotide other than an siRNA. In some embodiments, the ASO is single stranded.

In some embodiments, the composition comprises an oligonucleotide that targets 1fTSLP, wherein the oligonucleotide comprises an ASO comprising an antisense strand about 12-30 nucleosides in length and comprising a nucleoside sequence comprising about 12-30 contiguous nucleosides of one of SEQ ID NO: 14923. In some embodiments the ASO is single-stranded and 12-30 nucleosides in length and comprising a nucleoside sequence comprising about 12-30 contiguous nucleosides of one of SEQ ID NO: 14923. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length. In some embodiments, the ASO is double stranded. In some embodiments the ASO comprises an siRNA. In some embodiments, the ASO comprises an oligonucleotide other than an siRNA. In some embodiments, the ASO is single stranded.

In some embodiments, the composition comprises an oligonucleotide that targets TSLP, wherein the oligonucleotide comprises an ASO comprising an antisense strand about 12-30 nucleosides in length and comprising a nucleoside sequence comprising about 12-30 contiguous nucleosides of one of SEQ ID NO: 14925 In some embodiments, the ASO is 12-30 nucleosides in length. In some embodiments, the ASO is 14-30 nucleosides in length. In some embodiments the ASO is single-stranded and 12-30 nucleosides in length. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length. In some embodiments, the ASO is double stranded. In some embodiments the ASO comprises an siRNA. In some embodiments, the ASO comprises an oligonucleotide other than an siRNA. In some embodiments, the ASO is single stranded.

In some embodiments, the composition comprises an oligonucleotide that targets sfTSLP, wherein the oligonucleotide comprises an ASO comprising an antisense strand about 12-30 nucleosides in length and comprising a nucleoside sequence comprising about 12-30 contiguous nucleosides of one of SEQ ID NO: 14924. In some embodiments the ASO is single-stranded and 12-30 nucleosides in length and comprising a nucleoside sequence comprising about 12-30 contiguous nucleosides of one of SEQ ID NO: 14924. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length. In some embodiments, the ASO is double stranded. In some embodiments the ASO comprises an siRNA. In some embodiments, the ASO comprises an oligonucleotide other than an siRNA. In some embodiments, the ASO is single stranded.

In some embodiments, the composition comprises an oligonucleotide that targets 1fTSLP, wherein the oligonucleotide comprises an ASO, wherein the ASO comprises a nucleoside sequence comprising or consisting of the sequence of any one of SEQ ID NOs: 9971-12561. In some embodiments the ASO comprises a nucleoside sequence comprising or consisting of the sequence of any one of SEQ ID NOs: 9971-12561, or a nucleic acid sequence thereof having 1 or 2 nucleoside substitutions, additions, or deletions. In some embodiments the ASO comprises a nucleoside sequence comprising or consisting of the sequence of any one of SEQ ID NOs: 9971-12561, or a nucleic acid sequence thereof having 3 or 4 nucleoside substitutions, additions, or deletions.

In some embodiments, the composition comprises an oligonucleotide that targets sfTSLP, wherein the oligonucleotide comprises an ASO, wherein the ASO comprises a nucleoside sequence comprising or consisting of the sequence of any one of SEQ ID NOs: 12562-14922. In some embodiments the ASO comprises a nucleoside sequence comprising or consisting of the sequence of any one of SEQ ID NOs: 12562-14922, or a nucleic acid sequence thereof having 1 or 2 nucleoside substitutions, additions, or deletions. In some embodiments the ASO comprises a nucleoside sequence comprising or consisting of the sequence of any one of SEQ ID NOs: 12562-14922, or a nucleic acid sequence thereof having 3 or 4 nucleoside substitutions, additions, or deletions.

Antisense Compound Modifications

In some embodiments, one or more nucleotides in an antisense compound are modified.

In some embodiments, the region of the oligonucleotide which is modified comprises at least one nucleotide modified at the 2' position of the sugar, e.g., a 2'-Oalkyl, 2,—O-alkyl-O-alkyl or 2'-fluoro-modified nucleotide. In some embodiments, RNA modifications include 2'-fluoro, 2'-amino and 2' O-methyl modifications on the ribose of pyrimidines, abasic residues or an inverted base at the 3' end of the RNA. Such oligonucleotides may have a higher Tm (i.e., higher target binding affinity) than 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In some embodiments, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotides contain at least one phosphorothioate modification. In some cases, oligonucleotide modifications which enhance target binding affinity are also, independently, able to enhance nuclease resistance.

Specific examples of some oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. In some cases, an oligonucleotide comprises a phosphorothioate backbone. In some cases, an oligonucleotide comprises heteroatom backbones, particularly $CH_2$—NH—O—$CH_2$, CH, ~N(CH3)—O~CH2 [known as a methylene(methylimino) or MM backbone], CH2—O~N ($CH_3$)~CH2, CH2—N (CH3)—N (CH3)~CH2 and O—N (CH3)—$CH_2$—$CH_2$ backbones, wherein the native phosphodiester backbone is represented as O—P—O—CH,). In some cases, an oligonucleotide comprises a morpholino backbone structures. In some embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. In some cases, oligonucleotides comprise one of the following at the 2' position: OH, SH, SCH3, F, OCN, $OCH_3$ OCH3, $OCH_3$ O($CH_2$)n CH3, O(CH2)n NH2 or O($CH_2$)n CH3 where n is from 1 to about 10; CI to CIO lower alkyl, alkoxyalkoxy, substituted lower alkyl, alkaryl or aralkyl; CI; Br; CN; CF3; OCF3; 0~, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A non-limiting exemplary modification includes 2'-methoxyethoxy-O—$CH_2$ $CH_2$ $OCH_3$, also known as 2'-O-(2-methoxyethyl). Other exemplary modifications include 2'-methoxy (2'-O—$CH_3$), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), mymine (T), cytosine (C) and uracil (U). Modified nucleotides include nucleotides found only infrequently or transiently in natural nucleic acids, e.g., hypoxanthine, 6-methyladenine, 5-Me pyrirnidines, particularly 5-methylcytosine (also referred to as 5-methyl-2' deoxycytosine and often referred to in the art as 5-Me—C), 5-hydroxymethylcytosine glycosyl HMC and gentobiosyl HMC, as well as synthetic nucleotides, e.g., 2-aminoadenine, 2-(methylamino)adenine, 2-(imidazolylalkyl)adenine, 2-(aminoalkyamino)adenine or other heterosubstituted alkyladenines, 2-thiouracil, 2-tmothvmine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. and are suitable base substitutions.

Another modification of the oligonucleotides involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyamine or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. Oligonucleotides may be chimeric oligonucleotides, e.g., as hereinbefore defined.

In some embodiments, the nucleic acid molecule is conjugated with a moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amiditcs and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In some embodiments, use of modifications such as the use of LNA monomers to enhance the potency, specificity and duration of action and broaden the routes of administration of oligonucleotides comprised of current chemistries such as MOE, ANA, FAN A, PS etc. This can be achieved by substituting some of the monomers in the current oligonucleotides by LNA monomers. The LNA modified oligonucleotide may have a size similar to the parent compound or may be larger or smaller. In some cases, such LNA-modified oligonucleotides contain less than about 70%, less than about 60%, or less than about 50% LNA monomers, and that their sizes are between about 5 and 25 nucleotides, or between about 12 and 20 nucleotides.

In some embodiments, modified oligonucleotide backbones comprise, but are not limited to, phosphorothioates, chiral phosphorothioates, phosphorodithioates, phosphotriesters, aniinoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3-5' linkages, 2-5' linked analogs of these, and those having inverted polarity wherein the adjacent pairs of nucleoside units are linked 3'-5' to 5'-3' or 2'-5' to 5'-2. Various salts, mixed salts and free acid forms are also included.

In some embodiments, modified oligonucleotide backbones that do not include a phosphorus atom therein have backbones that are formed by short chain alkyl or cycloalkyl intenucleoside linkages, mixed heteroatom and alkyl or cycloalkyl internucleoside linkages, or one or more short chain heteroatomic or heterocyclic intenucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In some embodiments, both the sugar and the internucleoside linkage, i.e., the backbone, of the nucleotide units are replaced with novel groups while the base units are maintained for hybridization with the target nucleic acid. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

In some embodiments, the oligonucleotides comprise a heteroatom backbone, e.g., —$CH_2$—NH—O—$CH_2$—, —$CH_2$—N ($CH_3$)—O—$CH_2$— known as a methylene (memylimino) or MMI backbone, —$CH_2$—O—N ($CH_3$)—$CH_2$—, —$CH_2$N($CH_3$)—N($CH_3$) $CH_2$—, and —O—N ($CH_3$)—$CH_2$—$CH_2$—, wherein the native phosphodiester backbone is represented as —O—P—O—$CH_2$—O. In some embodiments, oligonucleotides comprise morpholino backbone structures.

Modified oligonucleotides may also contain one or more substituted sugar moieties. In some embodiments, oligonucleotides comprise one of the following at the 2' position: OH; F; O—, S—, or N-alkyl; O—, S—, or N-alkenyl; O—, S- or N-alkynyl; or O alkyl-O-alkyl, wherein the alkyl, alkenyl and alkynyl may be substituted or unsubstituted C to CO alkyl or C2 to CO alkenyl and alkynyl. Non-limiting examples are $O(CH_2)n$ OmCH3, $O(CH_2)n$, OCH3, $O(CH_2)$nNH2, $O(CH_2)$nCH3, $O(CH_2)$nONH2, and $O(CH_2$nON$(CH_2)$nCH3)2 where n and m can be from 1 to about 10. In some embodiments, oligonucleotides comprise one of the following at the 2' position: C to CO, (lower alkyl, substituted lower alkyl, alkaryl, aralkyl, O-alkaryl or O-aralkyl, SH, SCH3, OCN, CI, Br, CN, CF3, OCF3, SOCH3, SO2CH3, ONO2, NO2, N3, NH2, heterocycloalkyl, heterocycloalkaryl, ammoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. An exemplary modification comprises 2'-methoxyethoxy (2'-O—$CH_2CH_2OCH3$, also known as 2'-O-(2-methoxyethyl) or 2'-MOE) i.e., an alkoxyalkoxy group. Another exemplary modification comprises 2'-dimethylaminooxyethoxy, i.e., a $O(CH_2)2ON(CH_3)2$ group, also known as 2-DMAOE, as described in examples herein below, and 2'-dimemylaminoethoxyethoxy (also known in die art as 2'-O-dimethylaminoethoxyethyl or 2'-DMAEOE), i.e., 2'-O—$CH_2$—O—$CH_2$—N($CH_2$)2.

Another exemplary modification comprises 2-methoxy (2-O CH3), 2'-aminopropoxy (2'-O—$CH_2CH_2CH_2NH2$) and 2-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobut 1 moieties in place of the pentofuranosyl sugar.

Oligonucleotides may also comprise nucleobase (often referred to in the art simply as "base") modifications or substitutions. In some embodiments, as used herein, "unmodified" or "natural" nucleotides comprise the purine bases adenine (A) and guanine (G), and the pyrimidine bases mymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazgnanine and 7-deazaadenine and 3-deazaguanine and 3-deazaadenine.

Certain nucleotides may be particularly useful for increasing the binding affinity of the oligomeric compounds. In some cases, these comprise 5-substituted pyrimidines, 6-azapyrirnidines and N-2, N-6 and 0-6 substituted purines, comprising 2-aminopropyladenine, 5-propynyluracil and/or 5-propynylcytosine. 5-methylcytosine substitutions have been shown to increase nucleic acid duplex stability by 0.6-1.2° C., even more particularly when combined with 2'-Omethoxyethyl sugar modifications.

Another modification of the oligonucleotides involves chemically linking to the oligonucleotide one or more moieties or conjugates, which may enhance the activity, cellular distribution, or cellular uptake of the oligonucleotide. Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

In some embodiments, the composition comprises an oligonucleotide that inhibits the expression of 1fTSLP, wherein the oligonucleotide comprises an ASO, wherein the ASO comprises a nucleoside sequence comprising or consisting of the sequence of any one of SEQ ID NOs: 23299-25889. In some embodiments, the ASO comprises a nucleoside sequence comprising or consisting of the sequence of any one of SEQ ID NOs: 23299-25889, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 23299-25889, or a nucleic acid sequence thereof having 3 or 4 nucleoside substitutions, additions, or deletions.

In some embodiments, the composition comprises an oligonucleotide that inhibits the expression of 1fTSLP, wherein the oligonucleotide comprises an ASO, wherein the ASO comprises modification pattern: 5'-nsnsnsnsnsdNsdNsdNsdNsdNsdNsdNsdNsdNsdNsnsnsn snsn-3' (SEQ ID NO: 34506) where "dN" is any deoxynucleotide, "n" is a 2'O-methyl or 2'O-methoxyethyl-modified nucleoside, and "s" is a phosphorothioate linkage.

In some embodiments, the composition comprises an oligonucleotide that inhibits the expression of sfTSLP, wherein the oligonucleotide comprises an ASO, wherein the ASO comprises modification pattern: 5'-nsnsnsnsnsdNsdNsdNsdNsdNsdNsdNsdNsdNsdNsnsnsn snsn-3' (SEQ ID NO: 34506) where "dN" is any deoxynucleotide, "n" is a 2'O-methyl or 2'O-methoxyethyl-modified nucleoside, and "s" is a phosphorothioate linkage.

In some embodiments, the ASO comprises any one of modification patterns 1S, 2S, 3S, 4S, 5S, 1AS, 2AS, 3AS, or 4AS. In some embodiments, the modification or modification pattern provides nuclease resistance to the ASO.

Ligands

A wide variety of entities can be coupled to the oligonucleotides described herein. In some embodiments, the entities are ligands, which are coupled, e.g., covalently, either directly or indirectly via an intervening tether. In some embodiments, a ligand is coupled to a dsRNA agent. In some embodiments, a ligand is coupled to an antisense compound.

In some embodiments, a ligand alters the distribution, targeting or lifetime of the molecule into which it is incorporated. In some embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhc-«Jamines, coumarins, and dyes. Groups that enhance the pharmacodynamic properties include groups that improve uptake, enhance resistance to degradation, and or strengthen sequence-specific hybridization with the target nucleic acid. Groups that enhance the pharmacokinetic properties include groups that improve uptake, distribution, metabolism or excretion of the compounds herein. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or Adamantane acetic acid, a palmityl moiety, or an octadecylamine or hexylamino-carbonyl-oxycholesterol moiety. Oligonucleotides may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzolhiadiazide, chlorothiazide, a diazepine, indomethicin, a barbiturate, a cephalosporin, a sulfa drug, an antidiabetic, an antibacterial or an antibiotic.

Some ligands can have endosomolytic properties. The endosomolytic ligands promote the lysis of the endosome and/or transport of the composition, or its components, from the endosome to the cytoplasm of the cell. The endosomolytic ligand may be a polyanionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/ or transport of the composition, or its components, from the endosome to the cytoplasm of the cell. Exemplary endosomolytic ligands include the GALA peptide, the EALA peptide, and their derivatives. In some embodiments, the endosomolytic component may contain a chemical group (e.g., an amino acid) which will undergo a change in charge or protonation in response to a change in pH. The endosomolytic component may be linear or branched. Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrenemaleic acid anhydride copolymer, poly(L-lactide-co-glycolied) copolymer, divinyl ether-maleic anhydride copolymer, N-(2-hydroxypropyl)methacrylamide copolymer (RMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Additional examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-KB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNF alpha), interleukin-1 beta, or gamma interferon.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL). In another aspect, the ligand is a cell-permeation agent, e.g., a helical cell-permeation agent. In some cases, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is may be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF derived from human fibroblast growth factor 4 and having the amino acid sequence AAVALLPAVLLALLAP (SEQ ID NO: 34498) An RFGF analogue (e.g., amino acid sequence AALLPVLLAAP (SEQ ID NO: 34499) containing a hydrophobic MTS can also be a targeting moiety. The peptide moiety can be a "delivery" peptide, which can carry large polar molecules including peptides, oligonucleotides, and protein across cell membranes. For example, sequences from the HW Tat protein (GRKKRRQRRRPPQ (SEQ ID NO: 34500)) and the Drosophila Antennapedia protein (RQIKIWFQNRRMKWK (SEQ ID NO: 34501)) have been found to be capable of functioning as delivery peptides. A peptide or peptidomimetic can be encoded by a random sequence of DNA, such as a peptide identified from a phage-display library, or one-bead-one-compound (OBOC) combinatorial library. In some cases, the peptide or peptidomimetic tethered to an antisense oligonucleotide or iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell. An RGD peptide can facilitate targeting of an iRNA agent to tumors of a variety of other tissues, including the lung, kidney, spleen, or liver. In some cases, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing yB3. Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Exemplary conjugates of this type ligands that targets PECAM-1, VEGF, or other cancer gene, e.g., a cancer gene described herein.

In some embodiments, a "cell permeation peptide" is capable of permeating a cell, e.g., a microbial cell, such as a bacterial or fungal cell, or a mammalian cell, such as a human cell. A microbial cell-permeating peptide can be, for example, an a-helical linear peptide (e.g., LL-37 or Ceropin PI), a disulfide bond-containing peptide (e.g., a-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen.

In some embodiments, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H2A peptides, Xenopus peptides, esculentinis-1, and caerins. A number of factors may be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable as ligands (e.g. as PK modulating ligands).

In addition, aptamers that bind serum components (e.g. serum proteins) are also amenable as PK modulating ligands.

When two or more ligands are present, the ligands can all have same properties, all have different properties or some ligands have the same properties while others have different properties. For example, a ligand can have targeting properties, have endosomolytic activity or have PK modulating properties. In some embodiments, all the ligands have different properties.

Ligands can be coupled to the oligonucleotides at various places, for example, 3'-end, 5'-end, and/or at an internal position. In some embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-(CH$_2$)nNH2 may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether. In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In some embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The F position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide. Linkers that conjugate the ligand to the nucleic acid include those discussed above. For example, the ligand can be one or more GalNAc (N-acetylglucosamine) derivatives attached through a bivalent or trivalent branched linker.

Cleavable Linking Groups

In some embodiments, an oligonucleotide compound or composition comprising an oligonucleotide compound comprises a cleavable linking group. In some cases a dsRNA agent comprises or is connected to a cleavable linking group. In some cases an antisense compound comprises or is connected to a cleavable linking group.

In some embodiments, a cleavable linking group is one which is sufficiently stable outside the cell, but which upon entry into a target cell is cleaved to release the two parts the linker is holding together. In some embodiments, the cleavable linking group is cleaved at least 10 times or more, or at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative agents. Generally, cleavage agents are more prevalent or found at higher levels or activities inside cells than in serum or blood.

Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a particular pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes. In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In some embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In some embodiments, candidate compounds are cleaved by at most 10% in the blood. In some embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Some embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. An exemplary embodiment is —O—P(O)(OH)—O—. These candidates can be evaluated using methods analogous to those described above.

Acid Cleavable Linking Groups

Acid cleavable linking groups are linking groups that are cleaved under acidic conditions. In some embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—C(O)O, or —OC(O). An exemplary embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C5 and above (e.g., C5-C8) sugars; di- and trisaccharides include sugars having two or three monosaccharide units (e.g., C5-C8).

Nucleotide Mimics

In some embodiments, an oligonucleotide disclosed herein is a naked oligonucleotide. Naked oligonucleotides are defined as systems that contain no agents that are associated with the nucleic acid either covalently or non-covalently. The absence of any delivery vehicle may require that the oligonucleotide itself be sufficiently nuclease resistant, sufficiently long circulating and cell targeted. For small, solid-phase synthesized oligonucleotides such as those used in antisense oligonucleotides, RNAi, and innate immune stimulators, the use of nucleotide mimics may provide the required drug-like properties.

In some embodiments, an oligonucleotide of the present disclosure comprises nucleotides that replace phosphodiester group. The substitution of one non-bridging oxygen of a phosphodiester with a sulfur atom creates the phosphorothioate (PS) linkage. A PS bond creates a new stereocenter in the nucleotide and when synthesized under standard achiral conditions creates diastereomeric mixtures of Rp and Sp at the phosphorous atom.

There are other functional groups that have been identified as replacements of the phosphodiester group in the oligonucleotide. Like phosphates and phosphorothioates, there are a variety of functional groups that are negatively charged such as phosphorodithioate (PS2) and thio-phosphoramidates. There are number of analogues that are uncharged such as phosphorodiamidate morpholino oligomer (PMO), peptide nucleic acid (PNA), phosphotriesters, and phosphonates. It has been postulated that the uncharged analogues are not only nuclease resistant, but may also be more membrane permeable; however, the size and hydrophilicity of uncharged oligonucleotides still preclude their passive diffusion across membranes.

Morpholino oligos (PMOs) use a hydrolytically stable, uncharged phosphordiamidate functional group.

Peptide nucleic acids (PNAs) are—as their name suggests—based upon the amide functional group.

Enemas and intramuscular, intravitreal, intrathecal injections have been used for the administration of a variety of oligonucleotides with and without PS bonds.

In some embodiments, an oligonucleotide of the present disclosure comprises a nucleoside analogue that alters the structure of ribose. There are a variety of nucleotide mimics wherein the ribose or deoxyribose is modified to increase affinity for target and/or increase nuclease resistance. In some cases, there are modifications to all five positions of the ribose ring. In some cases, modifications are made to the 2' position of ribose.

In some embodiments, an oligonucleotide of the present disclosure comprises a modifications at the 1' position. In some cases, the oligonucleotide comprises a cytidine mimic that is designed to have increased affinity for guanosine bases due to hydrogen bonding through an aminoethyl group. In some cases, the oligonucleotide comprises a C-5 propynyl pyrimidines.

In some embodiments, an oligonucleotide of the present disclosure comprises a 2' modifications. Modifications of the hydroxyl group at the 2' position of ribose may be used to mimic the structure of the ribose ring while inhibiting ribonucleases that require the 2'OH group for hydrolysis of RNA. In some cases, the oligonucleotide comprises a 2'-O-Methyl ribonucleic acid that is naturally occurring and may increase binding affinity to RNA itself while being resistant to ribonuclease. In some cases, the oligonucleotide comprises a 2'-O-Methyl group. In some cases, the oligonucleotide comprises a 2'-O-Methoxyethyl(MOE) modification, which may mimic the ribonuclease resistance of 0-methyl, attenuate protein-oligonucleotide interactions and have increased affinity for RNA.

In some embodiments, an oligonucleotide of the present disclosure comprises a 2'-deoxy-2'-fluoro (2'-F) analogue of nucleosides that adopt a C3'-endo conformation characteristic of the sugars in RNA helices.

In some embodiments, an oligonucleotide of the present disclosure comprises a 4'- and 5'-modifications, where alkoxy substituents at the 4' position of 2'deoxyribose mimic the conformation of ribose.

In some embodiments, an oligonucleotide of the present disclosure comprises a bicyclic 2'-4'-modification. There are a variety of ribose derivatives that lock the carbohydrate ring into the 3' endo conformation by the formation of bicyclic structures with a bridge between the 2' oxygen and the 4' position. The original bicyclic structure has a methylene bridging group and are termed locked nucleic acids (LNAs).

The bicyclic structure "locks" the ribose into its preferred 3' endo conformation and increases base pairing affinity. It has been shown the that incorporation of LNAs into a DNA duplex can increase melting points up to 8° C. per LNA. Subsequently, a variety of bicyclic nucleotides have been developed such as Bridged Nucleic Acids (BNAs), Ethyl-bridged (ENAs), constrained ethyl (cEt) nucleic acids and tricyclic structures with varying affinity for target sites. LNAs can be incorporated into antagomirs, splice blocking oligonucleotides, either strand of an RNAi duplex; however, like other 3' endo conformers, LNAs are not substrates for RNAse H.

In some embodiments, an oligonucleotide of the present disclosure comprises an acyclic nucleic acid analog. In some cases, the analog comprises an alternative ribose ring structure. These include those in which the bond between 2' and 3' carbons in the ribose is absent, as well as those containing substitution of the ribose ring with a three-carbon backbone. Examples of acyclic nucleic acid analogs include unlocked nucleic acid (UNA) and glycol nucleic acids (GNA). Incorporation of these analogs reduce the melting temperature of the RNAi duplex and can be incorporated into either strand. Incorporation at the 5' end of the sense strand, or passenger strand, inhibits incorporation into this strand into RISC. Incorporation into the seed region of the antisense strand, or guide strand, can reduce off-target activity. Acyclic nucleic acid analogs may also increase resistance of the RNAi duplex to 3'-exonuclease activity.

In some embodiments, an oligonucleotide of the present disclosure comprises a modification patterns. Without being bound by theory, for RNAi duplexes, recognition by RISC requires RNA-like 3'-endo nucleotides and some patterns of RNA analogues. A pattern of alternating 2'-O-methyl groups may provide stability against nucleases, but not all permutations of alternating 2'-O-methyl are active RNAi agents. The fact that one may remove all 2'-hydroxy groups with alternating 2'-fluoro and 2'-O-methyl groups to produce duplexes that are resistant to nucleases and active in RNAi may suggest the 2'-hydroxy group is not absolutely required for activity, but that some sites in the RNAi duplex are sensitive to the added steric bulk of the methyl group.

Conjugated Oligonucleotides

Oligonucleotides may have groups conjugated via covalent bonds that prolong circulation, provide targeting to tissues and facilitate intracellular delivery.

In some embodiments, an oligonucleotide of the present disclosure is conjugated to polyethylene glycol (PEG), which may prevent clearance by two mechanisms: the increase in molecular weight above threshold for renal clearance and the prevention of non-specific interactions with extracellular surfaces and serum components. PEG may be incorporated into nucleic acid delivery vehicles by attachment to components that non-covalently associate with the nucleic acids, e.g. PEGylated lipids and polymers. PEG may also be directly conjugated to increase nucleic acid circulation times, decrease nonspecific interactions and alter biodistribution. In some cases, the targeting is passive and the potency of the nucleic may be compromised as PEG MW increases.

Another class of molecules that can be conjugated in order to increases circulation times is the attachment of lipophilic groups such as cholesterol or other lipophilic moiety with >12 carbons which interact with serum components such as albumen and lipoproteins thereby increasing circulation times and passive accumulation in the liver. In some cases, extensive PS modification increases circulation times through associations with serum components, with roughly 10 PS groups required for serum binding.

Formulations, Compositions, and Delivery

In some embodiments, the antisense oligonucleotide or dsRNA is administered in buffer.

In some embodiments, antisense oligonucleotide or dsRNA agent (sometimes referred to as siRNA) compounds described herein can be formulated for administration to a subject. A formulated anti sense oligonucleotide or siRNA composition can assume a variety of states. In some examples, the composition is at least partially crystalline, uniformly crystalline, and/or anhydrous (e.g., less than 80, 50, 30, 20, or 10% water). In another example, the antisense oligonucleotide or siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the antisense oligonucleotide or siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly. In some embodiments, the composition is formulation for administration by inhalation.

An antisense oligonucleotide or siRNA preparation can be formulated in combination with another agent, e.g., another therapeutic agent or an agent that stabilizes an antisense oligonucleotide or siRNA, e.g., a protein that complexes with siRNA to form an iRNP. Still other agents include chelators, e.g., EDTA (e.g., to remove divalent cations such as Mg2+), salts, RNAse inhibitors (e.g., a broad specificity RNAse inhibitor such as RNAsin) and so forth.

In some embodiments, the antisense oligonucleotide or siRNA preparation includes another antisense oligonucleotide or siRNA compound, e.g., a second siRNA that can mediate RNAi with respect to a second gene, or with respect to the same gene. Still other preparation can include at least 3, 5, ten, twenty, fifty, or a hundred or more different antisense oligonucleotide or siRNA species. Such siRNAs can mediate RNAi with respect to a similar number of different genes.

In some embodiments, the antisense oligonucleotide or siRNA preparation includes at least a second therapeutic agent (e.g., an agent other than a RNA or a DNA). For example, an antisense oligonucleotide or siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Liposomes

For ease of exposition the formulations, compositions and methods in this section are discussed largely with regard to unmodified antisense oligonucleotide or siRNA compounds. It may be understood, however, that these formulations, compositions and methods can be practiced with other antisense oligonucleotide or siRNA compounds, e.g., modified antisense oligonucleotide or siRNAs. An antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. In some embodiments, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the antisense oligonucleotide or siRNA composition. The lipophilic material isolates the aqueous interior from an aqueous exterior, which typically does not include the antisense oligonucleotide or siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the antisense oligonucleotide or siRNA are delivered into the cell where the antisense oligonucleotide or siRNA can specifically bind to a target RNA. In some cases the liposomes are also specifically targeted, e.g., to direct the antisense oligonucleotide or siRNA to particular cell types.

A liposome containing an antisense oligonucleotide or siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The antisense oligonucleotide or siRNA preparation is then added to the micelles that include the lipid component. The cationic groups on the lipid interact with the antisense oligonucleotide or siRNA and condense around the anti sense oligonucleotide or siRNA to form a liposome. After condensation, the detergent is removed, e.g., by dialysis, to yield a liposomal preparation of antisense oligonucleotide or siRNA.

If necessary, a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Commonly used techniques for preparing lipid aggregates of appropriate size for use as delivery vehicles include sonication and freeze-thaw plus extrusion. Microfluidization can be used when consistently small (50 to 200 nm) and relatively uniform aggregates are desired. These methods are readily adapted to packaging antisense oligonucleotide or siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs.

Nevertheless, some nucleic acid molecules are entrapped within the aqueous interior of these liposomes. pH-sensitive liposomes have been used to deliver DNA encoding the thymidine kinase gene to cell monolayers in culture where expression of the exogenous gene was detected in the target cells.

One type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver antisense oligonucleotide or siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated antisense oligonucleotide or siRNAs in their internal compartments from metabolism and degradation. Some considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA.

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES").

Another cationic lipid conjugate includes derivatization of the lipid with cholesterol ("DC-Choi") which may be formulated into liposomes in combination with DOPE. Lipopolylysine, made by conjugating polylysine to DOPE, may be effective for transfection in the presence of serum. For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Md.).

Liposomal formulations may be particularly suited for topical administration, and may present an advantage over other formulations. Such advantages include reduced side effects related to high systemic absorption of the administered drug, increased accumulation of the administered drug at the desired target, and the ability to administer antisense oligonucleotide or siRNA, into the skin. In some implementations, liposomes are used for delivering antisense oligonucleotide or siRNA to epidermal cells and also to enhance the penetration of antisense oligonucleotide or siRNA into dermal tissues, e.g., into skin. For example, the liposomes can be applied topically.

In some embodiments, non-ionic liposomal systems are used to deliver an oligonucleotide to the skin, e.g., using non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) may be used to deliver an oligonucleotide. Such formulations with antisense oligonucleotide or siRNA are useful for treating a dermatological disorder.

Liposomes that include antisense oligonucleotide or siRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include antisense oligonucleotide or siRNA can be delivered, for example, subcutaneously by infection in order to deliver antisense oligonucleotide or siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

In some embodiments, an oligonucleotide is formulated with a surfactant. Surfactants find wide application in formulations such as emulsions (including microemulsions) and liposomes (see above). In some embodiments, the antisense oligonucleotide or siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides a useful means for categorizing the different surfactants used in formulations.

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class.

The polyoxy ethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfo succinates, and phosphates. The most important members of the anionic surfactant class are the alkyl sulfates and the soaps. If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Micelles and other Membranous Formulations

For ease of exposition the micelles and other formulations, compositions and methods in this section are discussed largely with regard to unmodified antisense oligonucleotide or siRNA compounds. It may be understood, however, that these micelles and other formulations, compositions and methods can be practiced with other antisense oligonucleotide or siRNA compounds, e.g., modified antisense oligonucleotide or siRNA compounds. The antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) composition can be provided as a micellar formulation. In some embodiments, "micelles" are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the antisense oligonucleotide or siRNA composition, an alkali metal Cs to C22 alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxy ethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

Pharmaceutical Compositions

The oligonucleotides disclosed herein may be formulated in a pharmaceutical composition. The specific concentrations of the oligonucleotide can be determined by experimentation.

For ease of exposition the particles, formulations, compositions and methods in this section are discussed largely with regard to antisense oligonucleotide or siRNA compounds. It may be understood, however, that these particles, formulations, compositions and methods can be practiced with modified antisense oligonucleotide or siRNA compounds. In some embodiments, an antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or siRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

The anti sense oligonucleotide or siRNA agents may be formulated for pharmaceutical use. Pharmaceutically acceptable compositions comprise a therapeutically-effective amount of one or more of the antisense oligonucleotide or dsRNA agents in any of the preceding embodiments, taken alone or formulated together with one or more pharmaceutically acceptable carriers (additives), excipient and/or diluents. In dome embodiments, the composition is a pharmaceutical composition.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) inhalation; or (10) endotracheally. In some embodiments, the composition is sterile.

In some embodiments, a "therapeutically-effective amount" is an amount of a compound, material, or composition comprising an oligonucleotide herein which is effective for producing some desired therapeutic effect in at least a sub-population of cells in an animal at a reasonable benefit/risk ratio applicable to any medical treatment.

In some embodiments, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations. In some embodiments, the composition comprises a pharmaceutically acceptable carried. In some embodiments, the pharmaceutically acceptable carriers comprises water, a buffer, or a saline solution.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, from about 5 percent to about 70 percent, or from about 10 percent to about 30 percent.

In certain embodiments, a formulation comprises an excipient selected from the group consisting of cyclodextrins, celluloses, liposomes, micelle forming agents, e.g., bile acids, and polymeric carriers, e.g., polyesters and polyanhydrides; and a compound disclosed herein. In certain embodiments, an aforementioned formulation renders orally bio available a compound disclosed herein.

An agent preparation can be formulated in combination with another agent, e.g., another therapeutic agent or an agent that stabilizes an antisense oligonucleotide or iRNA, e.g., a protein that complexes with antisense oligonucleotide or iRNA to form particle. Still other agents include chelators, e.g., EDTA (e.g., to remove divalent cations such as Mg2+), salts, RNAse inhibitors (e.g., a broad specificity RNAse inhibitor such as RNAsin) and so forth.

Methods of preparing these formulations or compositions include the step of bringing into association a compound disclosed herein with the carrier and, optionally, one or more accessory ingredients. In general, the formulations are prepared by uniformly and intimately bringing into association a compound disclosed herein with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds disclosed herein may be formulated for administration in any convenient way for use in human or veterinary medicine, by analogy with other pharmaceuticals.

Further provided are pharmaceutical compositions of the oligonucleotide molecules described. These pharmaceutical compositions include salts of the above compounds, e.g., acid addition salts, for example, salts of hydrochloric, hydrobromic, acetic acid, and benzene sulfonic acid. These pharmaceutical formulations or pharmaceutical compositions can comprise a pharmaceutically acceptable carrier or diluent.

In some embodiments, pharmaceutical compositions (e.g. oligonucleotides and/or lipid nanoparticle formulations thereof) further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

In some embodiments, the siRNA and LNP compositions and formulations provided herein for use in pulmonary delivery further comprise one or more surfactants. Suitable surfactants or surfactant components for enhancing the uptake of the compositions include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

Aerosol Formulations

The compositions disclosed herein, either alone or in combination with other suitable components, can be made into aerosol formulations (i.e., they can be "nebulized") to be administered via inhalation (e.g., intranasally or intratracheally). Aerosol formulations can be placed into pressurized acceptable propellants, such as dichlorodifluoromethane, propane, nitrogen, and the like.

In some embodiments, the oligonucleotide molecules and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions. A solid particulate composition comprising the oligonucleotide compositions can optionally contain a dispersant which serves to facilitate the formation of an aerosol as well as other therapeutic compounds. A suitable dispersant is lactose, which can be blended with the nucleic acid compound in any suitable ratio.

Spray compositions comprising oligonucleotide molecules can, for example, be formulated as aqueous solutions or suspensions or as aerosols delivered from pressurized packs, such as a metered dose inhaler, with the use of a suitable liquefied propellant. In some embodiments, aerosol compositions suitable for inhalation can be either a suspension or a solution and generally contain an oligonucleotide molecule and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition can optionally contain additional formulation excipients well known in the art such as surfactants. In some embodiments a pharmaceutical aerosol formulation comprising a compound disclosed herein and a fluorocarbon or hydrogen-containing chlorofluorocarbon or mixtures thereof as propellant, optionally in combination with a surfactant and/or a co-solvent.

The aerosol formulations can be buffered by the addition of suitable buffering agents.

Aerosol formulations can include optional additives including preservatives if the formulation is not prepared sterile. Non-limiting examples include, methyl hydroxybenzoate, anti-oxidants, flavorings, volatile oils, buffering agents and emulsifiers and other formulation surfactants. In some embodiments, fluorocarbon or perfluorocarbon carriers are used to reduce degradation and provide safer biocompatible non-liquid particulate suspension compositions (e.g., oligonucleotide and/or lipid nanoparticle formulations thereof). In some embodiments, a device comprising a nebulizer delivers a composition (e.g., oligonucleotide and/or lipid nanoparticle formulations thereof) comprising fluorochemicals that are bacteriostatic thereby decreasing the potential for microbial growth in compatible devices.

Capsules and cartridges comprising the composition for use in an inhaler or insufflator, of for example gelatin, can be formulated containing a powder mix for inhalation of a compound disclosed herein and a suitable powder base such as lactose or starch.

The aerosol compositions can be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In some embodiments, the particulate range can be from 1 to 5 microns. In some embodiments, the particulate range can be from 2 to 3 microns. Particles of non-respirable size which are included in the aerosol tend to deposit in the throat and be swallowed, and the quantity of non-respirable particles in the aerosol is thus minimized. For nasal administration, the particle size may be in the range of 10-500 µm to ensure retention in the nasal cavity.

In some embodiments, an oligonucleotide is administered topically to the nose for example, for the treatment of rhinitis, via pressurized aerosol formulations, aqueous formulations administered to the nose by pressurized pump or by nebulization. Suitable formulations contain water as the diluent or carrier for this purpose. In certain embodiments, the aqueous formulations for administration of the composition to the lung or nose can be provided with conventional excipients such as buffering agents, tonicity modifying agents and the like.

Gene Therapy Vector

In some embodiments, double-stranded RNAi agents or antisense oligonucleotides are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration, or by stereotactic injection. The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA agent and one that produces a transcript that includes the bottom strand of a dsRNA agent. When the templates are transcribed, the dsRNA agent is produced, and processed into siRNA agent fragments that mediate gene silencing.

Delivery Vehicles Based Upon Complexation of Nucleic Acid

In some embodiments, complexation of oligonucleotide therapeutics with cationic agents inhibits nuclease from degrading the oligonucleotide by forming a steric barrier and by inhibiting nuclease binding by neutralizing anionic charge. The process of forming compact particles of nucleic acids from their extended chains is called condensation, which may be achieved by the addition of multiply-charged cationic species. Multiple positive charges can either be covalently attached to one another in a polycation or non-covalently associated with one another in a complex such as the surface of a cationic liposome. The resulting polycation-polyanion interaction is a colloidal dispersion where the nucleic acid particles vary in size and shape depending on the nucleic acid and the condensing cation. In general, the particles are greater than 20 nm in size, and—in the absence of agents to modulate surface charge such as polyethylene glycol (PEG)—have surface charges >20 mV.

The pharmacokinetics and biodistribution of nanoparticles are dependent upon their size and charge. Upon iv administration, large (>200 nm) and/or highly positively charged (surface charge >20 mV) are primarily distributed among endothelial tissues and macrophages in the liver and spleen and have a half-life of circulation less than 2 hours. Reduction in size (<100 nm) and surface charge (~0 mV) results increased circulation times. Local administration of positively charged polyplexes results in association with cells at site of application such as epithelial cells.

Strategies for Cytoplasmic Delivery

There are a variety of strategies to facilitate cytoplasmic delivery of oligonucleotides including endosomal buffering (i.e. proton sponge), titratable amphiphiles, cell penetrating peptides and masked membrane lytic polymers.

The mechanism of endosomal buffering (i.e. proton sponge) to facilitate endosomolysis relies on the ability of agents such as polyamines to buffer endosomal/lysosomal compartments. The resistance to acidification is postulated to result in increased osmotic pressure that results in lysis of the lysosomal compartment. Titratable amphiphiles are polymers/peptides whose structure is pH-dependent in such a way that at acidic pH they are hydrophobic and membrane disruptive. Typically, titratable amphiphiles are polyanionic polymers or peptides composed of carboxylic acids that become neutral and membrane disruptive upon acidification. Cell penetrating peptides (CPPs) are cationic peptides, with a high propensity of guanidinium groups, that enter cells without any apparent membrane lysis. Masked lytic polymers are membrane disruptive polymers whose membrane interactivity is attenuated by reversible covalent modification. Like titratable amphiphiles, the mechanism of endosomolysis by masked polymers relies on the use of amphipathic polymers whose ability to lyse membranes is controlled such that the activity is only functional in the acidic environment of the endosome/lysosome. In the case of titratable amphiphiles, the mechanism of control is a reversible protonation of carboxylic acids. In the case of masked polymers, the control of membrane activity is the irreversible cleavage of a group that inhibits membrane interactivity of the polymer.

Liposomal Delivery Systems

Nucleic acids entrapped in lipids (lipoplexes) are a common vehicle for the delivery of nucleic acids. Cationic lipids form electrostatic complexes between nucleic acid and lipids. In addition to the cationic lipids, there are typically neutral or anionic helper lipids which are composed of unsaturated fatty acids and are postulated to assist in fusion between the lipoplex and the cellular membrane, and PEGylated lipids, which prevent aggregation during formulation and storage and non-specific interactions in vivo.

Lipids are water insoluble and nucleic acids are organic solvent insoluble. To mix these components in a controlled manner such that formulations are repeatable and relatively homogenous in size, detergents or water-miscible organic solvents such as ethanol are used. After formation of electrostatically-associated complexes, the amphipathic detergent or solvent is then removed by dialysis or solvent exchange. Depending on the components and the mixing procedure is possible to formulate lipoplexes that are well less than 100 nm.

Although the transfection efficiencies of lipoplexes are difficult to predict and optimization is empirical, there are a few design features that have been identified to aid transfection efficiency in vivo: pH-sensitive cationic lipids, the use of unsaturation in the lipid chains and the hydrophobic-hydrophilic balance of PEG-lipids to balance circulation times and transfection efficiencies.

There have been several studies that have shown a correlation between the pKa of the amine groups of the cationic lipid, which is buffer in the range of the endosomal/lysosomal pathway (pH 4-7), and transfection ability. To synthesize lipids with such pKa values, lipids commonly have closely-spaced amines or imidazole groups. The effect of these weakly basic amine groups in the lipoplexes produces several attractive attributes that facilitate in vivo transfection: reduced surface charge at neutral pH thereby decreasing nonspecific interactions in vivo, increased surface charge in acid environment of endosomes and lysosomes thereby increasing electrostatic interactions with the cellular membrane in these compartments and providing buffering groups that can provide endosomolytic activity via the proton sponge mechanism.

Another common motif observed in cationic and helper lipids used in lipoplexes is the presence of unsaturation in their component fatty acids with oleic (18 carbon chain with one double bond) and linoleic (18 carbons with 2 double bonds) being very common. The incorporation of these groups increases fluidity of membranes, aids in the formation of fusogenic lipid structures and facilitates the release of cationic lipids from nucleic acids.

PEG-conjugated lipids are incorporated into lipoplexes to aid in the formation of nonaggregating small complexes and for the prevention of nonspecific interactions in vivo. Due to the hydrophilicity of PEG, their lipid conjugates are not permanently associated with lipoplexes and diffuse from the complexes with dilution and interaction with amphiphilic components in vivo. This loss of PEG shielding from the surface of the lipoplexes aids in transfection efficiency. In general, longer saturated fatty acid chains increase circulation while unsaturation and shorter chains decrease circulation.

A commonly invoked tumor targeting mechanism is the Enhanced Permeability and Retention (EPR) effect, which is when nanoparticles accumulate in tumor tissue much more than they do in normal tissues due to the leaky disorganized vasculature associated with tumor tissues and their lack of lymphatic drainage. EPR-based targeting requires long circulating particles.

Polymer Based Delivery Vehicles

Like lipoplexes, polymer-based transfection vehicles (polyplexes) provide nuclease protection and condensation of larger nucleic acids. Polyplexes are based upon cationic polymers that form electrostatic complexes with anionic nucleic acids. Polycations may be purely synthetic (such as polyethyleneimine), naturally occurring (such as histones, protamine, spermine and spermidine) or synthetic polymers based upon cationic amino acids such as ornithine, lysine and arginine.

Polycations form electrostatic complexes with polyanionic nucleic acids. The strength of the association is dependent upon the size of the nucleic acid and the size and charge density of the polycation.

There are three common strategies to improve the stability and surface charge of polyplexes to improve the circulation and targeting of ability of polyplexes: crosslinking of polycation, addition of a synthetic polyanion and conjugation of PEG.

Crosslinking, also called lateral stabilization and caging, is the formation of covalent polyamine-polyamine bonds after complexation/condensation of the nucleic acid. The crosslinking is accomplished by the addition of bifunctional, amine-reactive reagents that form a 3-D network of bonds around the nucleic acid, thereby making the polyplex resistant to displacement by salts and polyelectrolytes. The stability of the polyplexes is such that the nucleic acid is no longer active unless a mechanism of reversibility is introduced to allow for release of the nucleic acid. A common way to introduce reversibility is the use of disulfide-containing crosslinking reagent that can be reduced in the cytoplasm allowing release of nucleic acid therapeutic.

A common method to reduce the surface charge of a polyplex is the conjugation of PEG, a method commonly known as steric stabilization. The resulting PEG modified polyplexes have prolonged circulation in vivo. PEG modifications can be added to the size chains of polyamines—either before or after polyplex formation—or at the end of the polymer as a block copolymer of PEG and polycation.

Crosslinking and PEGylation are often combined to make stabilized polyplexes of reduced surface charge for systemic administration that can either be passively or actively targeted. As observed for lipoplexes, a variety of small molecule (such as GalNAc, RGD and folate) and biologic targeting ligands (such as transferrin and antibodies) have been conjugated to PEG-modified polyplexes for tissues selective targeting.

The most commonly used polymer for polyplexes—and the originator of the proton sponge mechanism—is polyethylenimine (PEI). PEI's high density of amine groups endows it with high charge density and a continuum of amine pKa's that buffer in the entire pH range of the endosome. The buffering capacity of PEI has been mimicked by the addition of weakly basic imidazole groups.

Oligonucleotide vehicle formulation. The solution conditions in which the oligonucleotide is dissolved, or its delivery vehicle is dispersed may play a role in its delivery. Hypotonic and hypertonic solution conditions may aid in cytoplasmic delivery for systemic and locally administration.

Respiratory System Delivery Formulations

In some embodiments, an oligonucleotide disclosed herein is delivered to the respiratory tract via drops. Drops may be advantageous as they are low-cost and relatively straightforward to manufacture. In some cases, the oligonucleotide is administered using a meter-dosed pump sprays. Meter-dosed pump sprays may accurately deliver volumes between 25 and 200 μL. The particle size of the drops from pump sprays is a product of the device, patient handling, as well as the formulation, which varies based on the viscosity and surface tension of the product. Respiratory tract formulations can also be delivered as powders. Powder drug delivery provides a high mass of active ingredients for a given volume.

Once small particle suspensions having therapeutically effective concentrations of 1fTSLP inhibitors have been prepared, solid concentrates can also be prepared by known methods, such as lyophilization, spray-drying and/or supercritical fluid extraction. These solid concentrates can then be resuspended at the time of administration. Also, these solid concentrates may also be compounded to produce a single dosage form such as tablets, capsules, lozenges, suppositories, coated tablets, capsules, ampoules, suppositories, delayed release formulations, controlled release formulations, extended release formulations, pulsatile release formulations, immediate release formulations, gastroretentive formulations, effervescent tablets, fast melt tablets, oral liquid and sprinkle formulations. The solid concentrates may also be formulated in a form selected from the group consisting of a patch, a powder preparation for inhalation, a suspension, an ointment and an emulsion.

Small particle compositions 1fTSLP inhibitors can also be formulated in therapeutically effective concentrations for delivery as an aerosol for respiratory delivery to the lungs or as a suspension.

Small particles of can be made using any appropriate method including, but not limited to, precipitation methods, mechanical/physical particle size reduction methods such as milling and homogenization, phospholipids coating methods, surfactant coating methods, spray-drying methods, supercritical fluid methods, and hot melt methods.

To increase the residence time for respiratory tract absorption of drugs after delivery, formulators may add viscosity-increasing and mucoadhesive agents to the formulations. To permit effective dosing of the formulation while maintaining an increased residence time, an in-situ gelling formulation may be used, example of a gel forming agents are gellan and pectin. Another strategy is the use of thixotropic rheological properties that have a low viscosity during actuation. Another method of utilizing mucoadhesive excipients in the formulation intended for respiratory tract delivery is to produce microspheres of drug within the excipient.

Methods and Routes for Administration

The present disclosure includes administration to the respiratory tract of a mammal in a therapeutically effective amount of an oligonucleotide disclosed herein. Respiratory administering or respiratory administration includes administering the composition to the respiratory tract. Pharmaceutical compositions for respiratory administration of a composition may be prepared as sprays, drops, suspensions, gels, ointments, creams or powders.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered drop wise to the subject's eye, or a cream formulation can be administered to a wound site.

The compositions disclosed herein can be administered parenterally such as, for example, by intravenous, intramuscular, intrathecal or subcutaneous injection. Parenteral administration can be accomplished by incorporating the compositions into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120 C, dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, "pulmonary" is also meant to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

The pharmaceutical compositions described herein may be co-administered with one or more additional agents separately or in the same formulation. Such additional agents include, for example, anti-histamines, beta agonists (e.g., albuterol), antibiotics, antiinflammatories (e.g. ibuprofen, prednisone (corticosteroid) or pentoxifylline), anti-fungals, (e.g. Amphotericin B, Fluconazole, Ketoconazol, and Itraconazol), steroids, decongestants, bronchodialators, and the like. The formulation may also contain preserving agents, solubilizing agents, chemical buffers, surfactants, emulsifiers, colorants, odorants and sweeteners.

The pharmaceutical composition described herein can be used to treat a patient suffering from a condition mediated by 1fTSLP. In some embodiments, the condition is an inflammatory condition.

Conditions mediated by 1fTSLP activity include, but are not limited to asthma, rheumatoid arthritis, gout, psoriasis, allergic rhinitis, respiratory distress syndrome, chronic obstructive pulmonary disease, acne, atopic dermatitis, atherosclerosis, aortic aneurysm, sickle cell disease, acute lung injury, ischemia/reperfusion injury, nasal polyposis, inflammatory bowel disease (including, for example, ulcerative colitis and Crohn's disease), irritable bowel syndrome, cancer, tumors, respiratory syncytial virus, sepsis, endotoxin shock and myocardial infarction. In some embodiments, the condition mediated by 1fTSLP activity is an inflammatory condition. Inflammatory conditions include, but are not limited to, appendicitis, peptic, gastric or duodenal ulcers, peritonitis, pancreatitis, acute or ischemic colitis, diverticulitis, epiglottitis, achalasia, cholangitis, cholecystitis, hepatitis, inflammatory bowel disease (including, for example, Crohn's disease and ulcerative colitis), enteritis, Whipple's disease, asthma, chronic obstructive pulmonary disease, acute lung injury, ileus (including, for example, post-operative ileus), allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome, or Hodgkins disease.

Respiratory Tract Delivery Devices

For most purposes, a broad distribution of the drug on the mucosal surfaces appears desirable for drugs intended for local action or systemic absorption and for vaccines. In eosinophilic chronic airway diseases, targeted delivery to lung epithelium is desired.

Compositions disclosed herein can be administered into the respiratory system as particles of respirable size, e.g. particles of a size sufficiently small to pass through the nose, mouth and larynx upon inhalation and through the bronchi and alveoli of the lungs. In general, respirable particles range from about 0.5 to 10 microns in size. In some embodiments, the particulate range can be from 1 to 5 microns. In some embodiments, the particulate range can be from 2 to 3 microns. For nasal administration, the particle size may be in the range of 10-500 μm to ensure retention in the nasal cavity.

In some embodiments, an oligonucleotide of the present disclosure is delivered using a respiratory tract delivery device. Liquid respiratory formulations are often aqueous solutions, but suspensions and emulsions can also be delivered. Liquid formulations are considered convenient particularly for topical indications where humidification counteracts the dryness and crusting often accompanying chronic respiratory diseases. In traditional spray pump systems, preservatives are typically required to maintain microbiological stability in liquid formulations.

In some embodiments, an oligonucleotide of the present disclosure is delivered in drops with a pipette. Drops may be administered by sucking liquid into a glass dropper, inserting the dropper into the nostril with an extended neck before squeezing the rubber top to emit the drops.

In some embodiments, an oligonucleotide of the present disclosure is delivered as a liquid with rhinyle catheter and squirt tube. A simple way for a physician or trained assistant to deposit drug in the nose is to insert the tip of a fine catheter or micropipette to the desired area under visual control and squirt the liquid into the desired location.

In some embodiments, an oligonucleotide of the present disclosure is delivered using a squeeze bottle. By squeezing a partly air-filled plastic bottle, the drug is atomized when delivered from a jet outlet. The dose and particle size vary with the force applied.

In some embodiments, an oligonucleotide of the present disclosure is delivered using a metered-dose spray pump. The pump may deliver 100 μl (25-200 μl) per spray, and may offer high reproducibility of the emitted dose and plume geometry in in vitro tests. The particle size and plume geometry can vary within certain limits and depend on the properties of the pump, the formulation, the orifice of the actuator, and the force applied. In some cases, the spray systems is configured to avoid the need for preservatives. These systems use a collapsible bag, a movable piston, or a compressed gas to compensate for the emitted liquid volume. The solutions with a collapsible bag and a movable piston compensating for the emitted liquid volume offer the additional advantage that they can be emitted upside down, without the risk of sucking air into the dip tube and compromising the subsequent spray. This may be useful for some products where the patients are bedridden and where a headdown application is recommended. Some systems have a ball valve at the tip to prevent contamination of the liquid inside the applicator tip. Pumps have been designed with side-actuation. The pump was designed with a shorter tip to avoid contact with the sensitive mucosal surfaces. New designs to reduce the need for priming and re-priming, and pumps incorporating pressure point features to improve the dose reproducibility and dose counters and lock-out mechanisms for enhanced dose control and safety are available. Importantly, the in vivo deposition and clinical performance of metered-dose spray pumps can be enhanced for some applications by adapting the pumps to a novel breath powered "Bi-Directional" delivery technology.

In some embodiments, an oligonucleotide of the present disclosure is delivered via a single- or duo-dose spray device. Metered-dose spray pumps require priming and some degree of overfill to maintain dose conformity for the labeled number of doses. For expensive drugs and vaccines intended for single administration or sporadic use and where tight control of the dose and formulation is of particular importance, single-dose or duo-dose spray devices may be preferred. A simple variant of a single-dose spray device (MAD) is a nosepiece with a spray tip is fitted to a standard syringe. The liquid drug to be delivered is first drawn into the syringe and then the spray tip is fitted onto the syringe.

In some embodiments, an oligonucleotide of the present disclosure is delivered via a respiratory pressurized metered-dose inhaler (pMDI). The particles from a pMDI are released at a high speed with the expansion of a compressed gas. The particles emitted from traditional pMDIs have a particle velocity much higher than a spray pump (5,200 vs. 1,500 cm/s at a distance 1-2 cm from the actuator tip). The issues related to the high particle speed and "cold Freon effect" have been reduced with hydrofluoroalkane (HFA)-based pMDI for respiratory use offering lower particle speeds. Like spray pumps, respiratory pMDIs produce a localized deposition on the anterior non-ciliated epithelium of the respiratory vestibule and in the anterior parts of the narrow respiratory valve, but due to quick evaporation of the spray delivered with a pMDI, noticeable "drip-out" may be less of an issue.

In some embodiments, an oligonucleotide of the present disclosure is delivered via a powered nebulizer or atomizer. Nebulizers use compressed gasses (air, oxygen, and nitrogen) or ultrasonic or mechanical power to break up medical solutions and suspensions into small aerosol droplets that can be directly inhaled into the mouth or nose. The smaller particles and slow speed of the nebulized aerosol are advocated to increase penetration into the respiratory tract.

In some embodiments, an oligonucleotide of the present disclosure is delivered using a powder device. Powder medication formulations can offer advantages, including greater stability than liquid formulations and potential that preservatives may not be required. Powders tend to stick to the moist surface of mucosa before being dissolved and cleared. The use of bioadhesive excipients or agents that slow ciliary action may decrease clearance rates and improve absorption. A number of factors like moisture sensitivity, solubility, particle size, particle shape, and flow characteristics will impact deposition and absorption.

In some cases a powder sprayer has a compressible compartment to provide a pressure that when released creates a plume of powder particles fairly similar to that of a liquid spray. In some cases a breath-actuated inhaler is used where the subject uses his own breath to inhale the powder into the nostril from a blister or capsule.

In some embodiments, an oligonucleotide conjugated with cholesterol or lipid containing >18 carbon atoms administered to lung epithelium increases residence time with tissue and increases intracellular delivery resulting in mRNA reduction.

In some embodiments, an oligonucleotide is administered to respiratory tract in a solution that is hypotonic.

In some embodiments, an agent for decreasing 1fTSLP expression is administered using an aerosol spray device.

In some embodiments, an agent for decreasing 1fTSLP expression is formulated as powder and administered using a using a powder delivery device.

Routes of Delivery

A composition that includes an antisense oligonucleotide or dsRNA agent can be delivered to a subject by a variety of routes. Exemplary routes include: intravenous, subcutaneous, topical, rectal, anal, vaginal, nasal, endotracheally, inhalation, pulmonary, ocular.

The anti sense oligonucleotide or dsRNA agent can be incorporated into pharmaceutical compositions suitable for administration. Such compositions typically include one or more species of anti sense oligonucleotide or dsRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions disclosed herein may be administered in a number of ways depending upon whether local or systemic treatment is desired and upon the area to be treated. Administration may be topical (including ophthalmic, vaginal, rectal, intranasal, inhalation, endotracheal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the antisense oligonucleotide or dsRNA agent in aerosol form.

Exemplary formulations for topical administration include those in which the antisense oligonucleotides or dsRNAs are in admixture with a topical delivery agent such as lipids, liposomes, fatty acids, fatty acid esters, steroids, chelating agents and surfactants. Exemplary lipids and liposomes include neutral (e.g. dioleoyl-phosphatidyl DOPE etlianolaniine, dimyristoylphosphatidyl choline DMPC, distearolyphosphatidyl choline) negative (e.g. dimyristoylphosphatidyl glycerol DMPG) and cationic (e.g. dioleoyltetramemylaminopropyl DOTAP and dioleoyl-phosphatidyl ethanolamine DOTMA).

For topical or other administration, antisense oligonucleotides or dsRNAs may be encapsulated within liposomes or may form complexes thereto, in particular to cationic liposomes. Alternatively, antisense oligonucleotides or dsRNAs may be complexed to lipids, in particular to cationic lipids.

Compositions and formulations for oral administration include powders or granules, microparticulates, nanoparticulates, suspensions or solutions in water or non-aqueous media, capsules, gel capsules, sachets, tablets or rninitablets. Thickeners, flavoring agents, diluents, emulsifiers, dispersing aids or binders may be desirable. Exemplary surfactants include fatty acids and or esters or salts thereof, bile acids and/or salts thereof. In some cases, penetration enhancers, for example, fatty acids salts are combined with bile acids salts. An exemplary combination is the sodium salt of lauric acid, capric acid and UDCA. Further penetration enhancers include polyoxyethylene-9-lauryl ether, polyoxyethylene-20-cetyl ether. Oligonucleotides may be delivered orally, in granular form including sprayed dried particles, or complexed to form micro or nanoparticles.

Compositions and formulations for pulmonary administration may include sterile aqueous solutions that may also contain buffers, diluents and other suitable additives such as, but not limited to, penetration enhancers, carrier compounds and other pharmaceutically acceptable carriers or excipients.

Dosage

In one aspect, provided is a method of administering an antisense oligonucleotide or dsRNA agent to a subject (e.g., a human subject). The method includes administering a unit dose of the antisense oligonucleotide or dsRNA agent that is 14-30 nucleotides (nt) long, for example, 21-23 nt, and is complementary to a target RNA (e.g., 1fTSLP), and optionally includes at least one 3' overhang 1-5 nucleotide long. In some embodiments, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of the antisense oligonucleotide or dsRNA agent (e.g., about 4.4×1016 copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of the antisense oligonucleotide or RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In some embodiments, the unit dose is not administered with a frequency (e.g., not a regular frequency). For example, the unit dose may be administered a single time.

In some embodiments, the effective dose is administered with other traditional therapeutic modalities. For example, a therapeutic agent useful for treating a disease or disorder affecting the lungs.

In some embodiments, a subject is administered an initial dose and one or more maintenance doses of an antisense oligonucleotide or dsRNA agent. The maintenance dose or doses can be the same or lower than the initial dose, e.g., one-half less of the initial dose. A maintenance regimen can include treating the subject with a dose or doses ranging from 0.01 μg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days.

Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed. The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

The anti sense oligonucleotide or dsRNA agents can be administered to mammals, particularly large mammals such as nonhuman primates or humans in a number of ways.

In some embodiments, the administration of the antisense oligonucleotide or dsRNA agent is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, inhalation, pulmonary, intranasal, urethral or ocular. Administration can be provided by the subject or by another person, e.g., a health care provider. The medication can be provided in measured doses or in a dispenser which delivers a metered dose. Selected modes of delivery are discussed elsewhere herein.

Methods

Embodiments also relate to methods for inhibiting the expression of a target gene. The method comprises the step of administering the antisense oligonucleotide or dsRNA agents in any of the preceding embodiments, in an amount sufficient to inhibit expression of the target gene. In some embodiments, the target gene is 1fTSLP. Another aspect relates to a method of modulating the expression of a target gene in a cell, comprising providing to said cell an antisense oligonucleotide or dsRNA agent. In some embodiments, the target gene is sfTSLP. In some embodiments, the antisense oligonucleotide or dsRNA agent described herein is modified.

The present disclosure provides vitro and in vivo methods for treatment of a disease or disorder in a mammal by downregulating or silencing the transcription and/or translation of a target gene of interest. In some embodiments, the method comprises introducing an antisense oligonucleotide or dsRNA agent that silences expression (e.g., mRNA and/or protein levels) of a target sequence into a cell by contacting the cell with a modified antisense oligonucleotide or dsRNA agent described herein. In some embodiments, the method comprises in vivo delivery of an anti sense oligonucleotide or dsRNA agent that silences expression of a target sequence by administering to a mammal a modified antisense oligonucleotide or dsRNA described herein. Administration of the antisense oligonucleotide or dsRNA can be by any route known in the art, such as, e.g., oral, intranasal, inhalation, intravenous, intraperitoneal, intramuscular, intra-articular, intralesional, intratracheal, endotracheal, subcutaneous, or intradermal. In some cases, delivery is by respiratory tract administration. In some embodiments, the target sequence is 1fTSLP. In some embodiments, the target sequence is sfTSLP.

In certain embodiments, the antisense oligonucleotide or dsRNA agent comprises a carrier system, e.g., to deliver the antisense oligonucleotide or dsRNA agent into a cell of a mammal. Non-limiting examples of carrier systems include nucleic acid-lipid particles, liposomes, micelles, virosomes, nucleic acid complexes, and mixtures thereof. In certain instances, the antisense oligonucleotide or dsRNA molecule is complexed with a lipid such as a cationic lipid to form a lipoplex. In certain instances, the antisense oligonucleotide or dsRNA agent is complexed with a polymer such as a cationic polymer (e.g., polyethylenimine (PEI)) to form a polyplex. The anti sense oligonucleotide or dsRNA agent may also be complexed with cyclodextrin or a polymer thereof. In some embodiments, the antisense oligonucleotide or dsRNA agent is encapsulated in a nucleic acid-lipid particle.

In some aspects, disclosed herein is a method of treating an airway disorder in a subject in need thereof, the method comprising administering to the subject a composition comprising an oligonucleotide that targets 1fTSLP. In some embodiments, the airway disorder comprises airway inflammation. In some embodiments, the airway disorder comprises an airway inflammation disorder. In some embodiments, the airway inflammation disorder comprises a Th2 inflammatory disorder. In some embodiments, the airway inflammation disorder comprises asthma. In some embodiments, the airway inflammation disorder comprises nasal polyps. In some embodiments, the airway inflammation disorder comprises allergic rhinitis. In some embodiments, the airway inflammation disorder comprises chronic rhinosinusitis. In some embodiments, the airway inflammation disorder comprises an increased blood eosinophil count. In some embodiments, the administration is by inhalation.

Assessing Up-Regulation or Inhibition of Gene Expression

Transfer of an exogenous nucleic acid into a host cell or organism can be assessed by directly detecting the presence of the nucleic acid in the cell or organism. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis.

For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense or dsRNA modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non-coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides or dsRNA would be assayed by modulation of the reporter gene. Reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Lac), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

1fTSLP protein and mRNA expression can be assayed using methods known to those of skill in the art and described elsewhere herein. For example, immunoassays such as the ELISA can be used to measure protein levels.

In some embodiments, 1fTSLP expression (e.g., mRNA or protein) in a sample (e.g., cells or tissues in vivo or in vitro) treated using an antisense oligonucleotide or dsRNA agent is evaluated by comparison with 1fTSLP expression in a control sample. For example, expression of the protein or nucleic acid can be compared using methods known to those of skill in the art with that in a mock-treated or untreated sample. In some cases, comparison with a sample treated with a control antisense oligonucleotide (e.g., one having an altered or different sequence) can be made depending on the information desired. In some embodiments, a difference in the expression of the 1fTSLP protein or nucleic acid in a treated vs an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of 1fTSLP mRNA or protein, in a sample treated with an antisense oligonucleotide or dsRNA, is increased or decreased by about 1.25-fold to about 10-fold or more relative to an untreated sample or a sample treated with a control nucleic acid. In embodiments, the level of 1fTSLP mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more. In some embodiments, the level of sfTSLP mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Subjects

Some embodiments of the methods described herein include treatment of a subject. Examples of subjects include vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is a dog. In some embodiments, the subject is a cat. In some embodiments, the subject is a cattle. In some embodiments, the subject is a mouse. In some embodiments, the subject is a rat. In some embodiments, the subject is a primate. In some embodiments, the subject is a monkey. In some embodiments, the subject is an animal, a mammal, a dog, a cat, cattle, a rodent, a mouse, a rat, a primate, or a monkey. In some embodiments, the subject is a human.

In some embodiments, the subject is ≥90 years of age. In some embodiments, the subject is ≥85 years of age. In some embodiments, the subject is ≥80 years of age. In some embodiments, the subject is ≥70 years of age. In some embodiments, the subject is ≥60 years of age. In some embodiments, the subject is ≥50 years of age. In some embodiments, the subject is ≥40 years of age. In some embodiments, the subject is ≥30 years of age. In some embodiments, the subject is ≥20 years of age. In some embodiments, the subject is ≥10 years of age. In some embodiments, the subject is ≥1 years of age. In some embodiments, the subject is ≥0 years of age.

In some embodiments, the subject is ≤100 years of age. In some embodiments, the subject is ≤90 years of age. In some embodiments, the subject is ≤85 years of age. In some embodiments, the subject is ≤80 years of age. In some embodiments, the subject is ≤70 years of age. In some embodiments, the subject is ≤60 years of age. In some embodiments, the subject is ≤50 years of age. In some embodiments, the subject is ≤40 years of age. In some embodiments, the subject is ≤30 years of age. In some embodiments, the subject is ≤20 years of age. In some embodiments, the subject is ≤10 years of age. In some embodiments, the subject is ≤1 years of age.

In some embodiments, the subject is between 0 and 100 years of age. In some embodiments, the subject is between 20 and 90 years of age. In some embodiments, the subject is between 30 and 80 years of age. In some embodiments, the subject is between 40 and 75 years of age. In some embodiments, the subject is between 50 and 70 years of age. In some embodiments, the subject is between 40 and 85 years of age.

Baseline

Some embodiments of the methods described herein include obtaining a baseline measurement from a subject. For example, in some embodiments, a baseline measurement is obtained from the subject prior to treating the subject.

In some embodiments, the baseline measurement is a baseline observational measurement. In some embodiments, the baseline observational measurement is obtained using a scoring system. In some embodiments, the baseline observational measurement is obtained using microscopy. In some embodiments, the baseline observational measurement is obtained directly from the subject's skin or airway. In some embodiments, the baseline observational measurement is obtained from an image of the subject's skin or airway. In some embodiments, the baseline observational measurement is a baseline number of nasal polyps. In some embodiments, the baseline observational measurement is a baseline nasal polyp size. In some embodiments, the baseline observational measurement is a baseline mucus measurement. In some embodiments, the baseline observational measurement is a baseline mucus production measurement. In some embodiments, the baseline observational measurement is a baseline airway constriction measurement. In some embodiments, the baseline observational measurement is a baseline inflammation measurement, a baseline swelling measurement, or a baseline redness measurement.

In some embodiments, the baseline measurement is obtained using microscopy, PCR, an immunoassay, a colorimetric assay, or a fluorescence assay.

In some embodiments, the baseline measurement is obtained in a sample obtained from the subject prior to administering the composition to the subject. In some embodiments, the sample is an airway sample. In some embodiments, the sample is a mucus sample. In some embodiments, the sample is an airway tissue sample. In some embodiments, the sample is an airway cell sample. In some embodiments, the sample is a blood sample, a plasma sample, or a serum sample. In some embodiments, the baseline measurement is a baseline blood eosinophil measurement. In some embodiments, the baseline measurement is a baseline MUC5AC measurement.

In some embodiments, the baseline measurement is a baseline inflammatory marker mRNA measurement. In some embodiments, the baseline measurement is a baseline lfTSLP mRNA measurement. In some embodiments, the baseline measurement is a baseline sfTSLP mRNA measurement.

In some embodiments, the baseline measurement is a baseline inflammatory marker protein measurement. In some embodiments, the inflammatory marker comprises IL-4, IL-5, IL-13, or TNFα. In some embodiments, the baseline measurement is a baseline lfTSLP protein measurement. In some embodiments, the baseline measurement is a baseline sfTSLP protein measurement.

Effect

In some embodiments, the composition reduces an observational measurement relative to the baseline observational measurement. In some embodiments, the observational measurement is obtained using a scoring system. In some embodiments, the observational measurement is obtained using microscopy. In some embodiments, the observational measurement is obtained directly from the subject's skin or airway. In some embodiments, the observational measurement is obtained from an image of the subject's skin or airway. In some embodiments, the observational measurement is a number of nasal polyps. In some embodiments, the observational measurement is a nasal polyp size. In some embodiments, the observational measurement is a mucus measurement. In some embodiments, the observational measurement is a mucus production measurement. In some embodiments, the observational measurement is an airway constriction measurement. In some embodiments, the observational measurement is an inflammation measurement, a swelling measurement, or a redness measurement.

In some embodiments, the composition reduces a blood eosinophil measurement relative to the baseline blood eosinophil measurement. In some embodiments, the blood eosinophil measurement is obtained using microscopy, PCR, an immunoassay, a colorimetric assay, or a fluorescence assay. In some embodiments, the blood eosinophil measurement is obtained in a second sample obtained from the subject after administering the composition to the subject.

In some embodiments, the composition reduces a MUC5AC measurement relative to the baseline MUC5AC measurement. In some embodiments, the MUC5AC measurement is obtained using microscopy, PCR, an immunoassay, a colorimetric assay, or a fluorescence assay. In some embodiments, the MUC5AC measurement is obtained in a second sample obtained from the subject after administering the composition to the subject.

In some embodiments, the composition reduces an inflammatory marker mRNA measurement relative to the baseline inflammatory marker mRNA measurement. In some embodiments, the inflammatory marker mRNA measurement is obtained using PCR. In some embodiments, the inflammatory marker mRNA measurement is obtained in a second sample obtained from the subject after administering the composition to the subject.

In some embodiments, the composition reduces a lfTSLP mRNA measurement relative to the baseline lfTSLP mRNA measurement. In some embodiments, the lfTSLP mRNA measurement is obtained using PCR. In some embodiments, the lfTSLP mRNA measurement is obtained in a second sample obtained from the subject after administering the composition to the subject.

In some embodiments, the composition does not affect a sfTSLP mRNA measurement relative to the baseline sfTSLP mRNA measurement. In some embodiments, the sfTSLP mRNA measurement is obtained using PCR. In some embodiments, the sfTSLP mRNA measurement is obtained in a second sample obtained from the subject after administering the composition to the subject.

In some embodiments, the composition reduces an inflammatory marker protein measurement relative to the baseline inflammatory marker protein measurement. In some embodiments, the inflammatory marker protein measurement is obtained using microscopy, an immunoassay, a colorimetric assay, or a fluorescence assay. In some embodiments, the inflammatory marker protein measurement is obtained in a second sample obtained from the subject after administering the composition to the subject. In some embodiments, the inflammatory marker comprises IL-4, IL-5, IL-13, or TNFα.

In some embodiments, the composition reduces a lfTSLP protein measurement relative to the baseline lfTSLP protein measurement. In some embodiments, the lfTSLP protein measurement is obtained using microscopy, an immunoassay, a colorimetric assay, or a fluorescence assay. In some embodiments, the lfTSLP protein measurement is obtained in a second sample obtained from the subject after administering the composition to the subject.

In some embodiments, the composition does not affect a sfTSLP protein measurement relative to the baseline sfTSLP protein measurement. In some embodiments, the sfTSLP protein measurement is obtained using microscopy, an immunoassay, a colorimetric assay, or a fluorescence assay. In some embodiments, the sfTSLP protein measurement is obtained in a second sample obtained from the subject after administering the composition to the subject.

In some embodiments, the second sample is an airway sample. In some embodiments, the second sample is a mucus sample. In some embodiments, the second sample is an airway tissue sample. In some embodiments, the second sample is an airway cell sample. In some embodiments, the second sample is a blood sample, a plasma sample, or a serum sample.

Kits, Research Reagents, Diagnostics, and Therapeutics

The compounds disclosed herein can be utilized for diagnostics, therapeutics, and prophylaxis, and as research reagents and components of kits. Furthermore, antisense oligonucleotides or dsRNA, which inhibit gene expression may be used to elucidate the function of particular genes or to distinguish between functions of various members of a biological pathway.

For use in kits and diagnostics and in various biological systems, the compounds disclosed herein, either alone or in combination with other compounds or therapeutics, may be useful as tools in differential and/or combinatorial analyses to elucidate expression patterns of a portion or the entire complement of genes expressed within cells and tissues.

In some embodiments, the term "biological system" or "system" is any organism, cell, cell culture or tissue that expresses, or is made competent to express products of the long-form thymic stromal lymphopoietin (1fTSLP) genes. These include, but are not limited to, humans, transgenic animals, cells, cell cultures, tissues, xenografts, transplants and combinations thereof.

As one non limiting example, expression patterns within cells or tissues treated with one or more antisense compounds or dsRNAs are compared to control cells or tissues not treated with antisense compounds or dsRNAs and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

In some embodiments, the compounds disclosed herein are useful for research and diagnostics, because these compounds hybridize to nucleic acids encoding long-form thymic stromal lymphopoietin (1fTSLP). For example, oligonucleotides that hybridize with such efficiency and under such conditions as disclosed herein as to be effective 1fTSLP modulators are effective primers or probes under conditions favoring gene amplification or detection, respectively. These primers and probes are useful in methods requiring the specific detection of nucleic acid molecules encoding 1fTSLP and in the amplification of said nucleic acid molecules for detection or for use in further studies of 1fTSLP. Hybridization of the antisense oligonucleotides, particularly the primers and probes, with a nucleic acid encoding 1fTSLP can be detected, e.g., by conjugation of an enzyme to the oligonucleotide, radiolabeling of the oligonucleotide, or any other suitable detection means. Kits using such detection means for detecting the level of 1fTSLP in a sample may also be prepared.

The specificity and sensitivity of antisense and sRNA are also harnessed by those of skill in the art for therapeutic uses. For therapeutics, an animal, e.g., a human, suspected of having a disease or disorder which can be treated by modulating the expression of 1fTSLP polynucleotides is treated by administering oligonucleotide compounds disclosed herein. For example, in one non-limiting embodiment, the methods comprise the step of administering to the animal in need of treatment, a therapeutically effective amount of 1fTSLP modulator. The 1fTSLP modulators disclosed herein effectively modulate the activity of the 1fTSLP or modulate the expression of the 1fTSLP protein. In some embodiments, the activity or expression of 1fTSLP in an animal is inhibited by about 10% as compared to a control. The control may be an oligonucleotide that does not specifically hybridize to 1fTSLP. In some cases, the activity or expression of 1fTSLP in an animal is inhibited by about 30%. In some cases, the activity or expression of 1fTSLP in an animal is inhibited by 50% or more. Thus, the oligomeric compounds may modulate expression of long-form thymic stromal lymphopoietin (1fTSLP) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control. The reduction of the expression of long-form thymic stromal lymphopoietin, (1fTSLP) may be measured in serum, blood, adipose tissue, liver or any other body fluid, tissue or organ of the animal. In some cases, the cells contained within said fluids, tissues or organs being analyzed contain a nucleic acid molecule encoding 1fTSLP peptides and or the 1fTSLP protein itself.

Drug Discovery

The compounds disclosed herein can also be applied in the areas of drug discovery and target validation. The compounds and target segments identified herein may be used in drug discovery efforts to elucidate relationships that exist between long-form thymic stromal lymphopoietin (1fTSLP) polynucleotides and a disease state, phenotype, or condition. These methods include detecting or modulating 1fTSLP polynucleotides comprising contacting a sample, tissue, cell, or organism with the compounds disclosed herein, measuring the nucleic acid or protein level of 1fTSLP polynucleotides and/or a related phenotypic or chemical endpoint at some time after treatment, and optionally comparing the measured value to a non-treated sample or sample treated with a further compound disclosed herein. These methods can also be performed in parallel or in combination with other experiments to determine the function of unknown genes for the process of target validation or to determine the validity of a particular gene product as a target for treatment or prevention of a particular disease, condition, or phenotype.

This disclosure is further illustrated by the following examples, which should not be construed as further limiting. The contents of all references, pending patent applications and published patents, cited throughout this application are hereby expressly incorporated by reference.

Sequence Information

Some embodiments include one or more nucleic acid sequences in the following table:

TABLE 1

Sequences

| SEQ ID NO: | DESCRIPTION |
| --- | --- |
| 1-5184 | lfTSLP siRNA oligonucleotide sequences |
| 5185-9970 | sfTSLP siRNA oligonucleotide sequences |
| 9971-12561 | lfTSLP antisense oligonucleotide sequences |
| 12562-14922 | sfTSLP antisense oligonucleotide sequences |
| 14923 | Full-length lfTSLP human mRNA (GenBank Acc. # NM_033035.5) |
| 14924 | Full-length sfTSLP human mRNA (GenBank Acc. # NM_138551.4) |
| 14925 | Full-length lfTSLP human pre-mRNA (GenBank Acc. # NC_000005.10 nt 111, 071, 692 . . . 111, 078, 024) |
| 14926 | Antisense oligonucleotide targeting lfTSLP |
| 14927 | Antisense oligonucleotide targeting sfTSLP |
| 14928 | non-targeting control antisense oligonucleotide |
| 14929 | Sense strand oligonucleotide targeting lfTSLP |
| 14930 | Antisense strand oligonucleotide targeting lfTSLP |
| 14931 | Sense strand oligonucleotide targeting sfTSLP |
| 14932 | Antisense strand oligonucleotide targeting sfTSLP |
| 14933 | Sense strand non-targeting (control) oligonucleotide |
| 14934 | Antisense strand non-targeting (control) oligonucleotide |
| 14935-17526 | lfTSLP siRNA sense strand sequences |
| 17527-20118 | lfTSLP siRNA sense strand sequences for modifications |
| 20119-22710 | lfTSLP siRNA sense strand sequences for alternative modifications |
| 22711-22906 | sfTSLP siRNA sense strand sequences |
| 22907-23102 | sfTSLP siRNA sense strand sequences for modifications |
| 23103-23298 | sfTSLP siRNA sense strand sequences for alternative modifications |
| 23299-25889 | lfTSLP Antisense oligonucleotide sequences for modifications |
| 25890-25977 | Modified lfTSLP siRNA sense strand sequences |
| 25978-26011 | Modified sfTSLP siRNA sense strand sequences |
| 26012-26099 | Modified lfTSLP siRNA antisense strand sequences |
| 26100-26133 | Modified sfTSLP siRNA antisense strand sequences |
| 26134-28725 | lfTSLP siRNAs antisense strand sequences |
| 28726-28921 | sfTSLP siRNAs antisense strand sequences |
| 28922-31513 | lfTSLP siRNA antisense strand sequences for modifications |
| 31514-34105 | lfTSLP siRNA antisense strand sequences for alternative modifications |
| 34106-34301 | sfTSLP siRNA antisense strand sequences for modifications |
| 34302-34497 | sfTSLP siRNA antisense strand sequences for alternative modifications |
| 34498 | Example RFGF derived from human fibroblast growth factor 4 |
| 34499 | Example RFGF analogue |
| 34500 | Sequence from the HIV Tat protein |
| 34501 | Sequence from the Drosophila Antennapedia protein |
| 34502 | Modification pattern 1S |
| 34503 | Modification pattern 1AS |
| 34504 | Modification pattern 2S |
| 34505 | Modification pattern 3AS |
| 34506 | ASO modification pattern |
| 34507 | Modification pattern 3S |
| 34508 | Modification pattern 4S |
| 34509 | Modification pattern 5S |
| 34510 | Modification pattern 2AS |
| 34511 | Modification pattern 4AS |

Embodiments

Some embodiments include one or more of the following:

1. A composition comprising an oligonucleotide that targets a long isoform of Thymic stromal lymphopoietin (lfTSLP) and when administered to a subject in an effective amount decreases an eosinophil count.

2. The composition of embodiment 1, wherein the eosinophil count is decreased by about 10% or more, as compared to prior to administration.

3. A composition comprising an oligonucleotide that targets lfTSLP and when administered to a subject in an effective amount decreases an inflammatory marker.

4 The composition of embodiment 3, wherein the inflammatory marker is decreased by about 10% or more, as compared to prior to administration.

5. A composition comprising an oligonucleotide that targets lfTSLP and when administered to a subject in an effective amount decreases mucus production.

6. The composition of embodiment 5, wherein the mucus production is decreased by about 10% or more, as compared to prior to administration.

7 The composition of any one of embodiments 1-6, wherein the lfTSLP is encoded by a nucleic acid comprising SEQ ID NO: 14923, or a variant thereof at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical, to SEQ ID NO: 14923.

8. The composition of any one of embodiments 1-7, wherein the 1fTSLP is encoded by a nucleic acid comprising SEQ ID NO: 14923.

9. The composition of any one of embodiments 1-8, wherein the oligonucleotide is specific for 1fTSLP, and/or does not target a short isoform of TSLP (sfTSLP).

10. The composition of any one of embodiments 1-9, wherein the oligonucleotide comprises a modified internucleoside linkage.

11. The composition of embodiment 10, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

12. The composition of embodiment 10, wherein the modified internucleoside linkage comprises one or more phosphorothioate linkages.

13. The composition of any one of embodiments 1-12, wherein the oligonucleotide comprises 1, 2, 3, 4, 5, 6, 7, 8, 9, 10, 11, 12, 13, 14, 15, 16, 17, 18, 19, or 20 modified internucleoside linkages.

14. The composition of any one of embodiments 1-13, wherein the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

15. The composition of any one of embodiments 1-14, wherein the oligonucleotide comprises a modified nucleoside.

16. The composition of embodiment 15, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

17. The composition of embodiment 15, wherein the modified nucleoside comprises a LNA.

18. The composition of embodiment 15, wherein the modified nucleoside comprises a 2',4' constrained ethyl nucleic acid.

19. The composition of embodiment 15, wherein the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

20. The composition of embodiment 15, wherein the modified nucleoside comprises one or more 2'fluoro modified nucleosides.

21. The composition of embodiment 15, wherein the modified nucleoside comprises a 2' O-alkyl modified nucleoside.

22. The composition of embodiment 15, wherein the oligonucleotide comprises a lipid attached at a 3' or 5' terminus of the oligonucleotide.

23. The composition of embodiment 22, wherein the lipid comprises cholesterol, myristoyl, palmitoyl, stearoyl, lithocholoyl, docosanoyl, docosahexaenoyl, myristyl, palmityl stearyl, or α-tocopherol, or a combination thereof.

24. The composition of any one of embodiments 1-23, wherein the oligonucleotide comprises 1, 2, 3, 4, 5, 6, 7, 8, 9, 10, 11, 12, 13, 14, 15, 16, 17, 18, 19, 20, or 21 modified nucleosides.

25. The composition of any one of embodiments 1-24, wherein the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

26. The composition of any one of embodiments 1-25, wherein the oligonucleotide comprises a small interfering RNA (siRNA) comprising a sense strand and an antisense strand.

27. The composition of embodiment 26, wherein the sense strand is 12-30 nucleosides in length.

28. The composition of embodiment 26 or 27, wherein the antisense strand is 12-30 nucleosides in length.

29. A composition comprising an oligonucleotide that targets 1fTSLP, wherein the oligonucleotide comprises a siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14923.

30. A composition comprising an oligonucleotide that targets 1fTSLP, wherein the oligonucleotide comprises an siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14925.

31. The composition of any one of embodiments 26-30, wherein the sense strand and the anti sense strand form a double-stranded RNA duplex.

32. The composition of embodiment 31, wherein the first base pair of the double-stranded RNA duplex is an AU base pair.

33. The composition of any one of embodiments 26-32, wherein the sense strand comprises a 3' overhang comprising 1, 2, or more nucleosides.

34. The composition of embodiment 33, wherein the 3' overhang of the sense strand comprises 2 nucleosides.

35. The composition of any one of embodiments 26-34, wherein the antisense strand comprises a 3' overhang comprising 1, 2, or more nucleosides.

36. The composition of embodiment 34, wherein the 3' overhang of the antisense strand comprises 2 nucleosides.

37. The composition of any one of embodiments 26-36, wherein the sense strand comprises a nucleoside sequence comprising or consisting of the sequence of any one of SEQ ID NOs: 14935-17526, or a nucleic acid sequence thereof having 1 or 2 nucleoside substitutions, additions, or deletions.

38. The composition of any one of embodiments 26-37, wherein the sense strand comprises a nucleoside sequence comprising or consisting of the sequence of any one of SEQ ID NOs: 14935-17526.

39. The composition of any one of embodiments 26-38, wherein the antisense strand comprises a nucleoside sequence comprising or consisting of the sequence of any one of SEQ ID NOs: 26134-28725, or a nucleic acid sequence thereof having 1 or 2 nucleoside substitutions, additions, or deletions.

40. The composition of any one of embodiments 26-39, wherein the antisense strand comprises a nucleoside sequence comprising or consisting of the sequence of any one of SEQ ID NOs: 26134-28725.

41. The composition of any one of embodiments 26-40, wherein the siRNA binds with a 17 mer in a non-human primate 1fTSLP mRNA.

42. The composition of any one of embodiments 26-41, wherein the siRNA binds with a 19 mer in a human 1fTSLP mRNA.

43. The composition of any one of embodiments 26-42, wherein the siRNA binds with a human 1fTSLP mRNA and less than or equal to 20 human off-targets, with no more than 2 mismatches in the antisense strand.

44. The composition of any one of embodiments 26-43, wherein the siRNA binds with a human 1fTSLP mRNA target site that does not harbor an SNP, with a minor allele frequency (MAF) greater or equal to 1% (pos. 2-18).

45. The composition of any one of embodiments 26-44, wherein the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326, or a nucleic acid sequence thereof having 1 or 2 nucleoside substitutions, additions, or deletions; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525, or a nucleic acid sequence thereof having 1 or 2 nucleoside substitutions, additions, or deletions.

46. The composition of any one of embodiments 26-45, wherein the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525.

47. The composition of any one of embodiments 26-46, wherein the sense strand comprises the nucleoside sequence of any one of SEQ ID NOs: 14942, 14947, 14948, 14950, 14957, 14959, 15004, 15035, 15039, 15040, 15041, 15043, 15047, 15048, 15049, 15050, 15051, 15057, 15059, 15082, 15094, 15096, 15097, 15098, 15102, 15107, 15108, 15111, 15114, 15123, 15127, 15128, 15164, 15184, 15186, 15187, 15188, 15190, 15191, 15194, 15195, 15230, 15235, 15236, 15238, 15241, 15246, 15252, 15260, 15263, 15272, 15276, 15278, 15279, 15283, 15294, 15302, 15307, 15314, 15322, 15324, or 15326; and/or wherein the antisense strand comprises the nucleoside sequence of any one of SEQ ID NOs: 26141, 26146, 26147, 26149, 26156, 26158, 26203, 26234, 26238, 26239, 26240, 26242, 26246, 26247, 26248, 26249, 26250, 26256, 26258, 26281, 26293, 26295, 26296, 26297, 26301, 26306, 26307, 26310, 26313, 26322, 26326, 26327, 26363, 26383, 26385, 26386, 26387, 26389, 26390, 26393, 26394, 26429, 26434, 26435, 26437, 26440, 26445, 26451, 26459, 26462, 26471, 26475, 26477, 26478, 26482, 26493, 26501, 26506, 26513, 26521, 26523, or 26525.

48. The composition of any one of embodiments 26-47, wherein the sense strand comprises the nucleoside sequence of any one of SEQ ID NOs: 15041, 15048, 15051, 15082, 15096, 15111, 15114, 15123, 15128, 15187, 15194, 15230, 15235, 15238, 15241, 15252, 15272, 15278, 15307, or 15326; and/or wherein the antisense strand comprises the nucleoside sequence of any one of SEQ ID NOs: 26240, 26247, 26250, 26281, 26295, 26310, 26313, 26322, 26327, 26386, 26393, 26429, 26434, 26437, 26440, 26451, 26471, 26477, 26506, or 26525.

49. The composition of any one of embodiments 26-48, wherein the sense strand comprises the nucleoside sequence of any one of SEQ ID NOs: 15048, 15051, 15082, 15096, 15111, 15114, 15123, 15128, 15194, 15230, 15235, 15238, 15241, 15252, 15272, 15278, 15307, or 15326; and/or wherein the antisense strand comprises the nucleoside sequence of any one of SEQ ID NOs: 26247, 26250, 26281, 26295, 26310, 26313, 26322, 26327, 26393, 26429, 26434, 26437, 26440, 26451, 26471, 26477, 26506, or 26525.

50. The composition of any one of embodiments 26-49, wherein the sense strand comprises the nucleoside sequence of any one of SEQ ID NOs: 17527-20118, or a nucleic acid sequence thereof having 1 or 2 nucleoside substitutions, additions, or deletions.

51. The composition of any one of embodiments 26-50, wherein the sense strand comprises the nucleoside sequence of any one of SEQ ID NOs: 17527-20118.

52. The composition of any one of embodiments 26-51 wherein the sense strand comprises the nucleoside sequence of any one of SEQ ID NOs: 20119-22710, or a nucleic acid sequence thereof having 1 or 2 nucleoside substitutions, additions, or deletions.

53. The composition of any one of embodiments 26-52, wherein the sense strand comprises the nucleoside sequence of any one of SEQ ID NOs: 20119-22710.

54. The composition of any one of embodiments 26-53, wherein the antisense strand comprises the nucleoside sequence of any one of SEQ ID NOs: 28922-31513, or a nucleic acid sequence thereof having 1 or 2 nucleoside substitutions, additions, or deletions.

55. The composition of any one of embodiments 26-54, wherein the antisense strand comprises the nucleoside sequence of any one of SEQ ID NOs: 28922-31513.

56. The composition of any one of embodiments 26-55, wherein the antisense strand comprises the nucleoside sequence of any one of SEQ ID NOs: 31514-34105, or a nucleic acid sequence thereof having 1 or 2 nucleoside substitutions, additions, or deletions.

57. The composition of any one of embodiments 26-56, wherein the antisense strand comprises the nucleoside sequence of any one of SEQ ID NOs: 31514-34105.

58. The composition of any one of embodiments 26-57, wherein the sense strand comprises modification pattern 1S: 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage.

59. The composition of any one of embodiments 26-57, wherein the sense strand comprises modification pattern 2S: 5'-nsnsnnNfnNfNfNfnnnnnnnnnnnsnsn-3' (SEQ ID NO: 34504), wherein "Nf" is a 2' fluoro-modified nucleoside, "n" is a 2' O-methyl modified nucleoside, and "s" is a phosphorothioate linkage.

60. The composition of any one of embodiments 26-57, wherein the sense strand comprises modification pattern 3S: 5'-nsnsnnNfnNfnNfnnnnnnnnnnnsnsn-3' (SEQ ID NO: 34507), wherein "Nf" is a 2' fluoro-modified nucleoside, "n" is a 2' O-methyl modified nucleoside, and "s" is a phosphorothioate linkage.

61. The composition of any one of embodiments 26-57, wherein the sense strand comprises modification pattern 4S: 5'-NfsnsNfriNfnNfnNfNfNfnNfnNfnNthNfnNfsnsnN-Lipid-3' (SEQ ID NO: 34508), wherein "Nf" is a 2' fluoro-modified nucleoside, "n" is a 2' O-methyl modified nucleoside, "s" is a phosphorothioate linkage, and N comprises one or more nucleosides.

62. The composition of any one of embodiments 26-57, wherein the sense strand comprises modification pattern 5S: 5'-nsnsnnNfnNfNfNfnnnnnnnnnnnsnsnN-Lipid-3' (SEQ ID NO: 34509), wherein "Nf" is a 2' fluoro-modified nucleoside, "n" is a 2' O-methyl modified nucleoside, "s" is a phosphorothioate linkage, and N comprises one or more nucleosides.

63. The composition of any one of embodiments 26-62, wherein the antisense strand comprises modification pattern 1AS: 5'-nsNfsnNfnNfnNfnNfnNfnnnNfnNfnNfsnsn-3' (SEQ ID NO: 34503), wherein "Nf" is a 2' fluoro-modified nucleoside, "n" is a 2' O-methyl modified nucleoside, and "s" is a phosphorothioate linkage.

64. The composition of any one of embodiments 26-62, wherein the antisense strand comprises modification pattern 2AS: 5'-nsNfsnnnNfnNfNfnnnnNfnNfnnnsnsn-3' (SEQ ID NO: 34510), wherein "Nf" is a 2' fluoro-modified nucleoside, "n" is a 2' O-methyl modified nucleoside, and "s" is a phosphorothioate linkage.

65. The composition of any one of embodiments 26-62, wherein the antisense strand comprises modification pattern 3AS: 5'-nsNfsnnnNfnnnnnnnNfnNfnnnsnsn-3' (SEQ ID NO: 34505), wherein "Nf" is a 2' fluoro-modified nucleoside, "n" is a 2' O-methyl modified nucleoside, and "s" is a phosphorothioate linkage.

66. The composition of any one of embodiments 26-62, wherein the antisense strand comprises modification pattern 4AS: 5'-nsNfsnNfnNfnnnnnnnNfnNfnnnsnsn-3' (SEQ ID NO: 34511), wherein "Nf" is a 2' fluoro-modified nucleoside, "n" is a 2' O-methyl modified nucleoside, and "s" is a phosphorothioate linkage.

67. The composition of any one of embodiments 26-57, wherein the sense strand comprises pattern 1s and the antisense strand comprises pattern 1AS, 2AS, 3AS, or 4AS.

68. The composition of any one of embodiments 26-57, wherein the sense strand comprises pattern 2S and the antisense strand comprises pattern 1AS, 2AS, 3AS, or 4AS.

69. The composition of any one of embodiments 26-57, wherein the sense strand comprises pattern 3S and the antisense strand comprises pattern 1AS, 2AS, 3AS, or 4AS.

70. The composition of any one of embodiments 26-57, wherein the sense strand comprises pattern 4S and the antisense strand comprises pattern 1AS, 2AS, 3AS, or 4AS.

71. The composition of any one of embodiments 26-57, wherein the sense strand comprises the nucleoside sequence of any one of SEQ ID NOs: 17533, 17534, 17539, 17540, 17542, 17549, 17551, 17552, 17553, 17554, 17565, 17596, 17597, 17605, 17627, 17631, 17632, 17633, 17635, 17639, 17640, 17641, 17642, 17643, 17644, 17648, 17649, 17651, 17654, 17674, 17686, 17688, 17689, 17690, 17693, 17694, 17699, 17700, 17703, 17706, 17709, 17715, 17719, 17720, 17756, 17766, 17770, 17776, 17778, 17779, 17780, 17782, 17783, 17786, 17787, 17789, 17822, 17827, 17828, 17830, 17832, 17833, 17838, 17844, 17845, 17852, 17855, 17856, 17864, 17866, 17868, 17870, 17871, 17874, 17875, 17878, 17886, 17894, 17895, 17899, 17902, 17906, 17911, 17912, 17913, 17914, 17916, or 17918; and/or wherein the antisense strand comprises the nucleoside sequence of any one of SEQ ID NOs: 28928, 28929, 28934, 28935, 28937, 28944, 28946, 28947, 28948, 28949, 28960, 28991, 28992, 29000, 29022, 29026, 29027, 29028, 29030, 29034, 29035, 29036, 29037, 29038, 29039, 29043, 29044, 29046, 29049, 29069, 29081, 29083, 29084, 29085, 29088, 29089, 29094, 29095, 29098, 29101, 29104, 29110, 29114, 29115, 29151, 29161, 29165, 29171, 29173, 29174, 29175, 29177, 29178, 29181, 29182, 29184, 29217, 29222, 29223, 29225, 29227, 29228, 29233, 29239, 29240, 29247, 29250, 29251, 29259, 29261, 29263, 29265, 29266, 29269, 29270, 29273, 29281, 29289, 29290, 29294, 29297, 29301, 29306, 29307, 29308, 29309, 29311, or 29313.

72. The composition of any one of embodiments 26-57, wherein the sense strand comprises the nucleoside sequence of any one of SEQ ID NOs: 17534, 17539, 17540, 17542, 17549, 17551, 17596, 17627, 17631, 17632, 17633, 17635, 17639, 17640, 17641, 17642, 17643, 17649, 17651, 17674, 17686, 17688, 17689, 17690, 17694, 17699, 17700, 17703, 17706, 17715, 17719, 17720, 17756, 17776, 17778, 17779, 17780, 17782, 17783, 17786, 17787, 17822, 17827, 17828, 17830, 17833, 17838, 17844, 17852, 17855, 17864, 17868, 17870, 17871, 17875, 17886, 17894, 17899, 17906, 17914, 17916, or 17918; and/or wherein the antisense strand comprises the nucleoside sequence of any one of SEQ ID NOs: 28929, 28934, 28935, 28937, 28944, 28946, 28991, 29022, 29026, 29027, 29028, 29030, 29034, 29035, 29036, 29037, 29038, 29044, 29046, 29069, 29081, 29083, 29084, 29085, 29089, 29094, 29095, 29098, 29101, 29110, 29114, 29115, 29151, 29171, 29173, 29174, 29175, 29177, 29178, 29181, 29182, 29217, 29222, 29223, 29225, 29228, 29233, 29239, 29247, 29250, 29259, 29263, 29265, 29266, 29270, 29281, 29289, 29294, 29301, 29309, 29311, or 29313.

73. The composition of any one of embodiments 26-57, wherein the sense strand comprises the nucleoside sequence of any one of SEQ ID NOs: 17633, 17640, 17643, 17674, 17688, 17703, 17706, 17715, 17720, 17779, 17786, 17822, 17827, 17830, 17833, 17844, 17864, 17870, 17899, or 17918; and/or wherein the antisense strand comprises the nucleoside sequence of any one of SEQ ID NOs: 29028, 29035, 29038, 29069, 29083, 29098, 29101, 29110, 29115, 29174, 29181, 29217, 29222, 29225, 29228, 29239, 29259, 29265, 29294, or 29313.

74. The composition of any one of embodiments 26-57, wherein the sense strand comprises the nucleoside sequence of any one of SEQ ID NOs: 17640, 17643, 17674, 17688, 17703, 17706, 17715, 17720, 17786, 17822, 17827, 17830, 17833, 17844, 17864, 17870, 17899, or 17918; and/or wherein the antisense strand comprises the nucleoside sequence of any one of SEQ ID NOs: 29035, 29038, 29069, 29083, 29098, 29101, 29110, 29115, 29181, 29217, 29222, 29225, 29228, 29239, 29259, 29265, 29294, or 29313.

75. The composition of any one of embodiments 1-25, wherein the oligonucleotide comprises an antisense oligonucleotide (ASO).

76. The composition of embodiment 75, wherein the ASO is single-stranded and 12-30 nucleosides in length.

77. A composition comprising an oligonucleotide that targets 1fTSLP, wherein the oligonucleotide comprises an ASO comprising an antisense strand about 12-30 nucleosides in length and comprising a nucleoside sequence comprising about 12-30 contiguous nucleosides of one of SEQ ID NO: 14923.

78. A composition comprising an oligonucleotide that targets TSLP, wherein the oligonucleotide comprises an ASO comprising an antisense strand about 12-30 nucleosides in length and comprising a nucleoside sequence comprising about 12-30 contiguous nucleosides of one of SEQ ID NO: 14925.

79. The composition of any one of embodiments 75-78, wherein the ASO is 15-25 nucleosides in length.

80. The composition of any one of embodiments 75-79, wherein the ASO is 20 nucleosides in length.

81. The composition of any one of embodiments 75-80, wherein the ASO comprises a nucleoside sequence comprising or consisting of the sequence of any one of SEQ ID NOs: 9971-12561, or a nucleic acid sequence thereof having 1 or 2 nucleoside substitutions, additions, or deletions.

82. The composition of any one of embodiments 75-81, wherein the ASO comprises a nucleoside sequence comprising or consisting of the sequence of any one of SEQ ID NOs: 9971-12561.

83. The composition of any one of embodiments 75-82, wherein the ASO comprises a nucleoside sequence comprising or consisting of the sequence of any one of SEQ ID NOs: 23299-25889, or a nucleic acid sequence thereof having 1 or 2 nucleoside substitutions, additions, or deletions.

84. The composition of any one of embodiments 75-83, wherein the ASO comprises a nucleoside sequence comprising or consisting of the sequence of any one of SEQ ID NOs: 23299-25889.

85. The composition of any one of embodiments 75-84, wherein the ASO comprises modification pattern: 5'-nsnsnsnsnsdNsdNsdNsdNsdNsdNsdNsdNsnsnsnsnsn-3' (SEQ ID NO: 34506) where "dN" is any deoxynucleotide, "n" is a 2'O-methyl or 2'O-methoxyethyl-modified nucleoside, and "s" is a phosphorothioate linkage.

86. The composition of any one of embodiments 1-85, wherein the composition is a pharmaceutical composition.

87. The composition of any one of embodiments 1-86, wherein the composition is sterile.

88. The composition of any one of embodiments 1-87, further comprising a pharmaceutically acceptable carrier.

89. The composition of embodiment 88, wherein the pharmaceutically acceptable carrier comprises water, a buffer, or a saline solution.

90. The composition of any one of embodiments 1-89, formulated for administration by inhalation.

91. A method of treating an airway inflammation disorder in a subject in need thereof, the method comprising administering to the subject a composition comprising an oligonucleotide that targets 1fTSLP.

92. The method of embodiment 91, wherein the airway inflammation disorder comprises asthma.

93. The method of embodiment 91, wherein the airway inflammation disorder comprises nasal polyps.

94. The method of embodiment 91, wherein the airway inflammation disorder comprises allergic rhinitis.

95. The method of embodiment 91, wherein the airway inflammation disorder comprises chronic rhinosinusitis.

96. The method of any one of embodiments 91-95, wherein the airway inflammation disorder comprises an increased blood eosinophil count.

97. The method of any one of embodiments 91-96, wherein the administration is by inhalation.

98. The method of any one of embodiments 91-97, wherein the subject is an animal, a mammal, a dog, a cat, cattle, a rodent, a mouse, a rat, a primate, or a monkey.

99. The method of any one of embodiments 91-98, wherein the subject is a human.

100. The method of any one of embodiments 91-99, wherein the subject is ≥40 years of age.

101. The method of any one of embodiments 91-100, wherein the subject is ≤85 years of age.

102. The method of any one of embodiments 91-101, wherein the subject is ≥40 and ≤85 years of age.

103. The method of any one of embodiments 91-102, wherein a baseline measurement is obtained from the subject prior to administering the composition to the subject.

104. The method of embodiment 103, wherein the baseline measurement is a baseline observational measurement.

105. The method of embodiment 104, wherein the baseline observational measurement is obtained using a scoring system.

106. The method of embodiment 104 or 105, wherein the baseline observational measurement is obtained using microscopy.

107. The method of any one of embodiments 104-106, wherein the baseline observational measurement is obtained directly from the subject's skin or airway.

108. The method of any one of embodiments 104-106, wherein the baseline observational measurement is obtained from an image of the subject's skin or airway.

109. The method of any one of embodiments 104-108, wherein the baseline observational measurement is a baseline number of nasal polyps.

110. The method of any one of embodiments 104-108, wherein the baseline observational measurement is a baseline nasal polyp size.

111. The method of any one of embodiments 104-108, wherein the baseline observational measurement is a baseline mucus measurement.

112. The method of any one of embodiments 104-108, wherein the baseline observational measurement is a baseline mucus production measurement.

113. The method of any one of embodiments 104-108, wherein the baseline observational measurement is a baseline airway constriction measurement.

114. The method of any one of embodiments 104-108, wherein the baseline observational measurement is a baseline inflammation measurement, a baseline swelling measurement, or a baseline redness measurement.

115. The method of embodiment 103, wherein the baseline measurement is obtained in a sample obtained from the subject prior to administering the composition to the subject.

116. The method of embodiment 115, wherein the sample is an airway sample.

117. The method of embodiment 115 or 116, wherein the sample is a mucus sample.

118. The method of embodiment 115, wherein the sample is an airway tissue sample 119. The method of embodiment 115, wherein the sample is an airway cell sample 120. The method of embodiment 115, wherein the sample is a blood sample, a plasma sample, or a serum sample.

121. The method of any one of embodiments 115-120, wherein the baseline measurement is obtained using microscopy, PCR, an immunoassay, a colorimetric assay, or a fluorescence assay.

122. The method of any one of embodiments 115-121, wherein the baseline measurement is a baseline blood eosinophil measurement.

123. The method of any one of embodiments 115-121, wherein the baseline measurement is a baseline MUC5AC measurement.

124. The method of any one of embodiments 115-121, wherein the baseline measurement is a baseline inflammatory marker mRNA measurement.

125. The method of any one of embodiments 115-121, wherein the baseline measurement is a baseline inflammatory marker protein measurement.

126. The method of embodiment 124 or 125, wherein the inflammatory marker comprises IL-4, IL-5, IL-13, or TNFα.

127. The method of any one of embodiments 115-121, wherein the baseline measurement is a baseline 1fTSLP mRNA measurement.

128. The method of any one of embodiments 115-121, wherein the baseline measurement is a baseline 1fTSLP protein measurement.

129. The method of any one of embodiments 115-121, wherein the baseline measurement is a baseline sfTSLP mRNA measurement.

130. The method of any one of embodiments 115-121, wherein the baseline measurement is a baseline sfTSLP protein measurement.

131. The method of any of embodiments 104-114, wherein the composition reduces an observational measurement relative to the baseline observational measurement.

132. The method of embodiment 131, wherein the observational measurement is obtained using a scoring system.

133. The method of embodiment 131 or 132, wherein the observational measurement is obtained using microscopy.

134. The method of any one of embodiments 131-133, wherein the observational measurement is obtained directly from the subject's skin or airway.

135. The method of any one of embodiments 131-133, wherein the observational measurement is obtained from an image of the subject's skin or airway.

136. The method of any one of embodiments 131-133, wherein the observational measurement is a number of nasal polyps.

137. The method of any one of embodiments 131-133, wherein the observational measurement is a nasal polyp size.

138. The method of any one of embodiments 131-133, wherein the observational measurement is a mucus measurement.

139. The method of any one of embodiments 131-133, wherein the observational measurement is a mucus production measurement.

140. The method of any one of embodiments 131-133, wherein the observational measurement is an airway constriction measurement.

141. The method of any one of embodiments 131-133, wherein the observational measurement is an inflammation measurement, a swelling measurement, or a redness measurement.

142. The method of embodiment 122, wherein the composition reduces a blood eosinophil measurement relative to the baseline blood eosinophil measurement.

143. The method of embodiment 142, wherein the blood eosinophil measurement is obtained using microscopy, PCR, an immunoassay, a colorimetric assay, or a fluorescence assay.

144. The method of embodiment 123, wherein the composition reduces a MUC5AC measurement relative to the baseline MUC5AC measurement.

145. The method of embodiment 144, wherein the MUC5AC measurement is obtained using microscopy, PCR, an immunoassay, a colorimetric assay, or a fluorescence assay.

146. The method of embodiment 124, wherein the composition reduces an inflammatory marker mRNA measurement relative to the baseline inflammatory marker mRNA measurement.

147. The method of embodiment 146, wherein the inflammatory marker mRNA measurement is obtained using PCR.

148. The method of embodiment 125, wherein the composition reduces an inflammatory marker protein measurement relative to the baseline inflammatory marker protein measurement.

149. The method of embodiment 148, wherein the inflammatory marker protein measurement is obtained using microscopy, an immunoassay, a colorimetric assay, or a fluorescence assay.

150. The method of any one of embodiments 146-149, wherein the inflammatory marker comprises IL-4, IL-5, IL-13, or TNFα.

151. The method of embodiment 127, wherein the composition reduces a 1fTSLP mRNA measurement relative to the baseline 1fTSLP mRNA measurement.

152. The method of embodiment 151, wherein the 1fTSLP mRNA measurement is obtained using PCR.

153. The method of embodiment 128, wherein the composition reduces a 1fTSLP protein measurement relative to the baseline 1fTSLP protein measurement.

154. The method of embodiment 153, wherein the 1fTSLP protein measurement is obtained using microscopy, an immunoassay, a colorimetric assay, or a fluorescence assay.

155. The method of embodiment 129, wherein the composition does not affect a sfTSLP mRNA measurement relative to the baseline sfTSLP mRNA measurement.

156. The method of embodiment 155, wherein the sfTSLP mRNA measurement is obtained using PCR.

157. The method of embodiment 130, wherein the composition does not affect a sfTSLP protein measurement relative to the baseline sfTSLP protein measurement.

158. The method of embodiment 157, wherein the sfTSLP protein measurement is obtained using microscopy, an immunoassay, a colorimetric assay, or a fluorescence assay.

159. The method of embodiment 142 or 143, wherein the blood eosinophil measurement is obtained in a second sample obtained from the subject after administering the composition to the subject.

160. The method of embodiment 144 or 145, wherein the MUC5AC measurement is obtained in a second sample obtained from the subject after administering the composition to the subject.

161. The method of any one of embodiments 146, 147, or 150, wherein the inflammatory marker mRNA measurement is obtained in a second sample obtained from the subject after administering the composition to the subject.

162. The method of any one of embodiments 148-150, wherein the inflammatory marker protein measurement is obtained in a second sample obtained from the subject after administering the composition to the subject.

163. The method of embodiment 151 or 152, wherein the lfTSLP mRNA measurement is obtained in a second sample obtained from the subject after administering the composition to the subject.

164. The method of embodiment 153 or 154, wherein the lfTSLP protein measurement is obtained in a second sample obtained from the subject after administering the composition to the subject.

165. The method of embodiment 155 or 156, wherein the sfTSLP mRNA measurement is obtained in a second sample obtained from the subject after administering the composition to the subject.

166. The method of embodiment 157 or 158, wherein the sfTSLP protein measurement is obtained in a second sample obtained from the subject after administering the composition to the subject.

167. The method of any one of embodiments 159-166, wherein the second sample is an airway sample.

168. The method of any one of embodiments 159-167, wherein the second sample is a mucus sample.

169. The method of any one of embodiments 159-168, wherein the second sample is an airway tissue sample.

170. The method of any one of embodiments 159-169, wherein the second sample is an airway cell sample.

171. The method of any one of embodiments 159-170, wherein the second sample is a blood sample, a plasma sample, or a serum sample.

172. The method of any one of embodiments 91-171, wherein the lfTSLP is encoded by a nucleic acid comprising SEQ ID NO: 14923, or a variant thereof at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical, to SEQ ID NO: 14923.

173. The method of any one of embodiments 91-172, wherein the lfTSLP is encoded by a nucleic acid comprising SEQ ID NO: 14923.

174. The method of any one of embodiments 91-173, wherein the oligonucleotide is specific for lfT'SLP, and/or does not target a short isoform of TSLP (sfT'SLP).

175. The method of any one of embodiments 91-174, wherein the oligonucleotide comprises a modified internucleoside linkage.

176. The method of embodiment 175, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

177. The method of embodiment 175, wherein the modified internucleoside linkage comprises one or more phosphorothioate linkages.

178. The method of any one of embodiments 91-177, wherein the oligonucleotide comprises 1, 2, 3, 4, 5, 6, 7, 8, 9, 10, 11, 12, 13, 14, 15, 16, 17, 18, 19, or 20 modified internucleoside linkages.

179. The method of any one of embodiments 91-178, wherein the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

180. The method of any one of embodiments 91-179, wherein the oligonucleotide comprises a modified nucleoside.

181. The method of embodiment 180, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

182. The method of embodiment 180, wherein the modified nucleoside comprises a LNA.

183. The method of embodiment 180, wherein the modified nucleoside comprises a 2',4' constrained ethyl nucleic acid.

184. The method of embodiment 180, wherein the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

185. The method of embodiment 180, wherein the modified nucleoside comprises one or more 2'fluoro modified nucleosides.

186. The method of embodiment 180, wherein the modified nucleoside comprises a 2' 0-alkyl modified nucleoside.

187. The method of embodiment 180, wherein the oligonucleotide comprises a lipid attached at a 3' or 5' terminus of the oligonucleotide.

188. The method of embodiment 187, wherein the lipid comprises cholesterol, myristoyl, palmitoyl, stearoyl, lithocholoyl, docosanoyl, docosahexaenoyl, myristyl, palmityl stearyl, or α-tocopherol, or a combination thereof.

189. The method of any one of embodiments 91-188, wherein the oligonucleotide comprises 1, 2, 3, 4, 5, 6, 7, 8, 9, 10, 11, 12, 13, 14, 15, 16, 17, 18, 19, 20, or 21 modified nucleosides.

190. The method of any one of embodiments 91-189, wherein the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

191. The method of any one of embodiments 91-190, wherein the oligonucleotide comprises a small interfering RNA (siRNA) comprising a sense strand and an antisense strand.

192. The method of embodiment 191, wherein the sense strand is 12-30 nucleosides in length.

193. The method of embodiment 191 or 192, wherein the antisense strand is 12-30 nucleosides in length.

194. A composition comprising an oligonucleotide that targets 1fTSLP, wherein the oligonucleotide comprises a siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14923.

195. A composition comprising an oligonucleotide that targets 1fTSLP, wherein the oligonucleotide comprises an siRNA comprising a sense strand and an antisense strand, each strand is independently about 12-30 nucleosides in length, and at least one of the sense strand and the antisense strand comprises a nucleoside sequence comprising about 12-30 contiguous nucleosides of one of SEQ ID NO: 14925.

196. The method of any one of embodiments 191-195, wherein the sense strand and the anti sense strand form a double-stranded RNA duplex.

197. The method of embodiment 196, wherein the first base pair of the double-stranded RNA duplex is an AU base pair.

198. The method of any one of embodiments 191-197, wherein the sense strand comprises a 3' overhang comprising 1, 2, or more nucleosides.

199. The method of embodiment 198, wherein the 3' overhang of the sense strand comprises 2 nucleosides.

200. The method of any one of embodiments 191-199, wherein the antisense strand comprises a 3' overhang comprising 1, 2, or more nucleosides.

201. The method of embodiment 200, wherein the 3' overhang of the antisense strand comprises 2 nucleosides.

202. The method of any one of embodiments 191-201, wherein the sense strand comprises a nucleoside sequence comprising or consisting of the sequence of any one of SEQ ID NOs: 14935-17526, or a nucleic acid sequence thereof having 1 or 2 nucleoside substitutions, additions, or deletions.

203. The method of any one of embodiments 191-202, wherein the sense strand comprises a nucleoside sequence comprising or consisting of the sequence of any one of SEQ ID NOs: 14935-17526.

204. The method of any one of embodiments 191-203, wherein the antisense strand comprises a nucleoside sequence comprising or consisting of the sequence of any one of SEQ ID NOs: 26134-28725, or a nucleic acid sequence thereof having 1 or 2 nucleoside substitutions, additions, or deletions.

205. The method of any one of embodiments 191-204, wherein the antisense strand comprises a nucleoside sequence comprising or consisting of the sequence of any one of SEQ ID NOs: 26134-28725.

206. The method of any one of embodiments 191-205, wherein the siRNA binds with a 17 mer in a non-human primate 1fTSLP mRNA.

207. The method of any one of embodiments 191-206, wherein the siRNA binds with a 19 mer in a human 1fTSLP mRNA.

208. The method of any one of embodiments 191-206, wherein the siRNA binds with a human 1fTSLP mRNA and less than or equal to 20 human off-targets, with no more than 2 mismatches in the antisense strand.

209. The method of any one of embodiments 191-208, wherein the siRNA binds with a human 1fTSLP mRNA target site that does not harbor an SNP, with a minor allele frequency (MAF) greater or equal to 1% (pos. 2-18).

210. The method of any one of embodiments 191-209, wherein the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326, or a nucleic acid sequence thereof having 1 or 2 nucleoside substitutions, additions, or deletions; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525, or a nucleic acid sequence thereof having 1 or 2 nucleoside substitutions, additions, or deletions.

211. The method of any one of embodiments 191-210, wherein the sense strand comprises the nucleoside sequence of any one of SEQ ID NOs: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, or 15326; and/or wherein the antisense strand comprises the nucleoside sequence of any one of SEQ ID NOs: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, or 26525.

212. The method of any one of embodiments 191-211, wherein the sense strand comprises the nucleoside sequence of any one of SEQ ID NOs: 14942, 14947, 14948, 14950, 14957, 14959, 15004, 15035, 15039, 15040, 15041, 15043, 15047, 15048, 15049, 15050, 15051, 15057, 15059, 15082, 15094, 15096, 15097, 15098, 15102, 15107, 15108, 15111, 15114, 15123, 15127, 15128, 15164, 15184, 15186, 15187, 15188, 15190, 15191, 15194, 15195, 15230, 15235, 15236, 15238, 15241, 15246, 15252, 15260, 15263, 15272, 15276, 15278, 15279, 15283, 15294, 15302, 15307, 15314, 15322, 15324, or 15326; and/or wherein the antisense strand comprises the nucleoside sequence of any one of SEQ ID NOs: 26141, 26146, 26147, 26149, 26156, 26158, 26203, 26234, 26238, 26239, 26240, 26242, 26246, 26247, 26248, 26249, 26250, 26256, 26258, 26281, 26293, 26295, 26296, 26297, 26301, 26306, 26307, 26310, 26313, 26322, 26326, 26327, 26363, 26383, 26385, 26386, 26387, 26389, 26390, 26393, 26394, 26429, 26434, 26435, 26437, 26440, 26445, 26451, 26459, 26462, 26471, 26475, 26477, 26478, 26482, 26493, 26501, 26506, 26513, 26521, 26523, or 26525.

213. The method of any one of embodiments 191-212, wherein the sense strand comprises the nucleoside sequence of any one of SEQ ID NOs: 15041, 15048, 15051, 15082, 15096, 15111, 15114, 15123, 15128, 15187, 15194, 15230, 15235, 15238, 15241, 15252, 15272, 15278, 15307, or 15326; and/or wherein the antisense strand comprises the nucleoside sequence of any one of SEQ ID NOs: 26240, 26247, 26250, 26281, 26295, 26310, 26313, 26322, 26327, 26386, 26393, 26429, 26434, 26437, 26440, 26451, 26471, 26477, 26506, or 26525.

214. The method of any one of embodiments 191-213, wherein the sense strand comprises the nucleoside sequence of any one of SEQ ID NOs: 15048, 15051, 15082, 15096, 15111, 15114, 15123, 15128, 15194, 15230, 15235, 15238, 15241, 15252, 15272, 15278, 15307, or 15326; and/or wherein the antisense strand comprises the nucleoside sequence of any one of SEQ ID NOs: 26247, 26250, 26281, 26295, 26310, 26313, 26322, 26327, 26393, 26429, 26434, 26437, 26440, 26451, 26471, 26477, 26506, or 26525.

215. The method of any one of embodiments 191-214, wherein the sense strand comprises the nucleoside sequence of any one of SEQ ID NOs: 17527-20118, or a nucleic acid sequence thereof having 1 or 2 nucleoside substitutions, additions, or deletions.

216. The method of any one of embodiments 191-215, wherein the sense strand comprises the nucleoside sequence of any one of SEQ ID NOs: 17527-20118.

217. The method of any one of embodiments 191-216 wherein the sense strand comprises the nucleoside sequence of any one of SEQ ID NOs: 20119-22710, or a nucleic acid sequence thereof having 1 or 2 nucleoside substitutions, additions, or deletions.

218. The method of any one of embodiments 191-217, wherein the sense strand comprises the nucleoside sequence of any one of SEQ ID NOs: 20119-22710.

219. The method of any one of embodiments 191-218, wherein the antisense strand comprises the nucleoside sequence of any one of SEQ ID NOs: 28922-31513, or a nucleic acid sequence thereof having 1 or 2 nucleoside substitutions, additions, or deletions.

220. The method of any one of embodiments 191-219, wherein the antisense strand comprises the nucleoside sequence of any one of SEQ ID NOs: 28922-31513.

221. The method of any one of embodiments 191-220, wherein the antisense strand comprises the nucleoside sequence of any one of SEQ ID NOs: 31514-34105, or a nucleic acid sequence thereof having 1 or 2 nucleoside substitutions, additions, or deletions.

222. The method of any one of embodiments 191-221, wherein the antisense strand comprises the nucleoside sequence of any one of SEQ ID NOs: 31514-34105.

223. The method of any one of embodiments 191-222, wherein the sense strand comprises modification pattern 1S: 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage.

224. The method of any one of embodiments 191-222, wherein the sense strand comprises modification pattern 2S: 5'-nsnsnnNfnNfNfNfnnnnnnnnnnnsnsn-3' (SEQ ID NO: 34504), wherein "Nf" is a 2' fluoro-modified nucleoside, "n" is a 2' O-methyl modified nucleoside, and "s" is a phosphorothioate linkage.

225. The method of any one of embodiments 191-222, wherein the sense strand comprises modification pattern 3S: 5'-nsnsnnNfnNfnNfnnnnnnnnnnnsnsn-3' (SEQ ID NO: 34507), wherein "Nf" is a 2' fluoro-modified nucleoside, "n" is a 2' O-methyl modified nucleoside, and "s" is a phosphorothioate linkage.

226. The method of any one of embodiments 191-222, wherein the sense strand comprises modification pattern 4S: 5'-NfsnsNfnNfnNfNfNffiNfnNfnNthNfnNfsnsnN-Lipid-3' (SEQ ID NO: 34508), wherein "Nf" is a 2' fluoro-modified nucleoside, "n" is a 2' O-methyl modified nucleoside, "s" is a phosphorothioate linkage, and N comprises one or more nucleosides.

227. The method of any one of embodiments 191-222, wherein the sense strand comprises modification pattern 5S: 5'-nsnsnnNfnNfNfNfnnnnnnnnnnnsnsnN-Lipid-3' (SEQ ID NO: 34509), wherein "Nf" is a 2' fluoro-modified nucleoside, "n" is a 2' O-methyl modified nucleoside, "s" is a phosphorothioate linkage, and N comprises one or more nucleosides.

228. The method of any one of embodiments 191-227, wherein the antisense strand comprises modification pattern 1AS: 5'-nsNfsnNfnNfnNfnNfnNfnnnNfnNfnNfnsnsn-3' (SEQ ID NO: 34503), wherein "Nf" is a 2' fluoro-modified nucleoside, "n" is a 2' O-methyl modified nucleoside, and "s" is a phosphorothioate linkage.

229. The method of any one of embodiments 191-227, wherein the antisense strand comprises modification pattern 2AS: 5'-nsNfsnnnNfnNfNfnnnnNfnNfnnnsnsn-3' (SEQ ID NO: 34510), wherein "Nf" is a 2' fluoro-modified nucleoside, "n" is a 2' O-methyl modified nucleoside, and "s" is a phosphorothioate linkage.

230. The method of any one of embodiments 191-227, wherein the antisense strand comprises modification pattern 3AS: 5'-nsNfsnnnNfnnnnnnnNfnNfnnnsnsn-3' (SEQ ID NO: 34505), wherein "Nf" is a 2' fluoro-modified nucleoside, "n" is a 2' O-methyl modified nucleoside, and "s" is a phosphorothioate linkage.

231. The method of any one of embodiments 191-227, wherein the antisense strand comprises modification pattern 4AS: 5'-nsNfsnNfnNfnnnnnnnNfnNfnnnsnsn-3' (SEQ ID NO: 34511), wherein "Nf" is a 2' fluoro-modified nucleoside, "n" is a 2' O-methyl modified nucleoside, and "s" is a phosphorothioate linkage.

232. The method of any one of embodiments 191-222, wherein the sense strand comprises pattern 1S and the antisense strand comprises pattern 1AS, 2AS, 3AS, or 4AS.

233. The method of any one of embodiments 191-222, wherein the sense strand comprises pattern 2S and the antisense strand comprises pattern 1AS, 2AS, 3AS, or 4AS.

234. The method of any one of embodiments 191-222, wherein the sense strand comprises pattern 3S and the antisense strand comprises pattern 1AS, 2AS, 3AS, or 4AS.

235. The method of any one of embodiments 191-222, wherein the sense strand comprises pattern 4S and the antisense strand comprises pattern 1AS, 2AS, 3AS, or 4AS.

236. The method of any one of embodiments 191-222, wherein the sense strand comprises the nucleoside sequence of any one of SEQ ID NOs: 17533, 17534, 17539, 17540, 17542, 17549, 17551, 17552, 17553, 17554, 17565, 17596, 17597, 17605, 17627, 17631, 17632, 17633, 17635, 17639, 17640, 17641, 17642, 17643, 17644, 17648, 17649, 17651, 17654, 17674, 17686, 17688, 17689, 17690, 17693, 17694, 17699, 17700, 17703, 17706, 17709, 17715, 17719, 17720, 17756, 17766, 17770, 17776, 17778, 17779, 17780, 17782, 17783, 17786, 17787, 17789, 17822, 17827, 17828, 17830, 17832, 17833, 17838, 17844, 17845, 17852, 17855, 17856, 17864, 17866, 17868, 17870, 17871, 17874, 17875, 17878, 17886, 17894, 17895, 17899, 17902, 17906, 17911, 17912, 17913, 17914, 17916, or 17918; and/or wherein the antisense strand comprises the nucleoside sequence of any one of SEQ ID NOs: 28928, 28929, 28934, 28935, 28937, 28944, 28946, 28947, 28948, 28949, 28960, 28991, 28992, 29000, 29022, 29026, 29027, 29028, 29030, 29034, 29035, 29036, 29037, 29038, 29039, 29043, 29044, 29046, 29049, 29069, 29081, 29083, 29084, 29085, 29088, 29089, 29094, 29095, 29098, 29101, 29104, 29110, 29114, 29115, 29151, 29161, 29165, 29171, 29173, 29174, 29175, 29177, 29178, 29181, 29182, 29184, 29217, 29222, 29223, 29225, 29227, 29228, 29233, 29239, 29240, 29247, 29250, 29251, 29259, 29261, 29263, 29265, 29266, 29269, 29270, 29273, 29281, 29289, 29290, 29294, 29297, 29301, 29306, 29307, 29308, 29309, 29311, or 29313.

237. The method of any one of embodiments 191-222, wherein the sense strand comprises the nucleoside sequence of any one of SEQ ID NOs: 17534, 17539, 17540, 17542, 17549, 17551, 17596, 17627, 17631, 17632, 17633, 17635, 17639, 17640, 17641, 17642, 17643, 17649, 17651, 17674, 17686, 17688, 17689, 17690, 17694, 17699, 17700, 17703, 17706, 17715, 17719, 17720, 17756, 17776, 17778, 17779, 17780, 17782, 17783, 17786, 17787, 17822, 17827, 17828, 17830, 17833, 17838, 17844, 17852, 17855, 17864, 17868, 17870, 17871, 17875, 17886, 17894, 17899, 17906, 17914, 17916, or 17918; and/or wherein the antisense strand comprises the nucleoside sequence of any one of SEQ ID NOs: 28929, 28934, 28935, 28937, 28944, 28946, 28991, 29022, 29026, 29027, 29028, 29030, 29034, 29035, 29036, 29037, 29038, 29044, 29046, 29069, 29081, 29083, 29084, 29085, 29089, 29094, 29095, 29098, 29101, 29110, 29114, 29115, 29151, 29171, 29173, 29174, 29175, 29177, 29178, 29181, 29182, 29217, 29222, 29223, 29225, 29228, 29233, 29239, 29247, 29250, 29259, 29263, 29265, 29266, 29270, 29281, 29289, 29294, 29301, 29309, 29311, or 29313.

238. The method of any one of embodiments 191-222, wherein the sense strand comprises the nucleoside sequence of any one of SEQ ID NOs: 17633, 17640, 17643, 17674, 17688, 17703, 17706, 17715, 17720, 17779, 17786, 17822, 17827, 17830, 17833, 17844, 17864, 17870, 17899, or 17918; and/or wherein the antisense strand comprises the nucleoside sequence of any one of SEQ ID NOs: 29028, 29035, 29038, 29069, 29083, 29098, 29101, 29110, 29115, 29174, 29181, 29217, 29222, 29225, 29228, 29239, 29259, 29265, 29294, or 29313.

239. The method of any one of embodiments 191-222, wherein the sense strand comprises the nucleoside sequence of any one of SEQ ID NOs: 17640, 17643, 17674, 17688, 17703, 17706, 17715, 17720, 17786, 17822, 17827, 17830, 17833, 17844, 17864, 17870, 17899, or 17918; and/or wherein the antisense strand comprises the nucleoside sequence of any one of SEQ ID NOs: 29035, 29038, 29069, 29083, 29098, 29101, 29110, 29115, 29181, 29217, 29222, 29225, 29228, 29239, 29259, 29265, 29294, or 29313.

240. The method of any one of embodiments 91-190, wherein the oligonucleotide comprises an antisense oligonucleotide (ASO).

241. The method of embodiment 240, wherein the ASO is single-stranded and 12-30 nucleosides in length.

242. A composition comprising an oligonucleotide that targets 1fTSLP, wherein the oligonucleotide comprises an ASO comprising an antisense strand about 12-30 nucleosides in length and comprising a nucleoside sequence comprising about 12-30 contiguous nucleosides of one of SEQ ID NO: 14923.

243. A composition comprising an oligonucleotide that targets TSLP, wherein the oligonucleotide comprises an ASO comprising an antisense strand about 12-30 nucleosides in length and comprising a nucleoside sequence comprising about 12-30 contiguous nucleosides of one of SEQ ID NO: 14925.

244. The method of any one of embodiments 240-243, wherein the ASO is 15-25 nucleosides in length.

245. The method of any one of embodiments 240-244, wherein the ASO is 20 nucleosides in length.

246. The method of any one of embodiments 240-245, wherein the ASO comprises a nucleoside sequence comprising or consisting of the sequence of any one of SEQ ID NOs: 9971-12561, or a nucleic acid sequence thereof having 1 or 2 nucleoside substitutions, additions, or deletions.

247. The method of any one of embodiments 240-246, wherein the ASO comprises a nucleoside sequence comprising or consisting of the sequence of any one of SEQ ID NOs: 9971-12561.

248. The method of any one of embodiments 240-247, wherein the ASO comprises a nucleoside sequence comprising or consisting of the sequence of any one of SEQ ID NOs: 23299-25889, or a nucleic acid sequence thereof having 1 or 2 nucleoside substitutions, additions, or deletions.

249. The method of any one of embodiments 240-248, wherein the ASO comprises a nucleoside sequence comprising or consisting of the sequence of any one of SEQ ID NOs: 23299-25889.

250. The method of any one of embodiments 240-249, wherein the ASO comprises modification pattern: 5'-nsnsnsnsnsdNsdNsdNsdNsdNsdNsdNsdNsnsnsn snsn-3' (SEQ ID NO: 34506) where "dN" is any deoxynucleotide, "n" is a 2'O-methyl or 2'O-methoxyethyl-modified nucleoside, and "s" is a phosphorothioate linkage.

251. The method of any one of embodiments 91-250, wherein the composition is a pharmaceutical composition.

252. The method of any one of embodiments 91-251, wherein the composition is sterile.

253. The method of any one of embodiments 91-252, further comprising a pharmaceutically acceptable carrier.

254. The method of embodiment 253, wherein the pharmaceutically acceptable carrier comprises water, a buffer, or a saline solution.

255. The method of any one of embodiments 91-254, formulated for administration by inhalation.

256. The method of any one of embodiments 91-255, wherein the oligonucleotide targets a sequence within the first 412 nucleotides of SEQ ID NO: 14923.

257. The composition of any one of embodiments 1-90, wherein the oligonucleotide targets a sequence within the first 412 nucleotides of SEQ ID NO: 14923.

258. Use of the composition of any one of embodiments 1-90 or 257, in a method of any one of embodiments 91-256.

Further Embodiments

Some embodiments include one or more of the following:

1. An RNA interference (RNAi) agent capable of inhibiting the expression of long-form thymic stromal lymphopoietin (1fTSLP), wherein the RNAi agent comprises a double-stranded RNA (dsRNA) comprising a sense strand and an antisense strand, each strand having 14 to 30 nucleotides.

2. The RNAi agent of embodiment 1, wherein the dsRNA has a length of 17-30 nucleotide pairs.

3. The RNAi agent of embodiment 1 or embodiment 2, wherein the sense strand and antisense strand each have 17-30 nucleotides.

4. The RNAi agent of any of embodiments 1-3, wherein the sense strand comprises a sequence at least about 80%, 85%, 90%, 95%, or 100% identical to a sequence selected from SEQ ID NOS: 1-5184.

5. The RNAi agent of any of embodiments 1-4, wherein the antisense strand comprises a sequence at least about 80%, 85%, 90%, 95%, or 100% identical to the reverse complement of the sense strand.

6. The RNAi agent of any of embodiments 1-5, wherein the antisense strand comprises a sequence at least about 80%, 85%, 90%, 95%, or 100% identical to a sequence selected from SEQ ID NOS: 1-5184.

7. The RNAi agent of any of embodiments 1-3, wherein the sequence of the sense strand comprises SEQ ID NO: 14929 and the sequence of the antisense strand comprises SEQ ID NO: 14930.

8. The RNAi agent of any of embodiments 1-7, comprising one or more nucleotide modifications selected from the group consisting of LNA, HNA, CeNA, 2'-methoxyethyl, 2'-O-alkyl, 2'-O-allyl, 2'-C-allyl, 2'-fluoro, and 2'-deoxy.

9. The RNAi agent of any of embodiments 1-8, wherein the nucleotides are modified with either 2'-OCH$_3$ or 2'-F.

10. The RNAi agent of any of embodiments 1-9, further comprising at least one ligand.

11. The RNAi agent of any of embodiments 1-10, comprising one or more nucleotide modifications selected from the group consisting of 2'-O-methyl nucleotide, 2'-deoxyfluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, and 2'-ara-F.

12. The RNAi agent of any of embodiments 1-11, further comprising at least one phosphorothioate or methylphosphonate internucleotide linkage.

13. The RNAi agent of any of embodiments 1-12, wherein the nucleotide at the 1 position of the 5'-end of the antisense strand of the dsRNA is selected from the group consisting of A, dA, dU, U, and dT.

14. The RNAi agent of any of embodiments 1-13, wherein the base pair at the 1 position of the 5'-end of the dsRNA is an AU base pair.

15. An RNA interference (RNAi) agent capable of inhibiting the expression of 1fTSLP, wherein the RNAi agent comprises a double-stranded RNA (dsRNA) comprising a sense strand and an antisense strand, each of the strands having 14 to 30 nucleotides, wherein the sense strand contains at least two motifs of three identical modifications on three consecutive nucleotides, a first of said sense strand motifs occurring at a cleavage site in the sense strand and a second of said sense strand motifs occurring at a different region of the sense strand that is separated from the first sense strand motif by at least one nucleotide; and wherein the antisense strand contains at least two motifs of three identical modifications on three consecutive nucleotides, a first of said antisense strand motifs occurring at or near the cleavage site in the antisense strand and a second of said antisense strand motifs occurring at a different region of the anti sense strand that is separated from the first antisense strand motif by at least one nucleotide; wherein the modification in the first antisense strand motif is different than the modification in the second antisense strand motif.

16. The RNAi agent of embodiment 15, wherein at least one of the nucleotides occurring in the first sense strand motif forms a base pair with one of the nucleotides in the first antisense strand motif.

17. The RNAi agent of embodiment 15 or embodiment 16, wherein the dsRNA has 17-30 nucleotide base pairs.

18. The RNAi agent of embodiment 17, wherein the dsRNA has 17-19 nucleotide base pairs.

19. The RNAi agent of any of embodiments 15-18, wherein each strand has 17-23 nucleotides.

20. The RNAi agent of any of embodiments 15-19, wherein the modifications on the nucleotides of the sense strand and/or antisense strand are selected from the group consisting of LNA, HNA, CeNA, 2'-methoxyethyl, 2'-O-alkyl, 2'-O-allyl, 2'-C— allyl, 2'-fluoro, 2'-deoxy, and combinations thereof.

21. The RNAi agent of any of embodiments 15-20, wherein the modifications on the nucleotides of the sense strand and/or antisense strand are 2'-OCH$_3$ or 2'-F.

22. The RNAi agent of any of embodiments 15-21, further comprising a ligand attached to the 3' end of the sense strand.

23. An RNA interference (RNAi) agent capable of inhibiting the expression of 1fTSLP, wherein the RNAi agent comprises a double-stranded RNA (dsRNA) comprising a sense strand and an antisense strand, each of the strands having 14 to 30 nucleotides, wherein the sense strand contains at least one motif of three 2'-F modifications on three consecutive nucleotides, one of said motifs occurring at or near the cleavage site in the sense strand; and wherein the antisense strand contains at least one motif of three 2'-O-methyl modifications on three consecutive nucleotides, one of said motifs occurring at or near the cleavage site in the antisense strand.

24. The RNAi agent of embodiment 23, wherein the sense strand comprises a sequence at least about 80%, 85%, 90%, 95%, or 100% identical to a sequence selected from SEQ ID NOS: 1-5184.

25. The RNAi agent of embodiment 23 or embodiment 24, wherein the antisense strand comprises a sequence at least about 80%, 85%, 90%, 95%, or 100% identical to the reverse complement of the sense strand.

26. The RNAi agent of any of embodiments 23-25, wherein the antisense strand comprises a sequence at least about 80%, 85%, 90%, 95%, or 100% identical to a sequence selected from SEQ ID NOS: 1-5184.

27. A method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least 50% sequence identity to a reverse complement of a polynucleotide comprising 5 to 30 consecutive nucleotides within nucleotides 1 to 2610 of SEQ ID NO: 14923; thereby modulating a function of and/or the expression of the long-form thymic stromal lymphopoietin (1fTSLP) polynucleotide in patient cells or tissues, in vivo or in vitro.

28. A method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide 5 to 30 nucleotides in length, wherein said antisense oligonucleotide has at least 50% sequence identity to an antisense oligonucleotide to the long-form thymic stromal lymphopoietin (1fTSLP) polynucleotide; thereby modulating a function of and/or the expression of the long-form thymic stromal lymphopoietin (1fTSLP) polynucleotide in patient cells or tissues, in vivo or in vitro.

29. A method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide that targets a region of a natural antisense oligonucleotide of the long-form thymic stromal lymphopoietin (1fTSLP) polynucleotide; thereby modulating a function of and/or the expression of the long-form thymic stromal lymphopoietin (1fTSLP) polynucleotide in patient cells or tissues, in vivo or in vitro.

30. A method of modulating a function of and/or the expression of a long-form thymic stromal lymphopoietin (1fTSLP) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least about 80%, 85%, 90%, 95%, or 100% sequence identity to a sequence selected from SEQ ID NOS: 9971-12561; thereby modulating a function of and/or the expression of the 1fTSLP polynucleotide in patient cells or tissues, in vivo or in vitro.

31. The method of any one of embodiments 27-29, wherein the at least one antisense oligonucleotide comprises SEQ ID NO: 14926.

32. The method of any one of embodiments 27-29, wherein the at least one antisense oligonucleotide comprises a sequence selected from SEQ ID NOS: 9971-12561.

33. The method of any one of embodiments 27-29, wherein the at least one antisense oligonucleotide comprises a sequence at least about 80%, 85%, 90%, 95%, or 100% identical to a sequence selected from SEQ ID NOS: 9971-12561.

34. The method of any of embodiments 27-33, wherein a function of and/or the expression of the long-form thymic stromal lymphopoietin (1fTSLP) is increased in vivo or in vitro with respect to a control oligonucleotide that does not target or specifically hybridize to 1fTSLP.

35. The method of any of embodiments 27-33, wherein a function of and/or the expression of the long-form thymic stromal lymphopoietin (1fTSLP) is decreased in vivo or in vitro with respect to a control oligonucleotide that does not target or specifically hybridize to 1fTSLP.

36. The method of any of embodiments 27-35, wherein the at least one antisense oligonucleotide targets a natural antisense sequence of a long-form thymic stromal lymphopoietin (1fTSLP) polynucleotide.

37. The method of any of embodiments 27-35, wherein the at least one antisense oligonucleotide targets a natural sense sequence of a long-form thymic stromal lymphopoietin (1fTSLP) polynucleotide.

38. The method of any of embodiments 27-37, wherein the at least one antisense oligonucleotide targets a nucleic acid sequence comprising coding and/or non-coding nucleic acid sequences of a long-form thymic stromal lymphopoietin (1fTSLP) polynucleotide.

39. The method of any of embodiments 27-38, wherein the at least one antisense oligonucleotide targets overlapping and/or non-overlapping sequences of a long-form thymic stromal lymphopoietin (1fTSLP) polynucleotide.

40. The method of any of embodiments 27-39, wherein the at least one antisense oligonucleotide comprises one or more modifications.

41. The method of embodiment 40, wherein the one or more modifications is selected from: at least one modified sugar moiety, at least one modified internucleoside linkage, at least one modified nucleotide, and combinations thereof.

42. The method of embodiment 40, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

43. The method of embodiment 40, wherein the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof.

44. The method of embodiment 40, wherein the one or more modifications comprise at least one modified nucleotide selected from: a peptide nucleic acid (PNA), a locked nucleic acid (LNA), an arabino-nucleic acid (FANA), an analogue, a derivative, and combinations thereof.

45. A method of modulating a function of and/or the expression of a long-form thymic stromal lymphopoietin (1fTSLP) gene in mammalian cells or tissues, in vivo or in vitro, the method comprising: contacting said cells or tissues with at least one short interfering RNA (siRNA) oligonucleotide 5 to 30 nucleotides in length, said at least one siRNA oligonucleotide being specific for an antisense polynucleotide of a long-form thymic stromal lymphopoietin (1fTSLP) polynucleotide, wherein said at least one siRNA oligonucleotide has at least 50% sequence identity to a complementary sequence of at least about five consecutive nucleic acids of the antisense and/or sense nucleic acid molecule of the long-form thymic stromal lymphopoietin (1fTSLP) polynucleotide; thereby modulating a function of and or the expression of long-form thymic stromal lymphopoietin, (1fTSLP) in mammalian cells or tissues in vivo or in vitro.

46. The method of embodiment 45, wherein said oligonucleotide has at least 80% sequence identity to a sequence of at least about five consecutive nucleic acids that is complementary to the antisense and/or sense nucleic acid molecule of the long-form thymic stromal lymphopoietin (1fTSLP) polynucleotide.

47. The method of embodiment 45 or embodiment 46, wherein the at least one siRNA oligonucleotide comprises a sequence selected from SEQ ID NOS: 1-5184.

48. The method of embodiment 45 or embodiment 46, wherein the at least one siRNA oligonucleotide comprises a sequence at least about 80%, 85%, 90%, 95%, or 100% identical to a sequence selected from SEQ ID NOS: 1-5184.

49. A method of modulating a function of and/or the expression of long-form thymic stromal lymphopoietin, (1fTSLP) in mammalian cells or tissues, in vivo or in vitro, the method comprising: contacting said cells or tissues with at least one antisense oligonucleotide of about 5 to 30 nucleotides in length, the antisense oligonucleotide specific for noncoding and/or coding sequences of a sense and/or natural antisense strand of a long-form thymic stromal lymphopoietin (1fTSLP) polynucleotide, wherein said at least one antisense oligonucleotide has at least 50% sequence identity to at least one nucleic acid sequence set forth as 1 to 2610 of SEQ ID NO: 14923 or its complement; thereby modulating the function and/or expression of the long-form thymic stromal lymphopoietin (1fTSLP) in mammalian cells or tissues, in vivo or in vitro.

50. The method of embodiment 49, wherein the at least one antisense oligonucleotide comprises a sequence selected from SEQ ID NOS: 9971-12561.

51. The method of embodiment 49, wherein the at least one antisense oligonucleotide comprises a sequence at least about 80%, 85%, 90%, 95%, or 100% identical to a sequence selected from SEQ ID NOS: 9971-12561.

52. A synthetic, modified oligonucleotide comprising at least one modification wherein the at least one modification is selected from: at least one modified sugar moiety; at least one modified intenucleotide linkage; at least one modified nucleotide, and combinations thereof; wherein said oligonucleotide is an antisense compound which hybridizes to and modulates the function and/or expression of a long-form thymic stromal lymphopoietin (1fTSLP) polynucleotide in vivo or in vitro as compared to a control oligonucleotide that does not specifically hybridize to the 1fTSLP polynucleotide.

53. The oligonucleotide of embodiment 52, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

54. The oligonucleotide of embodiment 53, wherein said oligonucleotide comprises at least one phosphorothioate internucleotide linkage.

55. The oligonucleotide of embodiment 53, wherein said oligonucleotide comprises a backbone of phosphorothioate internucleotide linkages.

56. The oligonucleotide of embodiment 53, wherein the oligonucleotide comprises at least one modified nucleotide, said modified nucleotide selected from: a peptide nucleic acid, a locked nucleic acid (LNA), and an analogue, derivative, and a combination thereof.

57. The oligonucleotide of embodiment 52, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

58. The oligonucleotide of embodiment 52, wherein the oligonucleotide comprises a plurality of modifications, wherein said modifications comprise modified nucleotides selected from: peptide nucleic acids, locked nucleic acids (LNA), and analogues, derivatives, and a combination thereof.

59. The oligonucleotide of embodiment 52, wherein the oligonucleotide comprises at least one modified sugar moiety selected from: a 2'-O-methoxyethyl modified sugar moiety, a 2'-methoxy modified sugar moiety, a 2-O-alkyl modified sugar moiety, a bicyclic sugar moiety, and a combination thereof.

60. The oligonucleotide of embodiment 52, wherein the oligonucleotide comprises a plurality of modifications, wherein said modifications comprise modified sugar moieties selected from: a 2'-O-methoxyethyl modified sugar moiety, a 2-methoxy modified sugar moiety, a 2'-O-alkyl modified sugar moiety, a bicyclic sugar moiety, and a combination thereof.

61. The oligonucleotide of embodiment 52, wherein the oligonucleotide is of at least about 5 to 30 nucleotides in length and hybridizes to an antisense and/or sense strand of a long-form thymic stromal lymphopoietin (1fTSLP) polynucleotide, wherein said oligonucleotide has at least about 20% sequence identity to a complementary sequence of at least about five consecutive nucleic acids of the antisense and/or sense coding and/or noncoding nucleic acid sequences of the long-form thymic stromal lymphopoietin (1fTSLP) polynucleotide.

62. The oligonucleotide of embodiment 52, wherein the oligonucleotide has at least about 80% sequence identity to a complementary sequence of at least about five consecutive nucleic acids of the antisense and or sense coding and/or noncoding nucleic acid sequence of the long-form thymic stromal lymphopoietin (1fTSLP) polynucleotide.

63. The oligonucleotide of embodiment 52, wherein said oligonucleotide hybridizes to and modulates expression and/or function of at least one long-form thymic stromal lymphopoietin (1fTSLP) polynucleotide, in vivo or in vitro, as compared to the control oligonucleotide.

64. The oligonucleotide of embodiment 52, wherein the oligonucleotide comprises the sequence set forth as SEQ ID NO: 14926.

65. The oligonucleotide of any one of embodiments 52-64, wherein the at least one antisense oligonucleotide comprises a sequence selected from SEQ ID NOS: 9971-12561.

66. The oligonucleotide of any one of embodiments 52-64, wherein the at least one antisense oligonucleotide comprises a sequence at least about 80%, 85%, 90%, 95%, or 100% identical to a sequence selected from SEQ ID NOS: 9971-12561.

67. A composition comprising one or more oligonucleotides specific for one or more long-form thymic stromal lymphopoietin (1fTSLP) polynucleotides, said one or more oligonucleotides comprising an antisense sequence, complementary sequence, allele, homolog, isoform, variant, derivative, mutant, or fragment of the 1fTSLP polynucleotide, or a combination thereof.

68. The composition of embodiment 67 wherein the one or more oligonucleotides have at least about 40% sequence identity as compared to the nucleotide sequence set forth as SEQ ID NO: 14926.

69. The composition of embodiment 67 or embodiment 68, wherein the oligonucleotide comprises the nucleotide sequence set forth as SEQ ID NO: 14926.

70. The composition of embodiment 67, wherein the one or more oligonucleotides comprises a sequence selected from SEQ ID NOS: 1-14922.

71. The composition of embodiment 67, wherein the one or more oligonucleotides comprises a sequence at least about 80%, 85%, 90%, 95%, or 100% identical to a sequence selected from SEQ ID NOS: 1-14922.

72. The composition of any of embodiments 67-71, wherein the one or more oligonucleotides comprises one or more modifications or substitutions.

73. The composition of embodiment 72, wherein the one or more modifications are selected from: phosphorothioate, methylphosphonate, peptide nucleic acid, locked nucleic acid (LNA) molecules, and combinations thereof.

74. A method of preventing or treating a disease associated with at least one long-form thymic stromal lymphopoietin (1fTSLP) polynucleotide and/or at least one encoded product thereof, the method comprising: administering to a subject in need thereof a therapeutically effective dose of at least one antisense oligonucleotide that binds to a natural antisense sequence of said at least one long-form thymic stromal lymphopoietin (1fTSLP) polynucleotide and modulates expression of said at least one long-form thymic stromal lymphopoietin (1fTSLP) polynucleotide; thereby preventing or treating the disease associated with the at least one long-form thymic stromal lymphopoietin (1fTSLP) polynucleotide and or at least one encoded product thereof.

75. A method of preventing or treating a disease associated with at least one long-form thymic stromal lymphopoietin (1fTSLP) polynucleotide and/or at least one encoded product thereof, the method comprising: administering to a subject in need thereof a therapeutically effective dose of at least one antisense oligonucleotide that binds to a natural sense sequence of said at least one long-form thymic stromal lymphopoietin (1fTSLP) polynucleotide and modulates expression of said at least one long-form thymic stromal lymphopoietin (1fTSLP) polynucleotide; thereby preventing or treating the disease associated with the at least one long-form thymic stromal lymphopoietin (1fTSLP) polynucleotide and or at least one encoded product thereof.

76. The method of embodiment 74 or embodiment 75, wherein a disease associated with the at least one long-form thymic stromal lymphopoietin (1fTSLP) polynucleotide is selected from: a disease or disorder associated with abnormal function and/or expression of 1fTSLP, inflammation of the nasal passageways, inflammation of the lower airway, a proliferative skin disease or disorder, ichthyosis, a disease or disorder associated with impaired epidermal lipid barrier, a disease or disorder associated with impaired adipocyte differentiation, a disease or disorder associated with impaired keratinocyte differentiation, an inflammatory skin disease or disorder, a cardiovascular disease or disorder, a coronary disease or disorder, myocardial infarction, cancer, glandular neoplasm, epithelial neoplasm, ovarian neoplasm, breast neoplasm, stroke and brain ischemia.

77. The method of embodiment 74 or embodiment 75, wherein the proliferative skin disease or disorder comprises psoriasis, chronic proliferative dermatitis, atopic dermatitis, or a combination thereof.

78. The method of embodiment 74 or embodiment 75, wherein the ichthyosis comprises autosomal recessive congenital ichthyosis (ARCI), collodion baby syndrome, non-bullous congenital ichthyosiform eiythroderma, lamellar ichthyosis, or a combination thereof.

79. The method of embodiment 74 or embodiment 75, wherein the cancer is selected from lung cancer, epidermoid carcinoma, breast cancer, or a combination thereof.

80. A method of identifying and selecting at least one oligonucleotide for in vivo administration comprising: identifying at least one oligonucleotide comprising at least five consecutive nucleotides which are complementary to 1fTSLP or to a polynucleotide that is antisense to 1fTSLP; measuring the thermal melting point of a hybrid of an antisense oligonucleotide and the 1fTSLP or the polynucleotide that is antisense to the 1fTSLP under stringent hybridization conditions; and selecting at least one oligonucleotide for in vivo administration based on the information obtained.

81. A method of treating a disease or condition mediated by TSLP, the method comprising administering to a subject in need thereof an oligonucleotide comprising a sequence at least about 80%, 85%, 90%, 95%, or 100% identical to a sequence selected from SEQ ID NOS: 1-14922.

82. The method of embodiment 81, wherein the oligonucleotide comprises a sequence selected from SEQ ID NOS: 1-14922.

83. The method of embodiment 81 or embodiment 82, wherein the TSLP is 1fTSLP. 84. The method of any of embodiments 81-83, wherein the disease or condition comprises allergic rhinitis (AR), non-allergic rhinitis (NAR), chronic rhinosinusitis (CRS), asthma, COPD and asthma-COPD overlap syndrome (ACOS), or a combination thereof.

85. The method of any of embodiments 81-84, wherein the oligonucleotide comprises dsRNA.

86. The method of embodiment 85, wherein the oligonucleotide comprises a sequence at least about 80%, 85%, 90%, 95%, or 100% identical to a sequence selected from SEQ ID NOS: 1-9970.

87. The method of embodiment 86, wherein the oligonucleotide comprises a sequence at least about 80%, 85%, 90%, 95%, or 100% identical to a sequence selected from SEQ ID NOS: 1-5184.

88. The method of any of embodiments 81-84, wherein the oligonucleotide comprises a sequence at least about 80%, 85%, 90%, 95%, or 100% identical to a sequence selected from SEQ ID NOS: 9971-14922.

89. The method of embodiment 88, wherein the oligonucleotide comprises a sequence at least about 80%, 85%, 90%, 95%, or 100% identical to a sequence selected from SEQ ID NOS: 9971-12561.

EXAMPLES

The following non-limiting examples serve to illustrate selected embodiments. It will be appreciated that variations in proportions and alternatives in elements of the components shown will be apparent to those skilled in the art and are within the scope of embodiments presented herein.

Example 1

Genome-Wide Association Study

Applicants evaluated approximately 30,000,000 imputed and directly genotyped variants in about 350,000 individuals for associations with a range of chronic Th2 or eosinophilic airway diseases and with blood eosinophils counts. One cluster of association was at chromosome 5q22.1, in a region encompassing the thymic stromal lymphopoietin (TSLP) gene.

Figure 2:
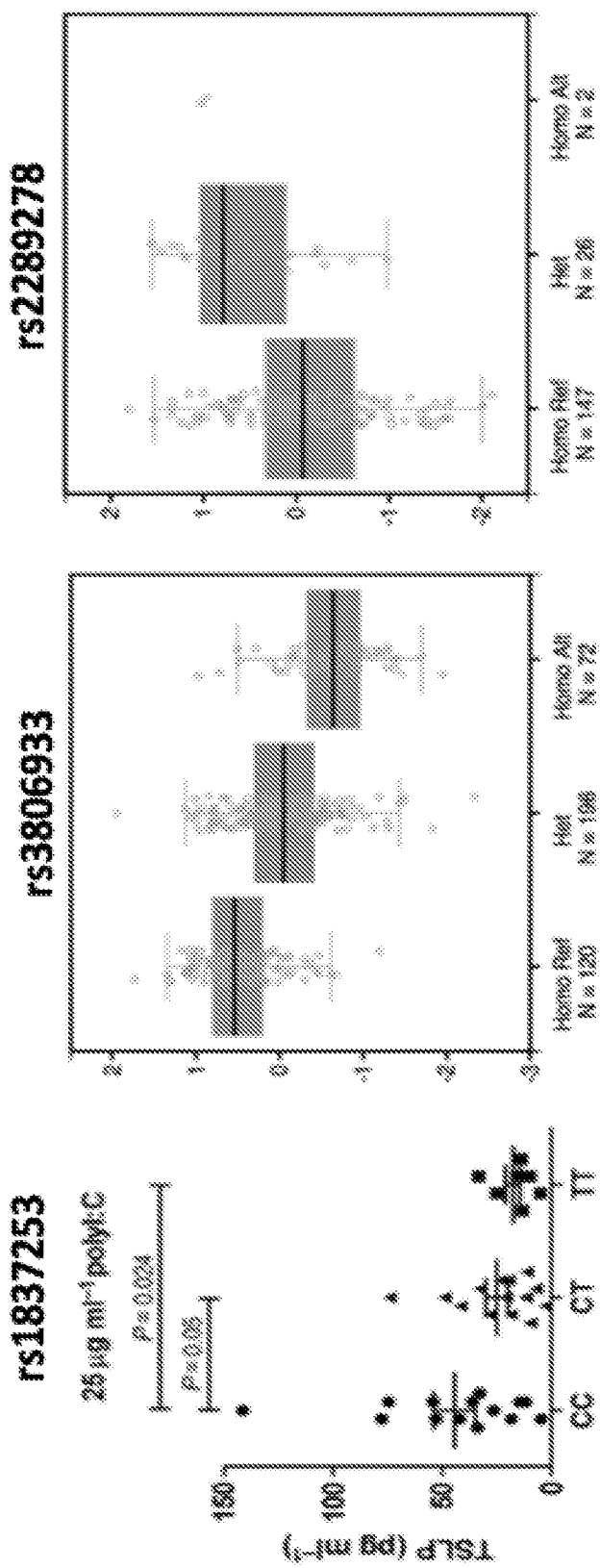
FIG. 2 shows variant rs1837253 (C) is associated with secretion of TSLP from primary nasal epithelial cells, and TSLP variants rs3806933 (C) and rs2289278 (G) are associated with increased expression in most human tissues.
Figure 3:
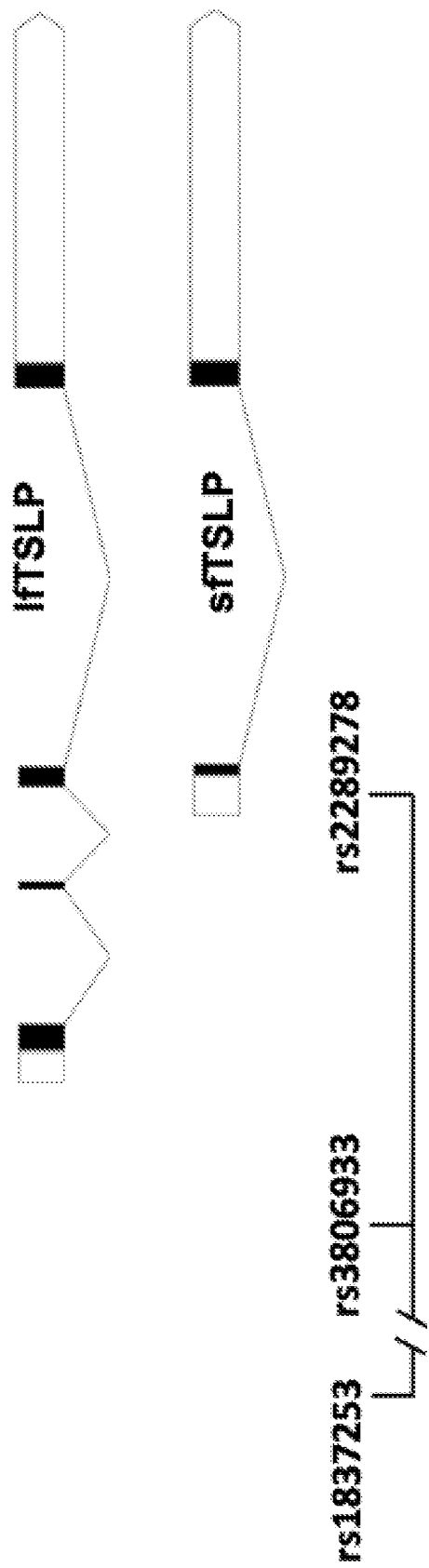
FIG. 3 is a schematic showing the location of variants rs1837253, rs3806933, and rs2289278 with respect to TSLP isoforms.

Applicants identified three independent (r2<0.10) variant clusters at the TSLP gene that are associated with asthma and blood eosinophil levels at genome-wide significance and with nasal polyposis and allergic rhinitis at nominal significance (Table 2). The effect allele of index variant rs1837253 (C) is associated with increased secretion of TSLP from primary nasal epithelial cells (FIG. 2), while the effect alleles of index variants rs3806933 (C) and rs2289278 (G) are associated with increased expression in most human tissues as observed in the Genotype-Tissue Expression (GTEx) project data (FIG. 2). rs1837253 and rs3806933 are located approximately 6 kb and 1 kb upstream of the transcription start site of lfTSLP, respectively, while rs2289278 is located in the 5' UTR and promoter of sfTSLP (FIG. 3).

TABLE 2

| Phenotype | rs1837253 (EAF 0.73) | | rs3806933 (EAF 0.54) | | rs2289278 (EA0.06) | |
| --- | --- | --- | --- | --- | --- | --- |
| | Effect size | P value | Effect size | P value | Effect size | P value |
| Asthma | 1.13 (OR) | 1.13E−42 | 1.06 (OR) | 1.15E−16 | 0.89(OR) | 4.80E−13 |
| Nasal polyps | 1.38 (OR) | 1.47E−31 | 1.10 (OR) | 5.20E−05 | 0.94 (OR) | 1.40E−05 |
| Allergic rhinitis | 1.06 (OR) | 2.80E−07 | 1.08 (OR) | 4.08E−15 | 0.94 (OR) | 2.43R−03 |
| Eosinophil count | 0.005 (beta) | 1.14E−37 | 0.004 (beta) | 3.08E−34 | −0.003 (beta) | 1.11E−04 |

The results in Table 2 demonstrate that the long and short form promoter variants have a different direction of effect in regard to TSLP expression and disease risk. The upstream of long form variants (rs1837253 and rs3806933) are associated with increased TSLP expression and increased disease risk, while the short form promoter variant (rs2289278) is associated with increased TSLP expression and decreased disease risk. A parsimonious explanation for these apparently contradictory results is that the upstream of long form variants (rs1837253 and rs3806933) influence expression of lfTSLP, while the short form promoter variant (rs2289278) influences expression of sfTSLP. This explanation is concordant with the previously described HDM mouse model data, in which increased long form expression is pathogenic while increased short form is protective against allergic airways disease. This novel genetic explanation is supportive of the hypothesis that targeting long form TSLP may be superior to non-specific targeting of TSLP for a broad range of eosinophilic airways disease.

Example 2

RNA Synthesis and Duplex Annealing

1. Oligonucleotide Synthesis:

All oligonucleotides are synthesized on an AKTAoligopilot synthesizer or an ABI 394 synthesizer. Commercially available controlled pore glass solid support (dT-CPG, 500A, Prime Synthesis) and RNA phosphoramidites with standard protecting groups, 5'-O-dimethoxytrityl N6-benzoyl-2'-t-butyldimethylsilyl-adenosine-3'-O—N,N-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutyryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N-diisopropyl-2-cyanoethylphosphoramidite (Pierce Nucleic Acids Technologies) are used for the oligonucleotide synthesis unless otherwise specified. The 2'-F phosphoramidites, 5'-O-dimethoxytrityl-N4-acetyl-2'-fluro-cytidine-3'-O— N,N'-diisopropyl-2-cyanoethyl-phosphoramidite and 5'-O-dimethoxytrityl-2'-fluro-uridine-3'-O—N,N'-diisopropyl-2-cyanoethyl-phosphoramidite are purchased from (Promega). All phosphoramidites are used at a concentration of 0.2M in acetonitrile (CH3CN) except for guanosine which is used at 0.2M concentration in 10% THF/ANC (v/v). Coupling/recycling time of 16 minutes is used. The activator is 5-ethyl thiotetrazole (0.75M, American International Chemicals), for the PO-oxidation Iodine/Water/Pyridine is used and the PS-oxidation PADS (2%>) in 2,6-lutidine/ACN (1:1 v/v) is used.

2. Deprotection-1 (Nucleobase Deprotection)

After completion of synthesis, the support is transferred to a 100 ml glass bottle (VWR). The oligonucleotide is cleaved from the support with simultaneous deprotection of base and phosphate groups with 80 mL of a mixture of ethanolic ammonia [ammonia: ethanol (3:1)] for 6.5 h at 55° C. The bottle is cooled briefly on ice and then the ethanolic ammonia mixture is filtered into a new 250 ml bottle. The CPG is washed with 2×40 mL portions of ethanol/water (1:1 v/v). The volume of the mixture is then reduced to ~30 ml by roto-vap. The mixture is then frozen on dry ice and dried under vacuum on a speed vac.

3. Deprotection-II (Removal of 2' TBDMS Group)

The dried residue is resuspended in 26 ml of triethylamine, triethylamine trihydro fluoride (TEA.3HF) or pyridine-HF and DMSO (3:4:6) and heated at 60° C. for 90 minutes to remove the tert-butyldimethylsilyl (TBDMS) groups at the 2' position. The reaction is then quenched with 50 ml of 20 mM sodium acetate and pH adjusted to 6.5, and stored in freezer until purification.

4. Analysis

The oligonucleotides are analyzed by high-performance liquid chromatography (HPLC) prior to purification and selection of buffer and column depends on nature of the sequence and or conjugated ligand.

5. HPLC Purification

The ligand conjugated oligonucleotides are purified reverse phase preparative HPLC. The unconjugated oligonucleotides are purified by anion-exchange HPLC on a TSK gel column packed in house. The buffers are 20 mM sodium phosphate (pH 8.5) in 10% CH3CN (buffer A) and 20 mM sodium phosphate (pH 8.5) in 10% CH3CN, 1M NaBr (buffer B). Fractions containing full-length oligonucleotides are pooled, desalted, and lyophilized. Approximately 0.15 OD of desalted oligonucleotides are diluted in water to 150 μl and then pipetted in special vials for CGE and LC/MS analysis.

Compounds are finally analyzed by LC-ESMS and CGE.

6. siRNA Preparation

For the preparation of siRNA, equimolar amounts of sense and antisense strand are heated in 1×PBS at 95° C. for 5 min and slowly cooled to room temperature.

Integrity of the duplex is confirmed by HPLC analysis.

Example 3

Antisense Inhibition of Long and Short-Form TSLP in Primary Normal Human Bronchial Epithelial Cells (NHBEC) and an Immortalized Human Airway Epithelial Cell Line (A549)

In this experiment antisense oligonucleotide inhibition of long and short-form TSLP is performed in primary normal human bronchial epithelial cells (NHBEC) and an immortalized human airway epithelial cell line (A549), to evaluate the percent of knockdown achieved relative to control antisense oligonucleotide.

Adherent NHBECs and A549s actively growing in submerged liquid culture are transfected in a 24-well plate with a scrambled or long-form or short-form targeting antisense oligonucleotide immediately followed by +/− supplementation with poly(I:C) (2.5 µg/mL). The purpose of poly(I:C) supplementation is to induce expression of long and/or short-form TSLP. The long-form targeting antisense oligonucleotide consists of a sequence as follows: 5' mCsmTsmCsmTsmCsdAsdTsdTsdGsdCsdCsd-AsdGsdTsdCsmCsmAsmCsmAsmG 3' (SEQ ID NO: 14926). This antisense oligonucleotide targets nucleotide positions 50-69 of the human TSLP long-form mRNA (GenBank Acc. #NM 033035.5; SEQ ID NO: 14923). The short-form targeting antisense oligonucleotide consists of a sequence as follows: 5' mAsmGsmGsmTsmCsd-AsdGsdGsdGsdTsdTsdGsdAsdGsdTsmAsmGs-mAsmGsmC 3' (SEQ ID NO: 14927). This antisense oligonucleotide targets nucleotide positions 43-62 of the human TSLP short-form mRNA (GenBank Acc. #NM 138551.4; SEQ ID NO: 14924). The non-targeting control antisense oligonucleotide consists of the following sequence: 5' mTsmCsmTsmAsmAsdCsdCsdGsdAsdGsdCsdTsdGsd-AsdTsmGsmGsmAsmCsmT 3' (SEQ ID NO: 14928). The letter "m" before the nucleotide indicates a 2'O-methoxyethyl substitution, the letter "d" indicates a deoxyribonucleotide substitution, and the letter "s" indicates a phosphorothioate linkage. Briefly, transfections are performed using TransIT TKO (Minis) following the manufacturer's recommended protocol. For each well, 1.4 ul antisense oligonucleotide (1 mM stock), 2.5 ul TransIT-TKO, and 50 ul OptiMEM are mixed, incubated at room temperature for 30 minutes, and added dropwise to each well.

At 72 hrs post-transfection, supernatant is collected, cells are trypsinized, and cell lysates prepared using a RIPA buffer. Cell lysates are used to either perform a quantitative PCR (RT-qPCR) or to perform Western blots using a TSLP antibody (Abcam) and a GAPDH antibody (Abcam) as a loading control.

Long-form and short-form TSLP mRNA is quantified using real-time polymerase chain reaction. Total RNA is reverse transcribed to cDNA using a First-Strand III cDNA Synthesis kit (Invitrogen, Carlsbad, Calif.). Then, real-time quantitative polymerase chain reaction (PCR) is performed using the ABI Prism 7900 Sequence Detection System (Applied Biosystems, Foster City, Calif.). Amplification by PCR is performed according to the manufacturer's protocols (Applied Biosystems). Primers and probes for long and short-form TSLP and for β-actin are designed with the assistance of the computer program Primer Express (Applied Biosystems). Searches using a nucleotide basic local alignment search tool (BLASTN) database are conducted to confirm their specificity and the absence of DNA polymorphisms.

Example 4

Comparison of Th2 Inflammatory Response to Isoform Specific Antisense Inhibition of TSLP in NHBECs Differentiated at Air Liquid Interface (ALI)

In this experiment, reverse transfections of antisense oligonucleotide targeting long, short and long+short isoforms of TSLP are performed in NHBECs grown at air liquid interface. Cells are treated with inflammatory stimuli (poly(I:C) or IL13) to compare the effect of long, short, or long+short TSLP inhibition on Th2 cytokine production and mucous production.

Before transfection, precoated inserts are prepared by adding 100 µl of collagen (human placental collagen Type VI, Sigma-Aldrich) to the apical surface of Transwell permeable supports (0.33-cm2 0.4-µm polyester membrane, Costar product no. 3470, Corning, Corning, N.Y.). To prepare for transfection, NHBECs growing on plastic are dissociated with 0.25% trypsin (Life Technologies) and washed with transfection media once.

For each well, 1.4 ul antisense oligonucleotide (1 mM stock), 2.5 ul TransIT-TKO, and 50 ul OptiMEM are mixed, incubated at room temperature for 30 minutes. The long-form targeting antisense oligonucleotide consists of a sequence as follows: 5' mCsmTsmCsmTsmCsd-AsdTsdTsdGsdCsdCsdAsdGsdTsdCsmCsmAsmCsmAsmG 3' (SEQ ID NO: 14926). This antisense oligonucleotide targets nucleotide positions 50-69 of the human TSLP long-form mRNA (GenBank Acc. #NM 033035.5; SEQ ID NO: 14923). The short-form targeting antisense oligonucleotide consists of a sequence as follows: 5' mAsmGsmGsmTsmCsdAsdGsdGsdGsdTsdTsdGsd-AsdGsdTsmAsmGsmAsmGsmC 3' (SEQ ID NO: 14927). This antisense oligonucleotide targets nucleotide positions 43-62 of the human TSLP long-form mRNA (GenBank Acc. #NM 138551.4; SEQ ID NO: 14924). The non-targeting control antisense oligonucleotide consists of the following sequence: 5' mTsmCsmTsmAsmAsdCsdCsdGsd-AsdGsdCsdTsdGsdAsdTsmGsmGsmAsmCsmT 3' (SEQ ID NO: 14928). This transfection mixture is then mixed with 150,000 cells in 150 µl of transfection media and incubated for 4 h at 37° C. in a 5% CO2 incubator. Next, 120 µl of this mixture is added to the apical surface of the insert and incubated for 24 h at 37° C. in a 5% CO2 incubator.

Next, all media are aspirated from the apical surface of the insert and 500 µl of maintenance media is added to the basolateral side of the insert. The apical side of insert is washed three times with fresh media, and finally 20 ul of fresh apical media is added to each insert. Basolateral media is then supplemented with either +/−poly(I:C) (2.5 µg/mL) or +/−IL13 (10 ng/mL). Cells are then maintained for 7 days with 500 ul of basal and 20 ul of apical media, maintaining the indicated concentrations of poly(I:C) and IL13 in the basal media.

Apical supernatant is collected, cells are trypsinized, and cell lysates prepared using a RIPA buffer. The apical supernatant is used to perform a MUC5AC ELISA. Cell lysates are used to perform quantitative PCRs (RT-qPCR) or to perform Western blots using a TSLP antibody (Abcam) and a GAPDH antibody (Abcam) as a loading control.

Long-form and short-form TSLP, IL13, IL4, IL5, and TNF-alpha mRNA is quantified using real-time polymerase chain reaction. Total RNA is reverse transcribed to cDNA using a First-Strand III cDNA Synthesis kit (Invitrogen, Carlsbad, Calif.). Then, real-time quantitative polymerase chain reaction (PCR) is performed using the ABI Prism 7900 Sequence Detection System (Applied Biosystems, Foster City, Calif.). Amplification by PCR is performed according to the manufacturer's protocols (Applied Biosystems). Primers and probes for long and short-form TSLP and for β-actin are designed with the assistance of the computer program Primer Express (Applied Biosystems). Searches using a nucleotide basic local alignment search tool (BLASTN)

database are conducted to confirm their specificity and the absence of DNA polymorphisms.

MUC5AC protein is measured from apical culture supernatants using a semiquantitative sandwich ELISA with two different MUC5AC antibodies, one for coating and one for detection. Briefly, high binding plates are coated with Neomarkers (Fremont, Calif.) MUC5AC antibody (1-13M1) at 1 µg/ml. Neomarker MUC5AC antibody (45M1) labeled with biotin is used at 0.2-0.4 µg/ml for detection. The MUC5AC standard is generated from the apical supernatants of NHBECs under ALI and diluted 1/100 for the high standard followed by serial half dilution. Thus, all results are in relative arbitrary units per ml (AU/ml) and semiquantitative. Samples are studied without dilution or up to 1/4000 dilution depending on sample.

Example 5 siRNA Inhibition of Long and Short-Form TSLP in Primary Normal Human Bronchial Epithelial Cells (NHBEC) and an Immortalized Human Airway Epithelial Cell Line (A549)

In this experiment siRNA inhibition of long and short-form TSLP is performed in primary normal human bronchial epithelial cells (NHBEC) and an immortalized human airway epithelial cell line (A549), to evaluate the percent of knockdown achieved relative to control siRNA.

Adherent NHBECs and A549s actively growing in submerged liquid culture are transfected in a 24-well plate with a scrambled or long-form or short-form targeting siRNA immediately followed by +/−supplementation with poly(I:C) (2.5 µg/mL). The purpose of poly(I:C) supplementation is to induce expression of long and/or short-form TSLP. The long-form TSLP targeting siRNA consists of a double stranded RNA oligonucleotide with sense and antisense sequences as follows: 5'-CUGGUGUUAACUUACGA-CUdTdT-3' (SEQ ID NO: 14929) and 5'-AGU-CGUAAGUUAACACCAGdTdT-3' (SEQ ID NO: 14930). This siRNA targets nucleotide positions 251-279 of the human TSLP transcript variant 1 (NM 033035.5; SEQ ID NO: 14923). The short-form TSLP targeting siRNA consists of a double stranded RNA oligonucleotide with sense and antisense sequences as follows: 5'-CGUAAAC-UUUGCCGCCUAUdTdT-3' (SEQ ID NO: 14931) and 5'-AUAGGCGGCAAAGUUUACGdTdT-3' (SEQ ID NO: 14932). This siRNA targets nucleotide positions 173-191 of the human TSLP transcript variant 2 (NM 138551.4; SEQ ID NO: 14924). The non-targeting (control) siRNA consists of the following sense and antisense sequences: 5'-GUUGUA-CAGCAUGCGGAGAGUdTdT-3' (SEQ ID NO: 14933) and 5'-ACUCUCCGCAUGCUGUACAACdTdT-3' (SEQ ID NO: 14934). The letter d in front of a nucleotide indicates it is a deoxyribonucleotide. Briefly, transfections are performed using TransIT TKO (Mims) following the manufacturer's recommended protocol. For each well, 1.4 ul siRNA (1 mM stock), 2.5 ul TransIT-TKO, and 50 ul OptiMEM are mixed, incubated at room temperature for 30 minutes, and added dropwise to each well.

At 72 hrs post-transfection, supernatant is collected, cells are trypsinized, and cell lysates prepared using a RIPA buffer. Cell lysates are used to either perform a quantitative PCR (RT-qPCR) or to perform Western blots using a TSLP antibody (Abcam) and a GAPDH antibody (Abcam) as a loading control.

Long-form and short-form TSLP mRNA is quantified using real-time polymerase chain reaction. Total RNA is reverse transcribed to cDNA using a First-Strand III cDNA Synthesis kit (Invitrogen, Carlsbad, Calif.). Then, real-time quantitative polymerase chain reaction (PCR) is performed using the ABI Prism 7900 Sequence Detection System (Applied Biosystems, Foster City, Calif.). Amplification by PCR is performed according to the manufacturer's protocols (Applied Biosystems). Primers and probes for long and short-form TSLP and for β-actin are designed with the assistance of the computer program Primer Express (Applied Biosystems). Searches using a nucleotide basic local alignment search tool (BLASTN) database are conducted to confirm their specificity and the absence of DNA polymorphisms.

Example 6

Comparison of Th2 Inflammatory Response to Isoform Specific siRNA Inhibition of TSLP in NHBECs Differentiated at Air Liquid Interface (ALI)

In this experiment, reverse transfections of siRNA targeting long, short and long+short isoforms of TSLP are performed in NHBECs grown at air liquid interface. Cells are treated with inflammatory stimuli (poly(I:C) or IL13) to compare the effect of long, short, or long+short TSLP inhibition on Th2 cytokine production and mucous production.

Before transfection, precoated inserts are prepared by adding 100 µl of collagen (human placental collagen Type VI, Sigma-Aldrich) to the apical surface of Transwell permeable supports (0.33-cm2 0.4-m polyester membrane, Costar product no. 3470, Corning, Corning, N.Y.). To prepare for transfection, NHBECs growing on plastic are dissociated with 0.25% trypsin (Life Technologies) and washed with transfection media once.

For each well, 1.4 ul siRNA (1 mM stock), 2.5 ul TransIT-TKO, and 50 ul OptiMEM are mixed, incubated at room temperature for 30 minutes. The long-form TSLP targeting siRNA consists of a double stranded RNA oligonucleotide with sense and antisense sequences as follows: 5'-CUGGUGUUAACUUACGACUdTdT-3' (SEQ ID NO: 14929) and 5'-AGUCGUAAGUUAACACCAGdTdT-3' (SEQ ID NO: 14930). This siRNA targets nucleotide positions 251-279 of the human TSLP transcript variant 1 (NM 033035.5; SEQ ID NO: 14923). The short-form TSLP targeting siRNA consists of a double stranded RNA oligonucleotide with sense and antisense sequences as follows: 5'-CGUAAACUUUGCCGCCUAUdTdT-3' (SEQ ID NO: 14931) and 5'-AUAGGCGGCAAAGUUUACGdTdT-3' (SEQ ID NO: 14932). This siRNA targets nucleotide positions 173-191 of the human TSLP transcript variant 2 (NM 138551.4; SEQ ID NO: 14924). The scrambled (control) siRNA consists of the following sense and antisense sequences: 5'-GUUGUACAGCAUGCGGAGAGUdTdT-3' (SEQ ID NO: 14933) and 5'-AUAGGCGGCAAAGUUUACGdTdT-3' (SEQ ID NO: 14934). The letter d in front of a nucleotide indicates it is a deoxyribonucleotide. This transfection mixture is then mixed with 150,000 cells in 150 µl of transfection media and incubated for 4 h at 37° C. in a 5% CO2 incubator. Next, 120 µl of this mixture is added to the apical surface of the insert, and incubated for 24 h at 37° C. in a 5% CO2 incubator.

Next, all media are aspirated from the apical surface of the insert and 500 µl of maintenance media is added to the basolateral side of the insert. The apical side of insert is washed three times with fresh media, and finally 20 ul of fresh apical media is added to each insert. Basolateral media is then supplemented with either +/−poly(I:C) (2.5 µg/mL) or +/−IL13 (10 ng/mL). Cells are then maintained for 7 days with 500 ul of basal and 20 ul of apical media, maintaining the indicated concentrations of poly(I:C) and IL13 in the basal media.

Apical supernatant is collected, cells are trypsinized, and cell lysates prepared using a RIPA buffer. The apical supernatant is used to perform a MUCSAC ELISA. Cell lysates are used to perform quantitative PCRs (RT-qPCR) or to perform Western blots using a TSLP antibody (Abcam) and a GAPDH antibody (Abcam) as a loading control.

Long-form and short-form TSLP, IL13, IL4, IL5, and TNF-alpha mRNA is quantified using real-time polymerase chain reaction. Total RNA is reverse transcribed to cDNA using a First-Strand III cDNA Synthesis kit (Invitrogen, Carlsbad, Calif.). Then, real-time quantitative polymerase chain reaction (PCR) is performed using the ABI Prism 7900 Sequence Detection System (Applied Biosystems, Foster City, Calif.). Amplification by PCR is performed according to the manufacturer's protocols (Applied Biosystems). Primers and probes for long and short-form TSLP and for β-actin are designed with the assistance of the computer program Primer Express (Applied Biosystems). Searches using a nucleotide basic local alignment search tool (BLASTN) database are conducted to confirm their specificity and the absence of DNA polymorphisms.

MUCSAC protein is measured from apical culture supernatants using a semiquantitative sandwich ELISA with two different MUCSAC antibodies, one for coating and one for detection. Briefly, high binding plates are coated with Neomarkers (Fremont, Calif.) MUCSAC antibody (1-13M1) at 1 µg/ml. Neomarker MUCSAC antibody (45M1) labeled with biotin is used at 0.2-0.4 µg/ml for detection. The MUCSAC standard is generated from the apical supernatants of NHBECs under ALI and diluted 1/100 for the high standard followed by serial half dilution. Thus, all results are in relative arbitrary units per ml (AU/ml) and semiquantitative. Samples are studied without dilution or up to 1/4000 dilution depending on sample.

Example 7

Bioinformatic Selection of Sequences in Order to Identify Therapeutic siRNAs to Downmodulate Expression of TSLP mRNA Screening sets were defined based on bioinformatic analysis. Therapeutic siRNAs were designed to target human TSLP as well as the TSLP sequence of at least one toxicology-relevant species such as non-human primates (NHP). This type of analysis allowed identification siRNAs specific to 1fTSLP and sfTSLP. Drivers for the design of the screening sets were predicted specificity of the siRNAs against the transcriptome of the relevant species as well as cross-reactivity between species. Predicted specificity in human, rhesus monkey, cynomolgus monkey, mouse and rat was determined for sense (S) and antisense (AS) strands. These were assigned a "specificity score" which considers the likelihood of unintended downregulation of any other transcript by full or partial complementarity of an siRNA strand (up to 4 mismatches within positions 2-18) as well as the number and positions of mismatches. Thus, the predicted most likely off-target(s) for antisense and sense strand of each siRNA were identified. In addition, the number of potential off-targets was used as an additional specificity factor in the specificity score. As identified, siRNAs with high specificity and a low number of predicted off-targets provide a benefit of increased targeting specificity.

In addition to selecting siRNA sequences with high sequence specificity to TSLP mRNA, siRNA sequences within the seed region were analyzed for similarity to seed regions of known miRNAs. siRNAs can function in a miRNA like manner via base-pairing with complementary sequences within the 3'-UTR of mRNA molecules. The complementarity typically encompasses the 5'-bases at positions 2-7 of the miRNA (seed region). In order to circumvent siRNAs to act via functional miRNA binding sites, siRNA strands are avoided that contain natural miRNA seed regions. Seed regions identified in miRNAs from human, mouse, rat, rhesus monkey, dog, rabbit and pig are referred to as "conserved". Combining the "specificity score" with miRNA seed analysis yields the "specificity category". This was divided into categories 1-4, with 1 having the highest specificity and 4 having the lowest specificity. Each strand of the siRNA was assigned to a specificity category.

Species cross-reactivity was assessed for human, cynomolgus monkey, rhesus monkey, mouse, rat and dog. The analysis was based on a canonical siRNA design using 19 bases and 17 bases (without considering positions 1 and 19) for cross-reactivity. Full match as well as single mismatch analyses were included.

Analysis of the human Single Nucleotide Polymorphism (SNP) database (NCBI-DB-SNP) to identify siRNAs targeting regions with known SNPs was also carried out in order to identify siRNAs that may be non-functional in individuals containing the SNP. Information regarding the positions of SNPs within the target sequence as well as minor allele frequency (MAF) in case data was obtained in this analysis.

2,591 siRNAs (sense strand sequences: SEQ ID NOS: 14935-17526; antisense strand sequences: SEQ ID NOS: 26134-28725) were bioinformatically derived from human 1fTSLP mRNA (NM_033035.5, SEQ ID NO. 14923) without consideration of specificity or species cross-reactivity. These siRNAs are prepared by annealing the sense strand of any one of SEQ ID NOS: 14935-17526 with its corresponding antisense strand among SEQ ID NOS: 26134-28725. In addition, "U" may be substituted for "T" in the sense and antisense strands. A subset of these sequences is also cross-reactive with human sfTSLP.

Prioritizing siRNA sequences for target specificity, species cross-reactivity, miRNA seed region sequences and SNPs yielded a set of siRNAs specific for 1fTSLP only (not sfTSLP). This subset included 88 siRNAs with sense strands in accordance with SEQ ID NOS: 14941, 14942, 14947, 14948, 14950, 14957, 14959, 14960, 14961, 14962, 14973, 15004, 15005, 15013, 15035, 15039, 15040, 15041, 15043, 15047, 15048, 15049, 15050, 15051, 15052, 15056, 15057, 15059, 15062, 15082, 15094, 15096, 15097, 15098, 15101, 15102, 15107, 15108, 15111, 15114, 15117, 15123, 15127, 15128, 15164, 15174, 15178, 15184, 15186, 15187, 15188, 15190, 15191, 15194, 15195, 15197, 15230, 15235, 15236, 15238, 15240, 15241, 15246, 15252, 15253, 15260, 15263, 15264, 15272, 15274, 15276, 15278, 15279, 15282, 15283, 15286, 15294, 15302, 15303, 15307, 15310, 15314, 15319, 15320, 15321, 15322, 15324, and 15326; and antisense strands in accordance with SEQ ID NOS: 26140, 26141, 26146, 26147, 26149, 26156, 26158, 26159, 26160, 26161, 26172, 26203, 26204, 26212, 26234, 26238, 26239, 26240, 26242, 26246, 26247, 26248, 26249, 26250, 26251, 26255, 26256, 26258, 26261, 26281, 26293, 26295, 26296, 26297, 26300, 26301, 26306, 26307, 26310, 26313, 26316, 26322, 26326, 26327, 26363, 26373, 26377, 26383, 26385, 26386, 26387, 26389, 26390, 26393, 26394, 26396, 26429, 26434, 26435, 26437, 26439, 26440, 26445, 26451, 26452, 26459, 26462, 26463, 26471, 26473, 26475, 26477, 26478, 26481, 26482, 26485, 26493, 26501, 26502, 26506, 26509, 26513, 26518, 26519, 26520, 26521, 26523, and 26525. These siRNAs tend to target sequences within the first 412 nucleotides of SEQ ID NO: 14923, particularly with nucleotides 8-412 of SEQ ID NO: 14923.

The siRNAs in this subset have the following characteristics:
Cross-reactivity: With 19 mer in human 1fTSLP mRNA
Specificity category: For human: AS2 or better, SS3 or better
miRNA seeds: AS+SS strand: seed region not conserved in human, mouse, and rat and not present in >3 species
Off-target frequency: ≤20 human off-targets matched with 2 mismatches in antisense strand
SNPs: siRNA target sites do not harbor SNPs with a MAF≥1% (pos. 2-18)

195 siRNAs (sense strand sequences: SEQ ID NOS: 22711-22906; antisense strand sequences: SEQ ID NOS: 28726-28921) specific for human sfTSLP mRNA (NM 138551.4, SEQ ID NO. 14924) were bioinformatically derived without consideration of specificity or species cross-reactivity. These siRNAs are prepared by annealing the sense strand of any one of SEQ ID NOS: 22711-22906 with its corresponding antisense strand among SEQ ID NOS: 28726-28921. In addition, "U" may be substituted for "T" in the sense and antisense strands.

Prioritizing siRNA sequences for target specificity, species cross-reactivity, miRNA seed region sequences and SNPs yielded a set of siRNAs specific for sfTSLP only. This subset included 37 siRNAs having sense strands in accordance with SEQ ID NOS: 22734, 22736, 22738, 22746, 22773, 22778, 22780, 22781, 22782, 22783, 22785, 22786, 22787, 22788, 22789, 22790, 22824, 22825, 22827, 22828, 22872, 22873, 22874, 22876, 22877, 22879, 22880, 22881, 22882, 22884, 22885, 22887, 22889, 22890, 22895, 22898, and 22904; and having antisense strands in accordance with SEQ ID NOS: 28749, 28751, 28753, 28761, 28788, 28793, 28795, 28796, 28797, 28798, 28800, 28801, 28802, 28803, 28804, 28805, 28839, 28840, 28842, 28843, 28887, 28888, 28889, 28891, 28892, 28894, 28895, 28896, 28897, 28899, 28900, 28902, 28904, 28905, 28910, 28913, and 28919.

The siRNAs in this subset have the following characteristics:
Cross-reactivity: With 19 mer in human sfTSLP mRNA
Specificity category: For human: AS2 or better, SS3 or better
miRNA seeds: AS+SS strand: seed region not conserved in human, mouse, and rat and not present in >3 species
Off-target frequency: ≤20 human off-targets matched with 2 mismatches in antisense strand
SNPs: siRNA target sites do not harbor SNPs with a MAF≥1% (pos. 2-18)

Example 8

Chemically Modified TSLP siRNAs

The siRNAs targeting 1fTSLP can be synthesized with chemical modifications with the sense strand having modification pattern 1S, and the antisense strand having modification pattern 1AS. "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand. Some siRNAs that may include these chemical modifications comprise sequences of any of SEQ ID NOs: 17527-20118 or 28922-31513.

The siRNAs targeting 1fTSLP can also be synthesized with chemical modifications with the sense strand having modification pattern 2S, and the antisense strand having modification pattern 3AS. "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand. Some siRNAs that may include these chemical modifications comprise sequences of any of SEQ ID NOs: 20119-22710 or 31514-34105.

The siRNAs targeting sfTSLP can be synthesized with chemical modifications with the sense strand having modification pattern 1S, and the antisense strand having modification pattern 1AS. "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand. Some siRNAs that may include these chemical modifications comprise sequences of any of SEQ ID NOs: 22907-23102 or 34106-34301.

The siRNAs targeting sfTSLP can also be synthesized with chemical modifications with the sense strand having modification pattern 2S, and the antisense strand having modification pattern 3AS. "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand. Some siRNAs that may include these chemical modifications comprise sequences of any of SEQ ID NOs: 23103-23298 or 34302-34497.

Example 9

Screening TSLP siRNAs for Activity in Cells in Culture

To facilitate screening of TSLP siRNAs, target sequence unique to 1fTSLP (nucleotide positions 1-410 of NM_033035.5 [SEQ ID NO: 14923]) and target sequence unique to sfTSLP (nucleotide positions 1-212 of NM_138551.4 [SEQ ID NO: 14924]) were each cloned as a single fragment into XhoI and NotI sites in a psiCheck-2 plasmid (Promega, Catalog #C8021, GenBank Accession #AY535007). These sequences are located downstream of a stop codon of a gene encoding Renilla luciferase. This way, the activity of the siRNAs could be measured by the degree of reduction of Renilla luciferase activity relative to the activity of the reference firefly luciferase encoded on the same plasmid.

Chemically modified TSLP siRNAs specifically targeting 1fTSLP (sense strand sequences: SEQ ID NOs: 25890-25977; antisense strand sequences: SEQ ID NOs: 26012-26099) or specifically targeting sfTSLP (sense strand sequences: SEQ ID NOs: 25978-26011; antisense strand sequences: SEQ ID NOs: 26100-26133) were assayed for activity. The siRNAs targeting 1fTSLP tend to target sequences within the first 412 nucleotides of SEQ ID NO:

14923, particularly with nucleotides 8-412 of SEQ ID NO: 14923. HEK-293 cells (ATCC No. CRL-1573), a human derived cell line that is easily transfected, were seeded in 96-well tissue culture plates at a cell density of 10,000 cells per well in 90% DMEM supplemented with 10% fetal bovine serum and incubated overnight in a water-jacketed, humidified incubator at 37° C. in an atmosphere of air plus 5% carbon dioxide. PsiCheck-2 plasmids encoding the 1fTSLP and sfTSLP sequences were transfected into cells in triplicate wells at a final concentration of 0.2 ug DNA using 0.3 uL TransIT-2020 (Mims Bio, Catalog #MIR5404). Cells were allowed to recover in a humidified incubator at 37° C. for 4 hours, after which the media was replaced with a fresh 100 uL 90% DMEM supplemented with 10% fetal bovine serum. The TSLP siRNAs were then individually transfected into cells in triplicate wells at a 3 nM final concentration using 0.3 uL Lipofectamine RNAiMax (ThermoFisher, Catalog #13778150) per well. Silencer Select Negative Control #1 (ThermoFisher, Catalog #4390843) and Silencer Select TSLP siRNA s34500 (ThermoFisher, Catalog #4392420) were transfected at a 3 nM final concentration as controls. After incubation for 48 hours at 37° C., cells were lysed and luciferase reporter luminescence developed using the Dual-Luciferase® Reporter Assay System (Promega, Catalog #E1980). Luciferase activity was measured in the GloMax Discover plate reader (Promega, Catalog #GM3000). The ratio of Renilla luciferase activity to reference firefly luciferase activity in each well was calculated. All data was normalized to the Renilla to firefly luminescence ratio in HEK-293 cells transfected only with the psiCheck-2 plasmid encoding the TSLP screening sequence. The data are shown in Table 3. These data show a surprising effect of some siRNAs to specifically knock down 1fTSLP or sfTSLP, in comparison with other siRNAs.

TABLE 3

Knockdown Activity of lfTSLP-Specific and sfTSLP-Specific siRNAs at 3 nM

| siRNA name | Sense Strand (SEQ ID NO) | Antisense Strand (SEQ ID NO) | Relative Knockdown |
|---|---|---|---|
| No siRNA | — | — | 1.00 |
| Silencer Select Negative Control #1 | — | — | 1.12 |
| Silencer Select Positive Control #1 | — | — | 0.47 |
| ETD00001 | 25890 | 26012 | 2.50 |
| ETD00002 | 25891 | 26013 | 0.75 |
| ETD00003 | 25892 | 26014 | 0.89 |
| ETD00004 | 25893 | 26015 | 0.84 |
| ETD00005 | 25894 | 26016 | 0.53 |
| ETD00006 | 25895 | 26017 | 0.69 |
| ETD00007 | 25896 | 26018 | 0.69 |
| ETD00008 | 25897 | 26019 | 1.16 |
| ETD00009 | 25898 | 26020 | 1.27 |
| ETD00010 | 25899 | 26021 | 1.50 |
| ETD00011 | 25900 | 26022 | 1.30 |
| ETD00012 | 25901 | 26023 | 0.73 |
| ETD00013 | 25902 | 26024 | 1.25 |
| ETD00014 | 25903 | 26025 | 1.98 |
| ETD00015 | 25904 | 26026 | 0.85 |
| ETD00016 | 25905 | 26027 | 0.56 |
| ETD00017 | 25906 | 26028 | 0.90 |
| ETD00018 | 25907 | 26029 | 0.37 |
| ETD00019 | 25908 | 26030 | 0.67 |
| ETD00020 | 25909 | 26031 | 0.52 |
| ETD00021 | 25910 | 26032 | 0.13 |
| ETD00022 | 25911 | 26033 | 0.65 |
| ETD00023 | 25912 | 26034 | 0.61 |
| ETD00024 | 25913 | 26035 | 0.37 |
| ETD00025 | 25914 | 26036 | 0.91 |
| ETD00026 | 25915 | 26037 | 1.43 |
| ETD00027 | 25916 | 26038 | 0.83 |
| ETD00028 | 25917 | 26039 | 0.87 |
| ETD00029 | 25918 | 26040 | 3.61 |
| ETD00030 | 25919 | 26041 | 0.38 |
| ETD00031 | 25920 | 26042 | 0.52 |
| ETD00032 | 25921 | 26043 | 0.34 |
| ETD00033 | 25922 | 26044 | 0.54 |
| ETD00034 | 25923 | 26045 | 0.55 |
| ETD00035 | 25924 | 26046 | 0.98 |
| ETD00036 | 25925 | 26047 | 0.55 |
| ETD00037 | 25926 | 26048 | 0.69 |
| ETD00038 | 25927 | 26049 | 0.54 |
| ETD00039 | 25928 | 26050 | 0.48 |
| ETD00040 | 25929 | 26051 | 0.48 |
| ETD00041 | 25930 | 26052 | 4.17 |
| ETD00042 | 25931 | 26053 | 0.35 |
| ETD00043 | 25932 | 26054 | 0.52 |
| ETD00044 | 25933 | 26055 | 0.48 |
| ETD00045 | 25934 | 26056 | 0.75 |
| ETD00046 | 25935 | 26057 | 1.35 |
| ETD00047 | 25936 | 26058 | 1.15 |
| ETD00048 | 25937 | 26059 | 0.51 |
| ETD00049 | 25938 | 26060 | 0.62 |
| ETD00050 | 25939 | 26061 | 0.29 |
| ETD00051 | 25940 | 26062 | 0.50 |
| ETD00052 | 25941 | 26063 | 0.81 |
| ETD00053 | 25942 | 26064 | 0.76 |
| ETD00054 | 25943 | 26065 | 0.31 |
| ETD00055 | 25944 | 26066 | 0.49 |
| ETD00056 | 25945 | 26067 | 1.59 |
| ETD00057 | 25946 | 26068 | 0.34 |
| ETD00058 | 25947 | 26069 | 0.48 |
| ETD00059 | 25948 | 26070 | 0.53 |
| ETD00060 | 25949 | 26071 | 0.25 |
| ETD00061 | 25950 | 26072 | 1.35 |
| ETD00062 | 25951 | 26073 | 0.25 |
| ETD00063 | 25952 | 26074 | 0.65 |
| ETD00064 | 25953 | 26075 | 0.33 |
| ETD00065 | 25954 | 26076 | 1.18 |
| ETD00066 | 25955 | 26077 | 0.88 |
| ETD00067 | 25956 | 26078 | 0.88 |
| ETD00068 | 25957 | 26079 | 1.01 |
| ETD00069 | 25958 | 26080 | 0.34 |
| ETD00070 | 25959 | 26081 | 0.98 |
| ETD00071 | 25960 | 26082 | 0.55 |
| ETD00072 | 25961 | 26083 | 0.46 |
| ETD00073 | 25962 | 26084 | 0.86 |
| ETD00074 | 25963 | 26085 | 1.15 |
| ETD00075 | 25964 | 26086 | 0.74 |
| ETD00076 | 25965 | 26087 | 0.98 |
| ETD00077 | 25966 | 26088 | 0.81 |
| ETD00078 | 25967 | 26089 | 0.50 |
| ETD00079 | 25968 | 26090 | 1.48 |
| ETD00080 | 25969 | 26091 | 0.45 |
| ETD00081 | 25970 | 26092 | 0.94 |
| ETD00082 | 25971 | 26093 | 0.69 |
| ETD00083 | 25972 | 26094 | 1.12 |
| ETD00084 | 25973 | 26095 | 1.02 |
| ETD00085 | 25974 | 26096 | 1.13 |
| ETD00086 | 25975 | 26097 | 0.75 |
| ETD00087 | 25976 | 26098 | 0.55 |
| ETD00088 | 25977 | 26099 | 0.36 |
| ETD00089 | 25978 | 26100 | 0.51 |
| ETD00090 | 25979 | 26101 | 0.64 |
| ETD00091 | 25980 | 26102 | 0.52 |
| ETD00092 | 25981 | 26103 | 0.53 |
| ETD00093 | 25982 | 26104 | 0.46 |
| ETD00094 | 25983 | 26105 | 0.41 |
| ETD00095 | 25984 | 26106 | 0.84 |
| ETD00096 | 25985 | 26107 | 0.97 |
| ETD00098 | 25986 | 26108 | 0.97 |
| ETD00099 | 25987 | 26109 | 0.78 |
| ETD00100 | 25988 | 26110 | 1.28 |

TABLE 3-continued

Knockdown Activity of lfTSLP-Specific and sfTSLP-Specific siRNAs at 3 nM

| siRNA name | Sense Strand (SEQ ID NO) | Antisense Strand (SEQ ID NO) | Relative Knockdown |
|---|---|---|---|
| ETD00101 | 25989 | 26111 | 1.57 |
| ETD00102 | 25990 | 26112 | 0.66 |
| ETD00103 | 25991 | 26113 | 0.90 |
| ETD00104 | 25992 | 26114 | 0.67 |
| ETD00105 | 25993 | 26115 | 0.83 |
| ETD00106 | 25994 | 26116 | 0.86 |
| ETD00107 | 25995 | 26117 | 0.73 |
| ETD00108 | 25996 | 26118 | 0.85 |
| ETD00109 | 25997 | 26119 | 0.82 |
| ETD00110 | 25998 | 26120 | 0.28 |
| ETD00111 | 25999 | 26121 | 0.57 |
| ETD00112 | 26000 | 26122 | 0.57 |
| ETD00113 | 26001 | 26123 | 1.19 |
| ETD00114 | 26002 | 26124 | 0.94 |
| ETD00115 | 26003 | 26125 | 0.64 |
| ETD00116 | 26004 | 26126 | 1.38 |
| ETD00117 | 26005 | 26127 | 0.67 |
| ETD00118 | 26006 | 26128 | 0.91 |
| ETD00119 | 26007 | 26129 | 0.81 |
| ETD00120 | 26008 | 26130 | 0.81 |
| ETD00123 | 26009 | 26131 | 0.93 |
| ETD00124 | 26010 | 26132 | 0.49 |
| ETD00125 | 26011 | 26133 | 0.52 |

The TSLP siRNAs showing the greatest degree of knockdown of TSLP mRNA at 3 nM were tested in a second screen for activity at 10 nM concentration using the transfection procedures as described above. The data are shown in Table 4. These data validate the effectiveness of the siRNAs in the table to specifically knock down 1fTSLP or sfTSLP.

TABLE 4

Knockdown Activity of Some lfTSLP-Specific and sfTSLP-Specific siRNAs at 10 nM

| siRNA name | Sense Strand (SEQ ID NO) | Antisense Strand (SEQ ID NO) | Relative Knockdown |
|---|---|---|---|
| No siRNA | — | — | 1 |
| Silencer Select Negative Control #1 | — | — | 0.85 |
| Silencer Select Positive Control #1 | — | — | 0.32 |
| ETD00018 | 25907 | 26029 | 0.32 |
| ETD00021 | 25910 | 26032 | 0.31 |
| ETD00024 | 25913 | 26035 | 0.46 |
| ETD00030 | 25919 | 26041 | 0.44 |
| ETD00032 | 25921 | 26043 | 0.35 |
| ETD00039 | 25928 | 26050 | 0.59 |
| ETD00040 | 25929 | 26051 | 0.53 |
| ETD00042 | 25931 | 26053 | 0.3 |
| ETD00044 | 25933 | 26055 | 0.4 |
| ETD00050 | 25939 | 26061 | 0.2 |
| ETD00054 | 25943 | 26065 | 0.42 |
| ETD00057 | 25946 | 26068 | 0.21 |
| ETD00058 | 25947 | 26069 | 0.19 |
| ETD00060 | 25949 | 26071 | 0.35 |
| ETD00062 | 25951 | 26073 | 0.47 |
| ETD00064 | 25953 | 26075 | 0.44 |
| ETD00069 | 25958 | 26080 | 0.29 |
| ETD00072 | 25961 | 26083 | 0.37 |
| ETD00080 | 25969 | 26091 | 0.22 |
| ETD00088 | 25977 | 26099 | 0.22 |
| ETD00093 | 25982 | 26104 | 0.24 |
| ETD00094 | 25983 | 26105 | 0.29 |
| ETD00110 | 25998 | 26120 | 0.24 |
| ETD00124 | 26010 | 26132 | 0.54 |

Example 10

Activity of 1fTSLP siRNAs Against Endogenously Expressed TSLP mRNA

To further confirm activity of 1fTSLP siRNAs screened using the psiCheck-2 TSLP luciferase assay, siRNA activity was tested in a human derived cell line LN-18 that expresses TSLP (ATCC No. CRL-2610). Cells were seeded in 96-well tissue culture plates at a cell density of 10,000 cells per well in 95% DMEM supplemented with 5% fetal bovine serum and incubated overnight in a water-jacketed, humidified incubator at 37° C. in an atmosphere composed of air plus 5% carbon dioxide. The TSLP siRNAs were individually transfected into cells in triplicate wells at a 10 nM final concentration using 0.3 uL Lipofectamine RNAiMax (ThermoFisher, Catalog #13778150) per well. Silencer Select Negative Control #1 (ThermoFisher, Catalog #4390843) and Silencer Select TSLP siRNA s34500 (ThermoFisher, Catalog #4392420) were transfected at a 10 nM final concentration as controls. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of TSLP mRNA from each well was measured in triplicate by real-time qPCR on an Applied Biosystems 7500 Fast Real-Time PCR machine using TaqMan Gene Expression Assay for human TSLP (ThermoFisher, assay #Hs01572934_g1). The level of PPIA mRNA was measured using TaqMan Gene Expression Assay (ThermoFisher, assay #Hs99999904_m1) and used to determine relative TSLP mRNA levels in each well using the delta-delta Ct method. All data was normalized to relative TSLP mRNA levels in untreated LN-18 cells. The data are shown in Table 5. These data show a further surprising effect of some siRNAs to specifically knock down 1fTSLP or sfTSLP, in comparison with other siRNAs, in cells that endogenously express TSLP.

TABLE 5

Knockdown Activity of Select lfTSLP-Specific siRNAs at 10 nM in LN-18 Cells

| siRNA name | Sense Strand (SEQ ID NO) | Antisense Strand (SEQ ID NO) | Relative Knockdown |
|---|---|---|---|
| No siRNA | — | — | 1 |
| Silencer Select Negative Control #1 | — | — | 0.55 |
| Silencer Select Positive Control #1 | — | — | 0.15 |
| ETD00018 | 25907 | 26029 | 1.04 |
| ETD00021 | 25910 | 26032 | 0.52 |
| ETD00024 | 25913 | 26035 | 0.64 |
| ETD00030 | 25919 | 26041 | 0.8 |
| ETD00032 | 25921 | 26043 | 0.54 |
| ETD00039 | 25928 | 26050 | 0.57 |
| ETD00040 | 25929 | 26051 | 0.59 |
| ETD00042 | 25931 | 26053 | 0.37 |
| ETD00044 | 25933 | 26055 | 0.74 |
| ETD00050 | 25939 | 26061 | 1.92 |
| ETD00054 | 25943 | 26065 | 0.21 |
| ETD00057 | 25946 | 26068 | 0.23 |
| ETD00058 | 25947 | 26069 | 0.24 |
| ETD00060 | 25949 | 26071 | 0.2 |
| ETD00062 | 25951 | 26073 | 0.26 |
| ETD00064 | 25953 | 26075 | 0.38 |
| ETD00069 | 25958 | 26080 | 0.4 |
| ETD00072 | 25961 | 26083 | 0.49 |
| ETD00080 | 25969 | 26091 | 0.25 |
| ETD00088 | 25977 | 26099 | 0.3 |

Example 11

Determining the IC50 of 1fTSLP siRNAs

The IC50 values for knockdown of TSLP mRNA by select TSLP siRNAs shown to possess high knockdown in the activity screen will be determined by assaying individual siRNAs at 3 nM, 1 nM, 0.3 nM, 0.1 nM and 0.03 nM. A human derived cell line that expresses TSLP such as LN-18 (ATCC No. CRL-2610) is to be seeded in 96-well tissue culture plates at a cell density of 10,000 cells per well in 95% DMEM supplemented with 5% fetal bovine serum and incubated overnight in a water-jacketed, humidified incubator at 37° C. in an atmosphere composed of air plus 5% carbon dioxide. The TSLP siRNAs will be individually transfected into cells in triplicate wells using 0.3 uL Lipofectamine RNAiMax (ThermoFisher, Catalog #13778150) per well. Silencer Select Negative Control #1 (ThermoFisher, Catalog #4390843) is to be transfected at 3 nM final concentration as a control. After incubation for 48 hours at 37° C., total RNA is harvested from each well and cDNA prepared using TaqMan® Fast Advanced Cells-to-CT™ Kit (ThermoFisher, Catalog #A35374) according to the manufacturer's instructions. The level of TSLP mRNA from each well is measured in triplicate by real-time qPCR on an Applied Biosystems 7500 Fast Real-Time PCR machine using TaqMan Gene Expression Assay for human TSLP (ThermoFisher, assay #Hs01572934 g1). The level of PPIA mRNA is measured using TaqMan Gene Expression Assay (ThermoFisher, assay #Hs99999904 m1) and used to determine relative TSLP mRNA levels in each well using the delta-delta Ct method. All data are normalized to relative TSLP mRNA levels in untreated cells. Curve fit is accomplish using the [inhibitor] vs. response (three parameters) function in GraphPad Prism software.

Example 12

Assessing the Extent of Nuclease Resistance of TSLP siRNAs

TSLP siRNAs that possess high activity and low IC50 values will be tested for resistance to nuclease digestion by incubating the siRNAs in rat liver tritosomes. In addition to these TSLP siRNAs, corresponding versions of these TSLP siRNAs possessing alternative chemical modification patterns will also be tested, for example those corresponding 1fTSLP siRNAs with sense strands having modification pattern 2S and sequences in accordance with SEQ ID NOs: 20125, 20126, 20131, 20132, 20134, 20141, 20143, 20144, 20145, 20146, 20157, 20188, 20189, 20197, 20219, 20223, 20224, 20225, 20227, 20231, 20232, 20233, 20234, 20235, 20236, 20240, 20241, 20243, 20246, 20266, 20278, 20280, 20281, 20282, 20285, 20286, 20291, 20292, 20295, 20298, 20301, 20307, 20311, 20312, 20348, 20358, 20362, 20368, 20370, 20371, 20372, 20374, 20375, 20378, 20379, 20381, 20414, 20419, 20420, 20422, 20424, 20425, 20430, 20436, 20437, 20444, 20447, 20448, 20456, 20458, 20460, 20462, 20463, 20466, 20467, 20470, 20478, 20486, 20487, 20491, 20494, 20498, 20503, 20504, 20505, 20506, 20508, or 20510, and antisense strand having modification pattern 3AS and sequences in accordance with SEQ ID NOs: 31520, 31521, 31526, 31527, 31529, 31536, 31538, 31539, 31540, 31541, 31552, 31583, 31584, 31592, 31614, 31618, 31619, 31620, 31622, 31626, 31627, 31628, 31629, 31630, 31631, 31635, 31636, 31638, 31641, 31661, 31673, 31675, 31676, 31677, 31680, 31681, 31686, 31687, 31690, 31693, 31696, 31702, 31706, 31707, 31743, 31753, 31757, 31763, 31765, 31766, 31767, 31769, 31770, 31773, 31774, 31776, 31809, 31814, 31815, 31817, 31819, 31820, 31825, 31831, 31832, 31839, 31842, 31843, 31851, 31853, 31855, 31857, 31858, 31861, 31862, 31865, 31873, 31881, 31882, 31886, 31889, 31893, 31898, 31899, 31900, 31901, 31903, or 31905; or 1fTSLP siRNAs with sense strands having modification pattern 2S and sequences in accordance with any of SEQ ID NOs: 23103-23298, and antisense strand having Modification Pattern 3AS and sequences in accordance with any of SEQ ID NOs: 34302-34497, including sfTSLP siRNAs with sense strands having Modification Pattern 2S and sequences in accordance with SEQ ID NOs: 23126, 23128, 23130, 23138, 23165, 23170, 23172, 23173, 23174, 23175, 23177, 23178, 23179, 23180, 23181, 23182, 23216, 23217, 23219, 23220, 23264, 23265, 23266, 23268, 23269, 23271, 23272, 23273, 23274, 23276, 23277, 23279, 23281, 23282, 23287, 23290, or 23296, and antisense strand having modification pattern 3AS and sequences in accordance with SEQ ID NOs: 34521, 34523, 34525, 34533, 34560, 34565, 34567, 34568, 34569, 34570, 34572, 34573, 34574, 34575, 34576, 34577, 34611, 34612, 34614, 34615, 34659, 34660, 34661, 34663, 34664, 34666, 34667, 34668, 34669, 34671, 34672, 34674, 34676, 34677, 34682, 34685, or 34691. Each siRNA (14 ng/uL final concentration) will be placed into a PCR tube on ice containing 1× catabolic buffer (Xenotech, Catalog #K5200, Lot #18-1-0698), 0.5× rat tritosomes (Xenotech, Catalog #R0610.LT or Lot #1610405), 0.1 U/uL porcine intestinal heparin (Zageno, Catalog #H3149-10KU) in a total volume of 33 uL. An 10 uL aliquot is to be removed, an equal volume of 50 mM EDTA bill be added and the aliquot is placed at −80° C. This sample is designated as the 0 hr timepoint. The remainder of the reaction is placed in an Eppendorf Mastercycler Gradient and incubated at 37° C. Aliquots are removed after incubation for 4 and 24 hours, placed in an equal volume of 50 mM EDTA and stored at −80° C. until analysis by gel electrophoresis. All samples are then to be thawed on ice and 6×DNA Gel Loading Dye (ThermoFisher Catalog #R0611) is added to 1× final concentration. 10 uL of each sample is loaded onto a 20% polyacrylamide TBE gel (ThermoFisher, Catalog #EC63155BOX). Electrophoresis is carried out at a constant 100V for 75 minutes in an XCell SureLock Mini-Cell Electrophoresis System (ThermoFisher) using 1×TBE (Tris/boric/EDTA) (Fisher, Catalog #FERB52) as the tank buffer. The siRNA is visualized by staining the gel with a 1:10,000 dilution of SYBR Gold (ThermoFisher, Catalog #S-11494) in TBE for 15 minutes at room temperature with rocking. The gel is to be washed with 1×TBE for 15 minutes and then placed on a FotoPrep1 UV transilluminator (Fotodyne). The gel will be imaged using the camera app set on MONO on an iPhone 6s with a yellow gel filter (Neewer) placed over the lens. Band intensity is measured using NIH ImageJ using the "Analyze: Gels" function. The remaining siRNA percent is to be normalized to the value obtained at the 0 hr timepoint for that siRNA. This assay will provide the benefit of helping to determine that some siRNAs are more resistant to nuclease digestion with more remaining intact over time compared with other siRNAs.

Example 13

Screening TSLP Antisense Oligonucleotides (ASOs) for Activity in Cells in Culture Chemically modified TSLP ASOs with nucleoside sequences in accordance with SEQ ID NOs: 23299-25889 may be derived from the ASO sequences with nucleoside sequences in accordance with SEQ ID NOs: 9971-12561 and target human 1fTSLP pre-mRNA sequence (SEQ ID NO: 14923). They may have modification pattern 5'-nsnsnsnsnsdNsdNsdNsdNsdNsdNsdNsdNsdNsdNsnsnsn snsn-3' (SEQ ID NO: 34506) where "dN" is any deoxynucleotide, "n" is a 2'O-methyl or 2'O-methoxyethyl-modified nucleoside, and "s" is a phosphorothioate linkage. These modified ASOs are to be assayed for TSLP mRNA reduction activity in cells in culture. A human derived cell line that expresses TSLP such as LN-18 (ATCC No. CRL-2610) will be seeded in 96-well tissue culture plates at a cell density of 10,000 cells per well in 95% DMEM supplemented with 5% fetal bovine serum and incubated overnight in a water-jacketed, humidified incubator at 37° C. in an atmosphere composed of air plus 5% carbon dioxide. The TSLP ASOs are to be individually transfected into cells in duplicate wells at 1 uM final concentration using 0.3 uL Lipofectamine RNAiMax (ThermoFisher, Catalog #13778150) per well. A negative control ASO (SEQ ID NO: 14928) is also transfected at 1 uM final concentration. After incubation for 48 hours at 37° C., total RNA is harvested from each well and cDNA prepared using TaqMan® Fast Advanced Cells-to-CT™ Kit (ThermoFisher, Catalog #A35374) according to the manufacturer's instructions. The level of TSLP mRNA from each well is measured in triplicate by real-time qPCR on an Applied Biosystems 7500 Fast Real-Time PCR machine using TaqMan Gene Expression Assay for human TSLP (ThermoFisher, assay #Hs01572934 g1). The level of PPIA mRNA is measured using TaqMan Gene Expression Assay (ThermoFisher, assay #Hs99999904_m1) and used to determine relative TSLP mRNA levels in each well using the delta-delta Ct method. All data is normalized to relative TSLP mRNA levels in untreated LN-18 cells.

The TSLP ASOs showing the greatest degree of knockdown of TSLP mRNA at 1 uM will be tested in a second screen for activity at 100 nM concentration using the transfection procedures as described above.

Example 14

Inhibition of 1fTSLP in a Clinical Trial Using siRNA and ASO Specific for 1fTSLP In this study, human subjects with asthma, nasal polyps, allergic rhinitis, and chronic rhinosinusitis are to be used to evaluate the effect of siRNA or single-stranded ASO inhibition of 1fTSLP in the airway. Fifteen groups of subjects will be assessed (n=10/group) in the study: normal control subjects with a control oligonucleotide, normal control subjects with a siRNA oligonucleotide, normal control subjects with a single-stranded ASO oligonucleotide, asthma subjects with a control oligonucleotide, asthma subjects with a siRNA oligonucleotide, asthma subjects with a single-stranded ASO oligonucleotide, nasal polyps subjects with a control oligonucleotide, nasal polyps subjects with a siRNA oligonucleotide, nasal polyps subjects with a single-stranded ASO oligonucleotide, allergic rhinitis subjects with a control oligonucleotide, allergic rhinitis subjects with a siRNA oligonucleotide, allergic rhinitis subjects with a single-stranded ASO oligonucleotide, chronic rhinosinusitis subjects with a control oligonucleotide, chronic rhinosinusitis subjects with a siRNA oligonucleotide, and chronic rhinosinusitis subjects with a ASO oligonucleotide. Each subject will be given 10 biweekly aerosol applications of the control oligonucleotide, the siRNA oligonucleotide, or the single-stranded ASO oligonucleotide to the subject's airway. The siRNA oligonucleotide sequences are chosen from Table 5, and the ASO oligonucleotide sequences are to be chosen from the ASO sequences that show the most inhibition of 1fTSLP in screening assays (Example 13). Subjects' airways will be observed, and blood samples will be collected at baseline and at 3, 6, and 12 weeks of the study, and analyzed for decreases in the size or number of nasal polyps, airway constriction, blood eosinophil numbers, airway inflammation, and serum inflammation markers. In addition, cheek skin samples will be collected for assessment of 1fTSLP mRNA levels.

It is expected that subjects treated with the siRNA and single-stranded ASO oligonucleotides, but not the control oligonucleotide, will have reductions in the size or number of nasal polyps, airway constriction, blood eosinophil numbers, airway inflammation, and serum inflammation markers, compared with baseline measurements and compared with subjects receiving the control oligonucleotide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11452738B2). An electronic copy of the "Sequence Listing" will also be available from the USPTO upon request and payment of the fee set forth in 37 CFR 1.19(b)(3).

---

We claim:

1. A composition comprising an oligonucleotide that targets a long isoform of Thymic stromal lymphopoietin (1fTSLP), wherein the oligonucleotide comprises a small interfering RNA (siRNA) comprising a sense strand and an antisense strand; and wherein the sense strand comprises the nucleoside sequence of any one of SEQ ID NOs: 15048, 15114, 15194, 15252 or 15272, or a nucleic acid sequence thereof having 1 or 2 nucleoside substitutions, additions, or deletions.

2. The composition of claim 1, wherein the sense strand comprises modification pattern 1S: 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage.

3. The composition of claim 1, wherein the antisense strand comprises modification pattern 1AS: 5'-nsNfsnNfnNfnNfnNfnnnNfnNfnNfnsnsn-3' (SEQ ID NO: 34503), wherein "Nf" is a 2' fluoro-modified nucleoside, "n" is a 2' O-methyl modified nucleoside, and "s" is a phosphorothioate linkage.

4. The composition of claim 1, wherein the sense strand or the antisense strand comprises a 3' overhang comprising at least 2 nucleosides.

5. The composition of claim 1, further comprising a pharmaceutically acceptable carrier comprising water, a buffer, a saline solution, or a combination thereof.

6. The composition of claim 1, wherein the composition is formulated for administration by inhalation.

7. A method of treating an airway inflammation disorder in a subject in need thereof, the method comprising administering to the subject a pharmaceutical composition comprising an siRNA that targets 1fTSLP, comprising a sense strand and an antisense strand; and wherein the sense strand comprises the nucleoside sequence of any one of SEQ ID NOs: 15048, 15114, 15194, 15252 or 15272, or a nucleic acid sequence thereof having 1 or 2 nucleoside substitutions, additions, or deletions.

8. The method of claim 7, wherein the airway inflammation disorder comprises asthma, nasal polyps, allergic rhinitis, chronic rhinosinusitis, or a combination thereof.

9. The method of claim 7, wherein the subject is a human.

10. The method of claim 7, wherein the administration is by inhalation.

11. The method of claim 7, wherein the administration reduces a size or number of nasal polyps relative to a baseline size or number of nasal polyps.

12. The method of claim 7, wherein the administration reduces an airway constriction measurement relative to a baseline airway constriction measurement.

13. The method of claim 7, wherein the composition reduces a blood eosinophil measurement relative to a baseline blood eosinophil measurement.

14. The method of claim 7, wherein the sense strand comprises modification pattern 1S: 5'-NfsnsNfnNfnNfNfNfnNfnNfnNfnNfnNfsnsn-3' (SEQ ID NO: 34502), wherein "Nf" is a 2' fluoro-modified nucleoside, "n" is a 2' O-methyl modified nucleoside, and "s" is a phosphorothioate linkage; or wherein the antisense strand comprises modification pattern 1AS: 5'-nsNfsnNfnNfnNfnNfnnnNfnNfnNfnsnsn-3' (SEQ ID NO: 34503), wherein "Nf" is a 2' fluoro-modified nucleoside, "n" is a 2' O-methyl modified nucleoside, and "s" is a phosphorothioate linkage.

15. The method of claim 7, wherein the sense strand or the antisense strand comprises a 3' overhang comprising at least 2 nucleosides.

* * * * *